(12) United States Patent  (10) Patent No.: US 7,889,334 B2
Krause et al.  (45) Date of Patent: *Feb. 15, 2011

(54) SURFACE ENHANCED RAMAN SPECTROSCOPY (SERS) SYSTEMS FOR THE DETECTION OF BACTERIA AND METHODS OF USE THEREOF

(75) Inventors: Duncan C. Krause, Athens, GA (US); Suzanne Marie Larkin Hennigan, Bogart, GA (US); Richard A. Dluhy, Athens, GA (US); Jeremy Driskell, Athens, GA (US); Yiping Zhao, Statham, GA (US); Ralph A. Tripp, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 158 days.

This patent is subject to a terminal disclaimer.

(21) Appl. No.: 12/214,025

(22) Filed: Jun. 16, 2008

(65) Prior Publication Data

US 2009/0082220 A1 Mar. 26, 2009

Related U.S. Application Data

(63) Continuation-in-part of application No. 11/495,980, filed on Jul. 28, 2006, now Pat. No. 7,583,379, and a continuation-in-part of application No. 11/376,661, filed on Mar. 15, 2006, now Pat. No. 7,738,096.

(60) Provisional application No. 60/662,089, filed on Mar. 15, 2005, provisional application No. 60/703,110, filed on Jul. 28, 2005, provisional application No. 60/944,144, filed on Jun. 15, 2007.

(51) Int. Cl.
*G01J 3/44* (2006.01)

(52) U.S. Cl. ............... 356/301; 436/164; 436/171; 435/6
(58) Field of Classification Search .......... 356/301
See application file for complete search history.

(56) References Cited

U.S. PATENT DOCUMENTS

| 6,180,415 | B1 | 1/2001 | Schultz et al. | 436/518 |
| 6,376,177 | B1 | 4/2002 | Poponin | 435/6 |
| 7,192,703 | B2 | 3/2007 | Sun et al. | |
| 7,267,948 | B2 | 9/2007 | Vo-Dinh | |

(Continued)

FOREIGN PATENT DOCUMENTS

EP 0 261 642 9/1987

(Continued)

OTHER PUBLICATIONS

Wang, et al.; Layer uniformity of glancing angle deposition; Vaccum; vol. 78, Issue 1, Apr. 4, 2005, pp. 107-111.

(Continued)

*Primary Examiner*—L. G Lauchman
(74) *Attorney, Agent, or Firm*—Thomas, Kayden, Horstemeyer & Risley, LLP

(57) ABSTRACT

Surface-enhanced Raman spectroscopic (SERS) systems and methods for detecting biomolecules of interest, such as a bacterium or virus are provided.

23 Claims, 34 Drawing Sheets
(20 of 34 Drawing Sheet(s) Filed in Color)

U.S. PATENT DOCUMENTS

| | | | |
|---|---|---|---|
| 7,361,313 | B2 | 4/2008 | Chan et al. |
| 7,397,558 | B2 | 7/2008 | Kamins et al. |
| 7,400,395 | B2 | 9/2008 | Chan et al. |
| 7,583,379 | B2 * | 9/2009 | Zhao et al. .................. 356/301 |
| 2004/0224321 | A1 | 11/2004 | Nicolau et al. |
| 2006/0147927 | A1 | 7/2006 | Geddes et al. |
| 2006/0250613 | A1 * | 11/2006 | Demuth et al. .............. 356/301 |
| 2007/0048746 | A1 * | 3/2007 | Su et al. ........................ 435/6 |
| 2008/0059135 | A1 | 3/2008 | Murugkar et al. |
| 2008/0096005 | A1 * | 4/2008 | Premasiri .................... 428/323 |
| 2009/0155811 | A1 * | 6/2009 | Natan et al. .................. 435/7.1 |

FOREIGN PATENT DOCUMENTS

| | | |
|---|---|---|
| WO | 2004059279 | 7/2004 |
| WO | 2004074790 | 9/2004 |
| WO | WO 2006/066180 | 12/2005 |
| WO | 2006/137885 | 12/2006 |
| WO | 2007059514 | 5/2007 |
| WO | 2008045114 | 4/2008 |

OTHER PUBLICATIONS

Schubert, et al.; Nanostructure fabrication by glancing angle ion beam assisted deposition of silicon; Applied Physics A: Materials Science & Processing; vol. 81, No. 3 / Aug. 2005.
Brett, et al.; Glancing Angle Deposition, An Overview of Thin Films and GLAD; http://www.ece.ualberta.ca/~glad/glad.html; 2006.
Gish, et al.; Evaluation of silver nanostructures fabricated using glancing angle deposition as localized surface plasmon resonance biosensors; Nanotech 2007 Conference Program Abstract.
Zhao, et al.; Designing Nanostructures by Glancing Angle Deposition; Proceedings of SPIE; vol. 5219; Nanotubes and Nanowires; Invited Paper, pp. 59-73.
Katherine A. Willets and Richard P. Van Duyne; Localized Surface Plasmon Resonance Spectroscopy and Sensing; Annual Review of Physical Chemistry; vol. 58: 267-297 (Volume publication date May 2007); First published online as a Review in Advance on Oct. 26, 2006.
Surface-Enhanced Vibrational Spectroscopy.
ARS Project: 408043—Annual Reports for 2004-2007; USDA Agricultural Research Service.
Big Discovery Symposium 2006; UC Santa Barbara; Epigenetic Enzymes and Therapies; slide show.
Kathy Kincade; Raman Spectroscopy: SERS and Silver Nanorods Quickly Reveal Viral Structures; Laser Focus World; Jan. 1, 2007.
Kathy Kincade; Optoelectronic Applications: Nanophotonics—An "Old" Technique Finds New Life in the Nano World; Laser Focus World; Oct. 1, 2006.
Kawai, et al.; Raman Spectroscopic Probes Withstand Hostile Environments; Laser Focus World; Jun. 1, 2005.
Amri, et al.; Adenine and RNA in Mineral Samples. Surface-Enhanced Raman Spectroscopy (SERS) for Picomole Detections; Spectrochimica Acta Part A 59 (2003) pp. 2645-2654.
Stuart, et al.; In Vivo Glucose Measurement by Surface-Enhanced Raman Spectroscopy; Anal. Chem. 2006, 78, pp. 7211-7215.
Faulds, et al.; DNA Detection by Surface Enhanced Resonance Raman Scattering (SERRS); The Royal Society of Chemistry 2005; Analyst, 2005, 130, pp. 1125-1131.
Bell, et al.; Surface-Enhanced Raman Spectroscopy (SERS) for Sub-Micromolar Detection of DNA/RNA Mononucleotides; J. Am. Chem. Soc. 2006, 128, pp. 15580-15581.
Yun Wei Charles Cao, et al.; Nanoparticles with Raman Spectroscopic Fingerprints for DNA and RNA Detection; Science, 297; 2002; pp. 1536-1540.
Mecham, et al.; Research on Bettering Surveillance of Arboviral Threats, Using West Nile Virus as a Model; USDA Agricultural Research Service; abstract.
Gish, et al.; Evaluation of Silver nanostructures Fabricated Using Glancing Angle Deposition as Localized Surface Plasmon Resonance Biosensors; The Nanotechnology Conference and Trade Show; Boston, Jun. 1-5, 2008; abstract.
Wang, et al.; Layer Uniformity of Glancing Angle Deposition; Vacuum; 78; 2005; pp. 107-111.
Schubert; Nanostructure Fabrication by Blancing Angle Ion Beam Assisted Deposition of Silicon; Appl. Physc. A81, 481-486 (2005).
Willets, et al.; Localized Surface Plasmon Resonance Spectroscopy and Sensing; Annu. Rev. Phys. Chem 2007; 52; 267-297.
Prokes, et al.; Enhanced Plasmon Coupling in Crossed Dielectrics/Metal Nanowire Composite Geometries and Applications to Surface-Enhanced Raman Spectroscopy; Appl. Physc. Lett; 90; 2007; 3 pages.
D. Keith Roper; Determining Surface Plasmon Resonance Response Factors for Deposition onto Three-Dimensional Surfaces; Chemical Engineering Science; 62; 2007; pp. 1988-1996.
Takemoto, et al.; A Surface Plasmon Resonance Assay for the Binding of Influenza Virus Hemagglutinin to Its Sialic Acid Receptor; Virology; 217; 452-458 (1996) Article No. 0139.
Hardy, et al.; Valency of Antibody Binding to Enveloped Virus Particles as Determined by Surface Plasmon Resonance; Journal of Virology; Jan. 2003; p. 1649-1652; vol. 77, No. 2.
A Graded Improvement; Science, vol. 319; Feb. 29, 2008, p. 1163.
Kim; et al.; Light-Extraction Enhancement of GaInN Light-Emitting Diodes by Graded-Refractive-Index Indium Tin Oxide Anti-Reflection Contact; Adv. Mater. 2008, 20, pp. 801-804.
Robbie, et al.; Sculptured Thin Films and Glancing Angle Deposition: Growth Mechanics and Applications; J. Va. Sci. Technol. A 15(3), May/Jun. 1997; pp. 1460-1465.
Robbie, et al.; Fabrication of Thin Films With Highly Porous Microstructures; J. Va. Sci. Technol. A 13(3), May/Jun. 1995; pp. 1032-1035.
Robbie, et al.; First Thin Film Realization of a Helicoidal Bianisotropic Medium; J. Vac. Sc. Technol. A 13(6), Nov./Dec. 1995; pp. 2991-2993.
Vaeth, et al.; Transition Metals for Selective Chemical Vapor Deposition of Parylene-Based Polymers; Apr. 18, 2000; Chem. Mater, 2000, 12, pp. 1305-1313.
Vaeth, et al.; Use of Microcontact Printing for Generating Selectively Grown Films of Poly (p-phenylen vinylene) and Parylenes Prepared by Chemical Vapor Deposition; Sep. 22, 2000; Langmuir 2000, 16, pp. 8495-8500.
Pursel, et al.; Growth of Sculptured Polymer Submicronwire Assembles by Vapor Deposition; 2005; Polymer 46 (2005) pp. 95544-9548.
Hu, et al.; Fabrication, Characterization, and Application in SERS of Self-Assembled Polyelectrolyte-Gold Nanorod Multilayered Films; Sep. 22, 2005; J. Phys. Chem. B 2005, 109, pp. 19385-19389.
Guo, et al.; Bifunctioanl Au @pt Hybrid Nanorods; 2007; Journal of Colloid and Interface Science, 315 (2007) pp. 363-368.
Suzuki, et al.; Au Nanorod Arrays Tailored for Surface-Enhanced Raman Spectroscopy; 2007; Analytical Sciences; Jul. 2007, vol. 23; pp. 829-833.
Suzuki, et al.; In-Line Aligned and Bottom-Up Ag Nanorods for Surface-Enhanced Raman Spectroscopy; 2006; Applied Physics Letters; 88, 2003121 (2006); 3 pages.
Tiwari, et al.; Non-Resonance SERS Effects of Silver Colloids with Different Shapes; 2007; Chemical Physics Letters, 446 (2007) pp. 77-82.
Chu, et al.; A High Sensitive Fiber SERS Probe Based on Silver Nanorod Arrays; Optics Express; vol. 15, No. 19; Sep. 17, 207; pp. 12230-12239.
Chu, et al.; Silver Nanorod Arrays as a Surface-Enhanced Raman Scattering Substrate for Foodborne Pathogenic Bacteria Detection; 2008; Applied Spectroscopy, vol. 62, No. 8, 2008; pp. 922-931.
Yao, et al.; Cobalt and Nickel Nanorod Array Electrodes as New SERS Active Substrates; 2007; 2 pages.
Yang, et al.; Aligned Silver nanorod Arrays for Surface-Enhanced Rman Scattering; 2006; on-line at www.iop.org/EJ/abstract/0957-4484/17/10/038.
Zhao, et al.; Aligned Copper nanorod Arrays for Surface-enhanced Raman Scattering; 2007; online at http://ieeexplore.ieee.org/Xplore/dfdeny.jsp?url=/ie15/4295685/429...
Huang, et al.; Single-Domain Antibody-Conjugated nanoaggregate-Embedded Beads for Targeted Detection of Pathogenic Bacteria; Chem. Eur. J. 2009, 00, 0-0; pp. 1-6.

Bentley; "Microsensors: Invisible Watchdogs to Keep Us Safe and Well"; http://www.solve.csiro.au/0805/article1.htm; Aug. 2005; 4 pages.

Campion, et al.; "Surface-enhanced Raman scattering"; Chemical Society Reviews, vol. 27; 1998; 10 pages.

Carillo; "Sers nanoparticles: a new optical detection modality for rapid tests"; http://www.cli-online.com/en/featured-articles/sers-nanoparticles-a-new-optical-detection-modality-for-rapid-tests/trackback/1/index.html; Copyright 2004-2007; 4 pages.

Clin; "Applications of Nanobiotechnology in Clinical Diagnostics"; http://www.clinchem.org/cgi/content/full/53/11/2002; 2007; 1 page.

Driskell, et al.; "Low-Level Detection of Viral Pathogens by a Surface-Enhanced Raman Scattering Based Immunoassay"; 2005; 8 pages.

Fischer, et al.; "Heightened sense for sensing: recent advances in pathogen immunoassay sensing platforms"; Lawrence Livermore National Laboratory; Feb. 6, 2007; 13 pages.

Goeller, et al.; "Discrimination of Bacteria and Bacteriophages by Raman Spectroscopy and Surface-Enhanced Raman Spectroscopy"; Society for Applied Spectroscopy; vol. 61; Nov. 7, 2007; 7 page.

Gordon, et al.; "Plasmonic Sensors Based on Nano-Holes: Technology and Integration"; Micro and Nanotechnologies for Space, Defense, and Security II; vol. 6959; 2008; 6 pages.

Grabar, et al.; "Preparation and Characterization of Au Colloid Monolayers"; The Pennsylvania State University; vol. 67 Feb. 15, 1995; 9 pages.

Grow, et al.; "Evaluation of the Doodlebug: A Biochip for Detecting Waterborne Pathogens"; http://www.iwapublishing.com/template.cfm?name=isbn1843396688; Jun. 1, 2003; 1 page.

Grow, et al.; "New biochip technology for label-free detection of pahogens and their toxins"; Biopraxis, Inc.; Journal of Microbiological Methods; 2003; 13 pages.

Gu, et al.; "Biofunctional magnetic nanoparticles for protein separation and pathogen detection"; ChemComm; Jan. 19, 2006; 9 pages.

Hou, et al.; "Rapid Chip-Scale Detection by Micro-Spiral Flow and Surface Enhanced Raman Scattering"; http://aiche.confex.com/aiche/2006/techprogram/P66060.HTM; Nov. 15, 2006; 2 pages.

Kao, et al.; "Surface-Enhanced Raman Detection on Metalized Nanostructured Poly(p-xylylene) Films"; Advanced Materials; 2008; 4 pages.

Koo, et al.; "Single-molecule detection of biomolecules by surface-enhanced coherent anti-Stokes Raman scattering"; Optics Letters; vol. 30; May 1, 2005; 3 pages.

Richards; "Nano-optics: Imaging beyond the Diffraction Limit, Fluorescence and Lifetime Modification, Surface Enhanced Raman Scattering"; http://www.opticalproteomics.org/research/nanooptics.php#sers; 2 pages.

Service; "Fast, Sensitive Scan Targets Anthrax"; http://www.sciencemag.org/cgi/content/full/308/5718/45?ck=nck; vol. 308; Apr. 1, 2005; 5 pages.

Stokes, et al.; "Detection of E. coli using a microfluidics-based antibody biochip detection system"; Advanced Monitoring Development Group; Nov. 13, 2000; 7 pages.

Taurozzi; "Sers-Active Silver Nanoparticle Arrays on Track Etch Membrane Support as Flow-through Water Quality Sensors"; http://aiche.confex.com/aiche/2006/techprogram/P59895.HTM; Nov. 15, 2006; 3 pages.

Tay; "Applications of Enhanced Raman Spectroscopy i Biological Sciences"; Institute for Microstructural Sciences; 2005; 12 pages.

Vo-Dinh; "Biosensors, Nanosensors and Biochips: Frontiers in Environmental and Medical Diagnostics"; Oak Ridge National Laboratory; The 1st International Symposium on Micro & Nano Technology; Mar. 2004; 6 pages.

Vo-Dinh, et al.; "Surface-enhanced Raman Scattering (SERS) Method and Instrumentation for Genomics and Biomedical Analysis"; Journal of Raman Spectroscopy; 1999; 9 pages.

Vo-Dinh, et al.; "Cancer gene detection using surface-enhanced Raman scattering (SERS)"; Journal of Raman Spectroscopy; Mar. 13, 2002; 6 pages.

Yakes, et al.; "Detection of *Mycobacterium avium* subsp. paratuberculosis by a Sonicate Immunoassay Based on Surface-Enhanced Raman Scattering"; Clinical and Vaccine Immunology; vol. 15; Feb. 2008; 8 pages.

Aizpurua, et al; "Optical Properties of Coupled Metallic Nanorods for Field-enhanced Spectroscopy"; The American Physical Society; 2005; 13 pages.

Chaney, et al; "Aligned Silver Nanorod Arrays Produce High Sensitivity Surface-enhanced Raman Spectroscopy Substrates"; American Institute of Physics; 2005; 3 pages.

Coldiron, et al; "Nanotechnology in Cancer"; http://www.concana.com/Nanotechnology.htm; Copyright 2007-2008; 5 pages.

Faulds, et al; "Evaluation of Surface-enhanced Resonance Raman Scattering for Quantitative DNA Analysis"; http://www.nano-biology.net/showabstract.php?mid=14719891; 2004; 1 page.

Gu, et al; "Optimum Length of Silver Nanorods for Fabrication of Hot Spots"; American Chemical Society; 2007; 4 pages.

Hafner; "Plasmonics: Gold Nanoparticles are Shaped for Effect"; http://www.laserfocusworld.com/articles/article_display.html?id=252462; 2006; 4 pages.

Kim; "Surface Plasmon Resonances of Noble Metal Nanorods and Nanoparticles"; Sungkyunkwan University; May 29, 2007; 29 pages.

Murphy, et al; "Chemical Sensing and Imaging with Metallic Nanorods"; The Royal Society of Chemistry; 2008; 14 pages.

Nikoobakht, et al; "Surface-Enhanced raman Scattering Studies on Aggregated Gold Nanorods"; American Chemical Society; 2003; 7 pages.

Shuyi, et al; "An Approach to Self-Cleaning SERS Sensors by Arraying Au Nanorods on TiO2 Layer"; http://adsabs.harvard.edu/abs/2007SPIE.6647E..13L; 2007; 2 pages.

Suzuki, et al; "Physically Self-Assembled Ag nanorod Arrays for Tunable Plasmonic Sensors"; The Surface Science Society of Japan; 2005; 4 pages.

Suzuki, et al; "Vapor Phase Growth of al Whiskers Induced by Glancing Angle Deposition at High Temperature"; American Institute of Physics; 2006; 3 pages.

Uechi, et al; "Phtochemical and Analytical Applications of Gold Nanoparticles and Nanorods Utilizing Surface Plasmon Resonance"; Anal Bioanal Chem; 2008; 11 pages.

Yao, et al; "A Complementary Study of Surface-enhanced Raman Scattering and Metal Nanorod Arrays"; Pure Appl. Chem, vol. 72; 2000; 8 pages.

Yao, et al; "Electronic Properties of Metal Nanorods Probed by Surface-enhanced Raman Spectroscopy"; Chem. Commun.; The Royal Society of Chemistry; 2000; 2 pages.

* cited by examiner

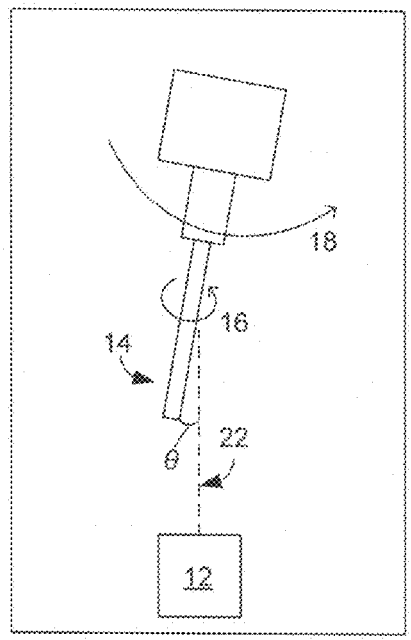
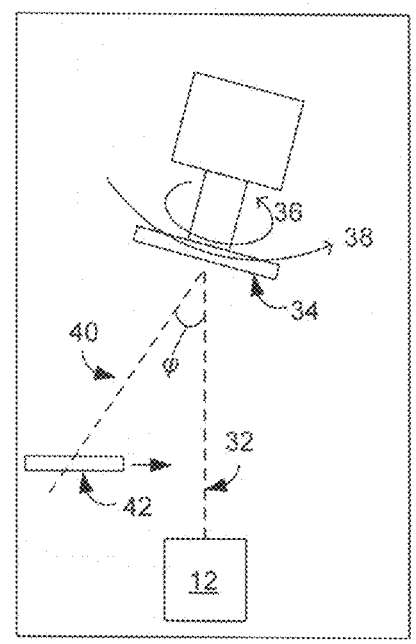
FIG. 1A
FIG. 1B
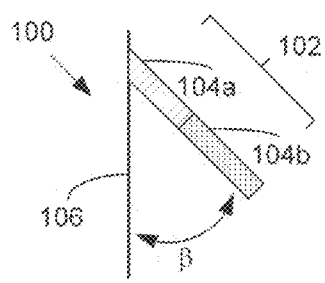
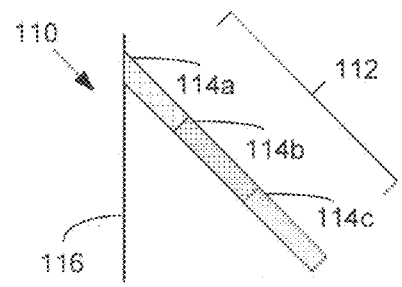
FIG. 2A
FIG. 2B

FIGURE 8
A
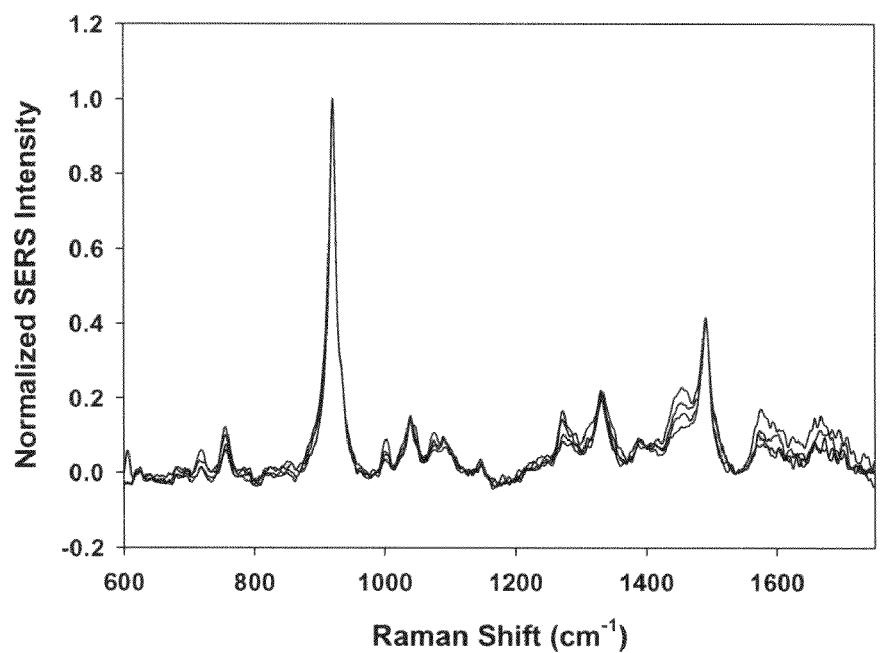
B
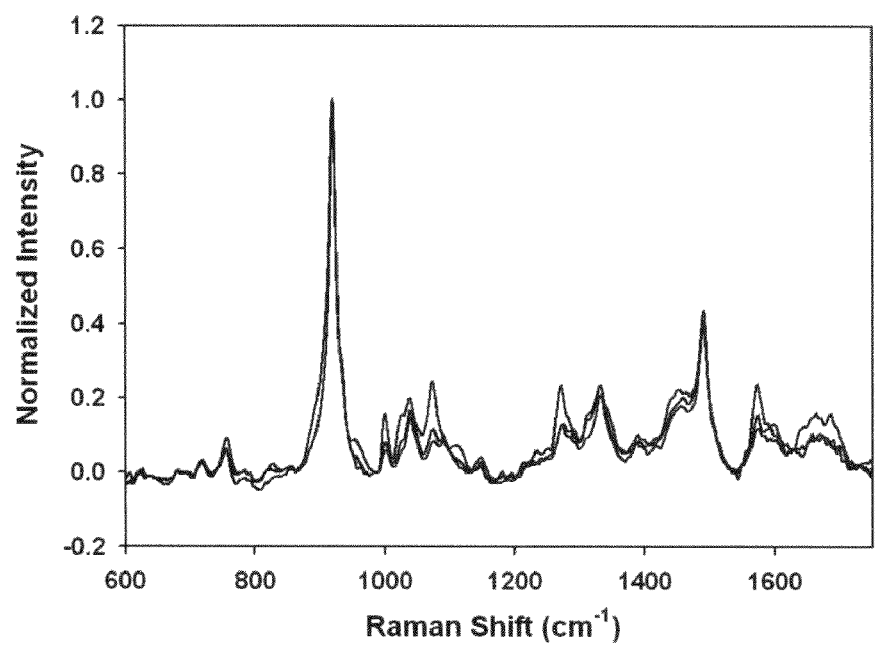

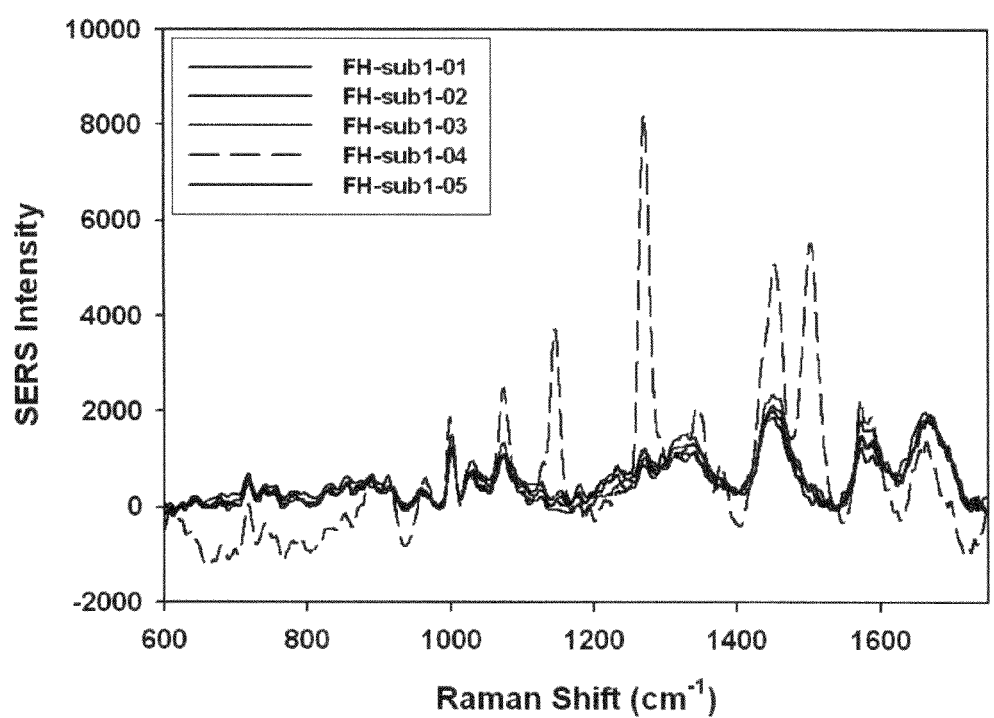

| PC | RV4 | WA | RV5 | S2 | RV3 | YO | ST-3 | F45 |
|----|-----|-----|-----|-----|-----|-----|------|-----|
| 2 | + | - | - | - | +/- | - | - | + |
| 3 | +/- | +/- | + | - | - | +/- | - | +/- |
| 4 | - | - | +/- | +/- | +/- | + | - | +/- |
| 5 | + | +/- | + | +/- | - | + | - | - |
| 6 | +/- | +/- | +/- | +/- | +/- | +/- | +/- | +/- |
| 7 | +/- | +/- | - | + | - | + | +/- | +/- |

| Strain | Class ID | # samples | # correct | Also classified as |
|--------|----------|-----------|-----------|--------------------|
| RV4    | 2        | 6         | 5         | 5(1)               |
| WA     | 3        | 6         | 4         | ST-3(2)            |
| RV5    | 4        | 6         | 5         | F45(1)             |
| S2     | 7        | 6         | 4         | WA(2)              |
| RV3    | 7        | 6         | 5         | WA(1)              |
| YO     | 8        | 6         | 6         |                    |
| ST-3   | 1        | 6         | 4         | 5(1), WA(1)        |
| F45    | 6        | 6         | 6         |                    |

FIG. 19

PLS-DA of Mpn strains in Methanol

This is a model of type: PLSDA
Developed 03-Mar-2008 11:45:1.21
X-block: METHANOL_MPN_MARCH1_2008_SG_UVN_0x2DMEOH_MATLAB 45 by 1484
Included: [ 1-45 ] [ 1-1484 ]
Preprocessing: Autoscale
Y-block: meoh0x2D 45 by 3
Included: [ 1-45 ] [ 1-3 ]
Preprocessing: Autoscale
Num. LVs: 4
Cross validation: venetian blinds w/ 4 splits Statistics for each y-block column:

| Modeled Class: | FH | II3 | M129 |
|---|---|---|---|
| Sensitivity (Cal): | 1.000 | 1.000 | 1.000 |
| Specificity (Cal): | 1.000 | 1.000 | 1.000 |
| Sensitivity (CV): | 1.000 | 0.933 | 1.000 |
| Specificity (CV): | 1.000 | 1.000 | 1.000 |
| Class. Err (Cal): | 0 | 0 | 0 |
| Class. Err (CV): | 0 | 0.0333333 | 0 |
| RMSEC: | 0.0874568 | 0.0660081 | 0.0431763 |

Percent Variance Captured by Regression Model

| | -----X-Block----- | | -----Y-Block----- | |
|---|---|---|---|---|
| Comp | This | Total | This | Total |
| 1 | 40.22 | 40.22 | 47.51 | 47.51 |
| 2 | 7.49 | 47.70 | 38.09 | 85.60 |
| 3 | 7.30 | 55.00 | 9.90 | 95.50 |
| 4 | 2.05 | 57.05 | 2.42 | 97.92 |

FIG. 25

PLS-DA of Mpn dilutions in Methanol

- Num. LVs: 9
- Cross validation: leave one out
- Statistics for each y-block column:
- Modeled Class:    FH            II3            M129
- Sensitivity (Cal): 0.979       1.000       0.980
- Specificity (Cal): 0.978       0.969       0.977
- Sensitivity (CV): 0.979        0.975       0.940
- Specificity (CV): 0.978        0.959       0.943
- Class. Err (Cal): 0.0215278  0.0153061  0.0213636
- Class. Err (CV): 0.0215278  0.0329082  0.0584091
- RMSEC:          0.186155    0.200551    0.205117

Fig. 26

PLSDA_Mpn strains in 3 preps

This is a model of type: PLSDA
Developed 08-Apr-2008 12:25:21.53
X-block: SEMSamples_3preps_sg9_uvn_matlab  120 by 1483
Included: [ 1-120 ] [ 1-1483 ]
Preprocessing: Mean Center
Y-block: x3Prep_yblock  120 by 3
Included: [ 1-120 ] [ 1-3 ]
Preprocessing: Autoscale
Num. LVs: 10
Cross validation: leave one out Statistics for each y-block column:

| Modeled Class: | FH | II3 | M129 |
|---|---|---|---|
| Sensitivity (Cal): | 0.975 | 1.000 | 0.927 |
| Specificity (Cal): | 0.988 | 0.951 | 0.987 |
| Sensitivity (CV): | 0.925 | 0.974 | 0.927 |
| Specificity (CV): | 0.975 | 0.951 | 0.962 |
| Class. Err (Cal): | 0.01875 | 0.0246914 | 0.0429145 |
| Class. Err (CV): | 0.05 | 0.0375119 | 0.0555727 |
| RMSEC: | 0.154833 | 0.21468 | 0.216367 |

| | -----X-Block----- | | -----Y-Block----- | |
|---|---|---|---|---|
| Comp | This | Total | This | Total |
| 1 | 36.17 | 36.17 | 12.55 | 12.55 |
| 2 | 18.84 | 55.01 | 16.59 | 29.14 |
| 3 | 13.61 | 68.62 | 11.84 | 40.98 |
| 4 | 8.30 | 76.92 | 13.20 | 54.18 |
| 5 | 8.74 | 85.66 | 6.60 | 60.78 |
| 6 | 2.00 | 87.66 | 4.04 | 64.82 |
| 7 | 0.94 | 88.60 | 6.00 | 70.81 |
| 8 | 0.89 | 89.49 | 4.60 | 75.41 |
| 9 | 0.48 | 89.97 | 4.11 | 79.52 |
| 10 | 0.68 | 90.65 | 2.95 | 82.46 |

FIG. 27

SURFACE ENHANCED RAMAN SPECTROSCOPY (SERS) SYSTEMS FOR THE DETECTION OF BACTERIA AND METHODS OF USE THEREOF

CROSS-REFERENCE TO RELATED APPLICATION

This application is a continuation-in-part application, which claims priority to U.S. Utility Patent Application Ser. No. 11/376,661 entitled "SURFACED ENHANCED RAMAN SPECTROSCOPY (SERS) SYSTEMS, SUBSTRATES, FABRICATION THEREOF, AND METHODS OF USE THEREOF" filed on Mar. 15, 2006, now U.S. Pat. No. 7,738,096 which claims priority to U.S. patent application Ser. No. entitled, "STRUCTURES HAVING ALIGNED NANORODS AND METHODS OF MAKING," having Ser. No. 11/256,395, filed Oct. 21, 2005, which claims priority to U.S. Provisional Application entitled, "DIRECT DEPOSITION OF ALIGNED NANOROD ARRAY ONTO CYLINDRICAL OBJECTS," having Ser. No. 60/620,810, filed Oct. 21, 2004, all of which are incorporated herein by reference. U.S. Utility Patent Application Ser. No. 11/376,661 also claims priority to U.S. Provisional Applications entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/662,089, filed Mar. 15, 2005, and "SURFACE ENHANCED RAMAN SPECTROSCOPY (SERS) SYSTEMS, SUBSTRATES, FABRICATION THEREOF, AND METHODS OF USE THEREOF," having Ser. No. 60/703,110, filed Jul. 28, 2005, both of which are entirely incorporated herein by reference.

This application is a continuation-in-part application, which also claims priority to U.S. Utility patent application Ser. No. 11/495,980 entitled "SURFACE ENHANCED RAMAN SPECTROSCOPY (SERS) SYSTEMS AND METHODS OF USE THEREOF," filed on Jul. 28, 2006, now U.S. Pat. No. 7,583,379 which claims priority to U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/703,110, filed Jul. 28, 2005, both of which are entirely incorporated herein by reference.

U.S. Utility Patent Application Ser. No. 11/495,980 also claims priority to co-pending U.S. patent application entitled, "STRUCTURES HAVING ALIGNED NANORODS AND METHODS OF MAKING," having Ser. No. 11/256,395, filed Oct. 21, 2005, which claims priority to U.S. provisional application entitled, "DIRECT DEPOSITION OF ALIGNED NANOROD ARRAY ONTO CYLINDRICAL OBJECTS," having Ser. No. 60/620,810, filed Oct. 21, 2004, both of which are entirely incorporated herein by reference.

U.S. Utility patent application Ser. No. 11/495,980 also claims priority to co-pending U.S. patent application entitled, "SURFACE ENHANCED RAMAN SPECTROSCOPY (SERS) SYSTEMS, SUBSTRATES, FABRICATION THEREOF, AND METHODS OF USE THEREOF" having Ser. No. 11/376,661, filed on Mar. 15, 2006, which claims priority to U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/662,089, filed Mar. 15, 2005, both of which are entirely incorporated herein by reference.

In addition, this application claims priority to co-pending U.S. provisional application entitled "Surface Enhanced Raman Spectroscopy (SERS) Systems and Methods of Use Thereof" having ser. No. 60/944,144 filed on Jun. 15, 2007, which is entirely incorporated herein by reference.

STATEMENT REGARDING FEDERALLY SPONSORED RESEARCH OR DEVELOPMENT

This invention was made with government support under ECS-0304340 awarded by the National Science Foundation and under EB001956 awarded by the National Institutes of Health. The U.S. government has certain rights in the invention(s).

FIELD OF THE DISCLOSURE

The present disclosure is generally directed to surface-enhanced Raman spectroscopic (SERS) systems and methods for detection of analytes, in particular, the detection of biomolecules using nanostructures, particularly nanorods. The present disclosure is further directed to SERS systems and methods for detection of a biomolecule of interest, such as a bacterium, virus, or other infectious agent.

BACKGROUND

The discovery of single-molecule and single-nanoparticle surface-enhanced Raman scattering (SERS) has attracted considerable interest, both for fundamental studies of enhancement mechanisms and for potential applications in ultra sensitive optical detection and spectroscopy. A number of researchers have shown that the enhancement factors are as large as $10^{14}$-$10^{15}$, leading to Raman scattering cross sections that are comparable to or even larger than those of fluorescent organic dyes. This enormous enhancement allows spectroscopic detection and identification of single molecules located on the surface of single nanoparticles or at the junction of two particles at room temperature. Progress has been made concerning both the structural and mechanistic aspects of single-molecule SERS, but it is still unclear how this large enhancement effect might be exploited for applications in analytical chemistry, molecular biology, or medical diagnostics. One major problem is the intrinsic interfacial nature of SERS, which requires the molecules to adsorb on roughened metal surfaces. For biological molecules such as peptides, proteins, and nucleic acids, surface-enhanced Raman data are especially difficult to obtain, hard to interpret, and nearly impossible to reproduce. Therefore, a need in the industry exists to improve SERS data for biological molecules.

Various bacteria are responsible for numerous human diseases. For example, *Escherichia coli* can cause several intestinal and extra-intestinal infections such as urinary tract infections, meningitis, peritonitis, mastitis, septicemia and Gram-negative pneumonia. In addition, a bacterial infection from *Mycoplasma pneumoniae*, may lead to tracheobronchitis, primary atypical pneumonia, contribute to the onset and exacerbation of asthma, and other respiratory disorders. Furthermore, an infection from *Mycoplasma genitalium* may lead to urogenital disease. Bacterial infections, such as these noted above, are the cause of millions of hospitalizations and thousands of deaths each year. Current detection and diagnostic methods for many bacterial pathogens are not sensitive enough for early and rapid detection. Thus, improved systems and methods for the detection of pathogens and other biomolecules are needed.

Members of the Order Mycoplasmatales contribute to a variety of health, economic and research issues. Specifically, *Mycoplasma pneumoniae* (Mpn) is a human pathogen that is known to cause atypical pneumonia and tracheobronchitis and has been implicated in a variety of chronic conditions ranging from asthma and arthritis to activation of AIDS infections and transformation of cells to a cancerous state. Alternatively, *Mycoplasma gallisepticum* (MG) causes severe chronic respiratory disease in chickens and turkeys resulting in $572 million dollars in annual losses to the poultry industry in the US alone. Therefore, efforts to detect the organisms have progressed from culture methods, to biochemical tests, to molecular approaches such as PCR and ELISA. Each approach is limited by either a lack of sensitivity, labor or time intensive preparations, or a confounding level of false positives that stimulate the search for improved detection approaches. The use of Raman Spectroscopy, attractive as a detection method due to the promise of high sensitivity and minimal sample preparation as well as whole organism fingerprinting, has not been exploited due to an inherently weak signal. However, the fabrication of nanorod array substrates allows enhancement of the signal to measureable levels with reproducibility that now makes this viable as a biosensing platform.

Various viruses are responsible for many common human diseases, such as colds, flu, diarrhea, chicken pox, measles, and mumps. Some viral diseases such as rabies, hemorrhagic fevers, encephalitis, polio, yellow fever, and acquired immunodeficiency syndrome (AIDS), can result in death. In addition, Rotavirus is the most common cause of acute gastroenteritis among children, resulting in the hospitalization of approximately 55,000 children each year in the United States and the death of over 600,000 children annually worldwide.

The current state-of-the-art for viral diagnostic methods involves isolation and cultivation of viruses and may employ (1) an enzyme-linked immunosorbant assay (ELISA), a method that uses antibodies linked to an enzyme whose activity can be used for quantitative determination of the antigen with which it reacts, or (2) polymerase chain reaction (PCR), a method of amplifying fragments of genetic material so that they can be detected. These diagnostic methods are cumbersome, time-consuming, and ELISA has limited sensitivity.

There is, therefore, a critical need for a rapid, reproducible and highly sensitive and specific method of diagnosing viruses such as Respiratory Syncytial Virus (RSV) that inflict substantial disease burdens on human and animal health and (not insignificantly) for other respiratory viruses that also pose a significant threat as agents for bioterrorism. The emergence of biosensing strategies that leverage nanotechnology for direct, rapid, and increased sensitivity in detection of viruses, are needed to bridge the gap between the unacceptably low sensitivity levels of current bioassays and the burgeoning need for more rapid and sensitive detection of infectious agents.

SUMMARY

SERS systems and methods for detecting an analyte of interest, particularly a biomolecule (e.g., bacteria, virus, and the like) of interest are disclosed.

Briefly described, a representative embodiment of a method of detecting at least one bacterium in a sample, among others, includes: exposing a substrate having an array of nanorods on the substrate to the sample including at least one of a first bacterium and a second bacterium; and measuring a surface enhanced Raman spectroscopy (SERS) spectrum, wherein a SERS spectrum of the array of nanorods and first bacterium is detectably different than a SERS spectrum of the array of nanorods and the second bacterium.

Briefly described, a representative embodiment of a method of detecting different strains of bacteria, in a sample, among others, include exposing a substrate having an array of nanorods on the substrate to the sample including at least one of a first strain of bacteria and a second strain of that same bacteria; and measuring a surface enhanced Raman spectroscopy (SERS) spectrum, wherein a SERS spectrum of the array of nanorods and first strain of the bacteria is detectably different than a SERS spectrum of the array of nanorods and the second strain of the bacteria.

Briefly described, a representative embodiment of a method of detecting at least one virus, in a sample, among others, include exposing a substrate having an array of nanorods on the substrate to the sample including at least one of a first Rotavirus and a second Rotavirus; and measuring a surface enhanced Raman spectroscopy (SERS) spectrum, wherein a SERS spectrum of the array of nanorods and first Rotavirus is detectably different than a SERS spectrum of the array of nanorods and the second Rotavirus.

Briefly described, a representative embodiment of a method of detecting different strains of the same virus, in a sample, among others, include exposing a substrate having an array of nanorods on the substrate to the sample including at least one of a first strain of Rotavirus and a second strain of Rotavirus; and measuring a surface enhanced Raman spectroscopy (SERS) spectrum, wherein a SERS spectrum of the array of nanorods and first Rotavirus virus strain is detectably different than a SERS spectrum of the array of nanorods and the second Rotavirus virus strain.

Briefly described, a representative embodiment of a method of detecting at least one biomolecule in a sample, among others, includes: attaching at least one first biomolecule to an array of nanorods on a substrate; exposing the substrate including the first biomolecule to the sample containing at least one of a second biomolecule and a third biomolecule; and measuring a surface enhanced Raman spectroscopy (SERS) spectrum, wherein a SERS spectrum of the array of nanorods and the first biomolecule is detectably different than a SERS spectrum of the array of nanorods, the first biomolecule, and the second biomolecule and a SERS spectrum of the array of nanorods, the first biomolecule, and the third biomolecule, and wherein the SERS spectrum of the array of nanorods, the first biomolecule, and the second biomolecule is detectably different than the SERS spectrum of the array of nanorods, the first biomolecule, and the third biomolecule.

Other aspects, compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 1 illustrates embodiments of modified oblique angle deposition (OAD) systems for a non-planar substrate (1A) and a planar substrate (1B).

FIGS. 2A through 2E illustrate exemplary schematic representations of various combinations and shapes of nanostructures on SERS substrates.

FIGS. 8A through 8B illustrate normalized SERS response for *M. pneumoniae* strain M 129. In particular, FIG. 8A illustrates M 129 collected from five different locations on the same substrate. Similarly, FIG. 8B displays the average SERS spectra for M129 collected from three different substrates.

FIG. 10A illustrates PC 2 vs PC1 and FIG. 10B illustrates PC 5 vs PC 1. The PCA model was constructed using the spectral range from 600-1750 $cm^{-1}$. Suspected outlying spectra are circled in orange. For all plots, the symbols denote the strain of *Mycoplasma* used: n M129 I FH, g II-3. The t symbol denotes the PCA scores for a blank water background.

FIG. 11 illustrates the spectra collected for the FH strain of *M. pneumoniae* from substrate one. Dashed plot is a spectrum for FH that resulted in an outlier in the scores plots in FIG. 10A.

FIG. 12A illustrates PC 2 vs PC 1 and FIG. 12B illustrates PC 8 vs PC1. The PCA model was constructed using the spectral range from 600-1750 $cm^{-1}$. For all plots, the symbols denote the strain of *Mycoplasma* used: n M129, I FH, g II-3. The t symbol denotes the PCA scores for a blank water background.

FIGS. 17A through 17D illustrate PCA scores plots and tabulated results for the Rotavirus strains. FIG. 17A illustrates PC 2 vs PC 1, FIG. 17B illustrates PC 3 vs PC 1, and FIG. 17C illustrates PC 4 vs PC 1. The PCA model was constructed using a total of 7 PCs accounting for 99.49% of the total variance for the spectral range from 600-1750 $cm^{-1}$. FIG. 17D illustrates signs of the score values for each PC of each strain.

FIG. 18 displays the results of K-Means Cluster Analysis of the SERS spectra for the samples.

FIG. 19 illustrates a schematic of an experimental design, as described in Example 4.

FIG. 25 is a table that illustrates partial least squares discriminatory analysis (PLS-DA) of three strains of Mpn in methanol. 57% of the variance was used to create this model.

FIG. 26 is a table that illustrates PLS-DA of dilutions 1:100, 1:10,000 and 1:1,000,000 of three strains of Mpn.

FIG. 27 is a table that illustrates partial least squares (PLS-DA) of three strains of *Mycoplasma pneumoniae* in three different fixatives.

DETAILED DESCRIPTION

Figure 2C:
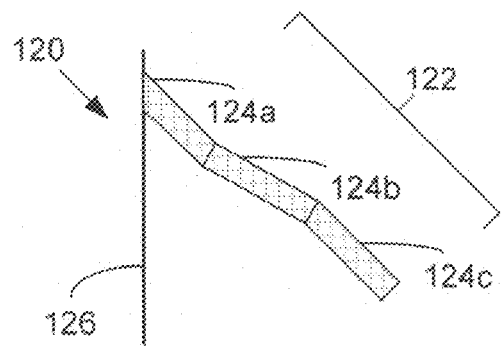

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

Use of the phrase "biomolecule" is intended to encompass deoxyribonucleic acid (DNA), ribonucleic acid (RNA), nucleotides, oligonucleotides, nucleosides, proteins, peptides, polypeptides, selenoproteins, antibodies, protein complexes, combinations thereof, and the like. In particular, the biomolecule can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, microorganisms such as viruses, bacteria, protozoa, archaea, fungi, algae, spores, apicomplexan, trematodes, nematodes, mycoplasma, or combinations thereof.

The biomolecule may be a virus, including, but not limited to, RNA and DNA viruses. In particular the biomolecule is a virus, which may include, but is not limited to, negative-sense and positive-sense RNA viruses and single stranded (ss) and double stranded (ds) DNA viruses. The ds group I DNA viruses include the following families: Adenoviridae, Herpesviridae, Papillomaviridae, Polyomaviridae, Poxyiridae, and Rudiviridae. The group II ssDNA viruses include the following families: Microviridae, Geminiviridae, Circoviridae, Nanoviridae, and Parvoviridae. The ds group III RNA viruses include the following families: Birnaviridae and Reoviridae. The group IV postive-sense ssRNA virus familes: Arteriviridae, Coronaviridae, Astroviridae, Caliciviridae, Flaviviridae, Hepeviridae, Picornaviridae, Retroviridae and Togaviridae. The group V negative-sense ssRNA virus familes: Bornaviridae, Filoviridae, Paramyxoviridae, Rhabdoviridae, Arenaviridae, Bunyaviridae, and Orthomyxoviridae.

In particular embodiments, the biomolecule can be one of a number of strands of the virus and/or a mutated version of a virus or of one of a number of strands of a virus. In particular, the virus can include, but is not limited to, Rotavirus.

In another aspect, the biomolecule is bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio,*

*Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasli, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other Enterobacteria, *Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof.

The term biomolecule may also refer to a surface molecule or surface antigen on the surface of a pathogen (e.g., a bacterial cell), or the biomolecule is a toxin or other byproduct of a pathogen (e.g., a toxin produced by a bacterial cell). Other examples of biomolecules are viral projections such as Hemagglutinin and Neuraminidase.

Use of the phrase "peptides", "polypeptide", or "protein" is intended to encompass a protein, a glycoprotein, a polypeptide, a peptide, fragments thereof and the like, whether isolated from nature, of viral, bacterial, plant, or animal (e.g., mammalian, such as human) origin, or synthetic, and fragments thereof. Polypeptides are disclosed herein as amino acid residue sequences. Those sequences are written-left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

Use of the phrase "polynucleotide" is intended to encompass DNA and RNA, whether isolated from nature, of viral, bacterial, plant or animal (e.g., mammalian, such as human) origin, or synthetic; whether single-stranded or double-stranded; or whether including naturally or non-naturally occurring nucleotides, or chemically modified. As used herein, "polynucleotides" include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

Use of the term "affinity" can include biological interactions and/or chemical interactions. The biological interactions can include, but are not limited to, bonding or hybridization among one or more biological functional groups located on the first biomolecule and the second biomolecule. In this regard, the first (or second) biomolecule can include one or more biological functional groups that selectively interact with one or more biological functional groups of the second (or first) biomolecule. The chemical interaction can include, but is not limited to, bonding among one or more functional groups (e.g., organic and/or inorganic functional groups) located on the biomolecules.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-id antibodies to antibodies of the disclosure), and epitope-binding fragments of any of the above. In particular, antibodies include immunoglobulin molecules and immunologically active fragments of immunoglobulin molecules (i.e., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2) or subclass. The antibodies may be from any animal origin including birds and mammals (e.g., human, murine, donkey, sheep, rabbit, goat, guinea pig, camel, horse, or chicken). The antibodies may be monospecific, bispecific, trispecific, or of greater multispecificity.

Use of the term "types" with reference to bacteria is intended to include different families and/or genera of bacteria. Thus, for instance, the phrase "different types of bacteria" refers to bacteria from different genera or different families (e.g., *Mycoplasma* and *Ureaplasma*) and does not refer to different strains of bacteria of the same genus or species (e.g., *M. pneumoniae* M129 and *M. pneumoniae* FH). Use of the term "strains" with reference to bacteria may refer to different strains/species of bacteria and/or to different sub-groups of bacteria within the same strain (e.g., different strains of *M. pneumoniae* such as M129, FH, and II-3).

Use of the term "types" with reference to viruses is intended to include different families and/or genera of viruses. Thus, for instance, the phrase "different types of viruses" refers to viruses from different genera or different families (e.g., Rotavirus and influenza) and does not refer to different strains of viruses of the same genus or species (e.g., different strains of Rotavirus (e.g., RV4, WA, RV5, S2, RV3, YO, F45, and ST-3) or influenza (e.g., influenza A and influenza B). It should also be noted, that as used herein "different strains" may refer to different strains/species of virus and/or to different sub-groups of viruses within the same strain (e.g., different influenza viruses of influenza A, such as, HKX-31 (H3N2), A/WSN/33 (H1N1), and A/PR/8/34 (H1N1)).

Discussion:

In accordance with the purpose(s) of the present disclosure, as embodied and broadly described herein, embodiments of the present disclosure, in one aspect, relate to surface-enhanced Raman spectroscopic (SERS) systems and methods of using the SERS systems to detect an analyte. The present disclosure provides, in general, methods and systems for the detection, analysis, and/or quantification of a biomolecule. One aspect, among others, provides methods and systems for the detection of a biomolecule (e.g., bacteria, virus, and the like) using SERS systems including a SERS substrate including an array of nanostructures.

In particular, the SERS system of the present disclosure can be used to determine the presence, qualitatively and/or quantitatively, and distinguishing (e.g., a difference in the SERS spectra can be ascertained using methods such as, but not limited to, cluster analysis) between or among one or more types of biomolecules, cells, toxins, drugs, viruses (e.g., different types, different strains of the same type, differences within strands of the same type, and the like), bacteria, explosives, nuclear wastes, contaminants, biohazards, and other chemical and biological compounds of interest. For clarity, this disclosure describes the use of the SERS system with biomolecules, but one skilled in the art would understand that the SERS system can be used to determine the presence, qualitatively and/or quantitatively, of other targets of interest such as those described above, to which a complimentary binding agent exists or can be designed. Embodiments of the present disclosure also relate to methods of using the SERS system to detect biomolecules in a sample. The SERS system can enhance the detection molecules (e.g., bacteria, virus, and the like) by a number of orders of magnitude (e.g., 5-12 orders of magnitude) in a reproducible manner.

Embodiments of the methods of the present disclosure provide for determining the presence, qualitatively and/or quantitatively, and distinguishing (e.g., a difference in the SERS spectra can be ascertained using methods such as, but not limited to, cluster analysis) between different types of bacteria. For example, embodiments of the present disclosure are able to distinguish among bacterium (e.g., between *E. coli* and *S. aureus*) based on at least the ratio of the Adenine and Guanine band intensities.

In an embodiment, methods of the present disclosure provide for determining the presence, qualitatively and/or quantitatively, and differentiating (e.g., a difference in the SERS spectra can be ascertained using methods such as, but not limited to, cluster analysis) between different strains of the same bacteria, such as different strains of *Mycoplasma pneumoniae* (e.g., between M129, FH, and II-3), based on the variations in band frequencies of each SERS spectrum.

As mentioned above, embodiments of the present disclosure provide SERS systems and methods for determining the presence, qualitatively and/or quantitatively, and distinguishing between different types of bacterium. In general, the SERS systems and methods of use thereof can measure SERS spectra of different bacteria. The SERS system can measure detectably different (e.g., a difference in the SERS spectra can be ascertained using methods such as, but not limited to, cluster analysis) features between the bacteria. In particular, each bacterium can have a measurable surface-enhanced Raman spectroscopic signature, where the signatures of each bacterium are distinguishable and include detectably different features.

As mentioned above, embodiments of the present disclosure provide SERS systems and methods for determining the presence, qualitatively and/or quantitatively, and distinguishing between different strains of bacterium. In general, the SERS systems and methods of use thereof can measure SERS spectra of different strains of bacteria. The SERS system can measure detectably different (e.g., a difference in the SERS spectra can be ascertained using methods such as, but not limited to, cluster analysis) features between the bacterial strains. In particular, each bacterial strain can have a measurable surface-enhanced Raman spectroscopic signature, where the signatures of each bacterial strain are distinguishable and include detectably different features.

In an embodiment, methods of the present disclosure provide for determining the presence, qualitatively and/or quantitatively, and distinguishing (e.g., a difference in the SERS spectra can be ascertained using methods such as, but not limited to, cluster analysis) between different types of viruses. In another embodiment, the methods of the present disclosure provide for determining the presence, qualitatively and/or quantitatively, and distinguishing between different strains of the same virus. In another embodiment, the methods of the present disclosure provide for determining the presence, qualitatively and/or quantitatively, and distinguishing between the same strands of the same virus, where one or both strands include a mutation. In another embodiment, the methods of the present disclosure provide for determining the presence, qualitatively and/or quantitatively, and distinguishing between different portions of the same strands of the same virus (e.g., differences in a conserved gene region). A cluster analysis can be used to distinguish between various virus spectra in each of the embodiments described above and in the Examples.

In an embodiment, methods of the present disclosure provide for determining the presence, qualitatively and/or quantitatively, and differentiating (e.g. a difference in the SERS spectra and can be further defined using chemometric methods such as, but not limited to, exploratory data analysis (EDA) including principal component analysis (PCA) and K-means clustering algorithm analysis) between different strains of the same virus as previously described (Kramer, R. *Chemometric Techniques for Quantitative Analysis*; Marcel Dekker: New York, 1998, which is incorporated by reference for the corresponding discussion).

In an embodiment, methods of the present disclosure provide for determining the presence, qualitatively and/or quantitatively, and differentiating (e.g., a difference in the SERS spectra can be ascertained using methods such as, but not limited to, cluster analysis) between different strains of the same virus, such as different strains of Rotavirus (e.g., between RV4, WA, RV5, S2, RV3, YO, F45, and ST-3), based on the variations in band frequencies of each SERS spectrum.

In general, the SERS system includes an array of nanostructures on a substrate. In embodiments, the nanostructure can be a nanorod. In an exemplary embodiment, the nanostructure is functionalized with one or more binding agent(s) capable of binding (e.g., ionically, covalently, hydrogen binding, and the like) or otherwise associating (e.g., chemically, biologically, etc.) with one or more analytes (e.g., biomolecule(s)) of interest.

The nanostructures can include, but are not limited to, nanorods, nanowires, nanotubes, nanospirals, combinations thereof, and the like, and uniform arrays of each. The nanostructures (e.g., nanorods) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound (organic or inorganic compound) including a metal, a metal oxide, a metal nitride, a metal oxynitride, a metal carbide, a doped material), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof. In particular the materials can include one or more of the following: silver, gold, nickel, silicon, germanium, silicon oxide, and titanium oxide. The composition of the nanorods is the same as that of the materials described herein or a combination of the materials described herein, or alternative layers of each.

In an embodiment of the SERS substrate of the present disclosure, the nanostructure is a nanorod. In particular embodiments, the nanorod is formed in a uniform and aligned array on the substrate. The nanorod can have the dimensions and characteristics as described below. In particular, the nanorods (e.g., silver, nickel, silicon, and titanium oxide) are disposed on a planar substrate, such a glass or silicon slide or disk, or a non-planar substrate, such as an optical fiber, or other cylindrically symmetric substrates.

A method of making a SERS substrate of the present disclosure includes providing a substrate and depositing the nanorods on the substrate by a modified oblique angle deposition (OAD) technique/system or glancing angle deposition (GLAD). In an embodiment of a modified OAD technique, the OAD system can include a two-axis substrate motion apparatus in a physical vapor deposition (PVD) system (e.g., thermal evaporation, e-beam evaporation, sputtering growth, pulsed laser deposition, and the like) that operates at temperatures lower than the melting point of the material used to form the nanostructures. In an embodiment, the substrate motion system provides two rotation movements: one is the polar rotation, which changes angle between the substrate surface normal and the vapor source direction, and one is the azimuthal rotation, where the sample rotates about its center axis of rotation (e.g., normal principle axis). In some embodiments, the nanorods are disposed on a thin film (e.g., silver, nickel, silicon, and titanium oxide) or a multilayer thin film (e.g., layers of silver, nickel, silicon, and titanium oxide, composites thereof, and nitrides thereof) that is deposited onto those substrates prior to nanorod deposition.

At least one advantage of using the OAD system is that the nanostructures (e.g., nanorods) can be formed at temperatures compatible with substrates such as, but not limited to, optical fibers, waveguides, and the like. This is in contrast to other techniques that operate under conditions (e.g., high temperatures) that are not compatible with many substrates of interest. Another advantage of using the OAD system is that catalysts are not needed to form the nanostructures, in contrast to currently used technologies. Since a vacuum system is used, the purity of the nanorods is very high, and the vacuum system is compatible with conventional microfabrication processes.

In some embodiments, the substrate is a planar (or flat) substrate, such as a silicon, quartz, or glass substrate. Planar substrates may also be made of materials including, but not limited to, semiconductors (e.g., Si, GaAs, GaAsP, and Ge), oxides (e.g., $SiO_2$, $Al_2O_3$), and polymers (e.g., polystyrene, polyacetylene, polyethylene, etc.). In other embodiments the substrate is a non-planar substrate such as a cylindrical or conical substrate (e.g., an optical fiber or pipette tip). The substrates can also be microfabricated or nanofabricated substrates, such as substrates with a regular array of micropatterns, such as a dot array, line array, or well array, or similar nanopatterns.

FIG. 1 illustrates an embodiment of an OAD system for a planar substrate 30 (FIG. 1B) and an embodiment of an OAD system for a non-planar substrate 10 (FIG. 1A). The OAD systems 10 and 30 include, but are not limited to, an evaporation source 12, a substrate 14 or 34, and a substrate manipulation mechanism (e.g., one or more motors) to move (e.g., rotate) the substrate relative to the evaporation source 12. A motor of the OAD system 10 can move the non-planar substrate 14 in a polar rotation 18, which changes the incident angle ($\theta$) between the substrate rotating axis (e.g., center axis of rotation) and the vapor source direction (e.g., vapor arrival line 22). The OAD system 30 for the planar substrate 34 also includes a motor for moving the planar substrate 34 in a polar rotation 38, which changes the incident angle ($\phi$) between the surface normal axis of the substrate (e.g., axis 40) and the vapor source direction (e.g., vapor arrival line 32).

Another motor of the OAD system 10 can move the substrate in an azimuthal rotation 16, where the sample rotates about its center axis of rotation (normal principle axis) to allow deposition of nanorods around the entire surface of the non-planar substrate 14. In the case of a planar substrate 34, while azimuthal rotation of the substrate is not required for deposition of the nanorods, the OAD system 30 may optionally include a second motor for rotating the planar substrate in an azimuthal rotation 36, which allows additional control over the shape of the nanorods. For both planar and non-planar substrates, varying the incident angles $\theta$ and $\phi$ and the rate and pattern of azimuthal rotation can result in various shapes, sizes, and/or distribution of nanorods on the substrate surface. The OAD systems 10 and 30 can also include appropriate vacuum pumps and electronic control equipment as are known in the art. Additional details regarding the OAD systems are described in the Examples below.

Embodiments of the OAD systems 10 and 30 can include a physical vapor deposition (PVD) system, such as thermal evaporation, e-beam evaporation, molecular beam epitaxy (MBE), sputtering growth, pulsed laser deposition, combinations thereof, and the like. In this embodiment, the PVD is a thermal evaporation source 12, where a material can be heated to an appropriate temperature to evaporate the material. The heating temperature depends primarily on the properties of the material to be deposited, but may also depend, at least in part, on the substrate 14 or 34, and other conditions in the OAD system. Typically, the temperature is less than the melting point (e.g., less than one-third of the melting point) of the material being evaporated.

In an alternative embodiment, the system can be adapted to include a Chemical Vapor Deposition (CVD) or a Plasma-Enhanced Chemical Vapor Deposition (PECVD) system. In such systems an appropriate molecular precursor is evaporated at the source and undergoes decomposition at the surface of the substrate 14 or 34. The decomposition leads to the deposition of a material of interest onto the substrate 14 or 34 with concomitant elimination of molecular fragments, which can be easily purged from the system. CVD and PECVD allow for the single-step deposition of unitary—(e.g., metals), binary—(e.g., alloys, oxides, carbides), ternary—(e.g., $(Si,Ge)O_4$), and higher other compounds.

Modification of the system for use in conjunction with CVD and PECVD deposition techniques can be inferred from standard CVD and PECVD systems described in the art (e.g., D. M. Dobkin, M. K. Zuraw, *Principles of Chemical Vapor Deposition*, (2003) Springer, N.Y.; Srinivasan Sivaram, *Chemical Vapor Deposition: Thermal and plasma deposition of electronic materials (Electrical Engineering)*, (1995), Springer N.Y., all of which are incorporated by reference for the corresponding discussion).

The OAD systems can operate at a substrate temperature less than the melting point of the material being evaporated. In particular, the substrates of the OAD systems can operate at or near room temperature, be cooled to liquid nitrogen temperature, or be heated to a temperature of about ⅓ of the melting temperature of the material being evaporated. Thus, substrates having a relatively low melting point (e.g., plastics such as those used in fiber optics) can be used, unlike other high temperature techniques. The OAD systems can operate at a pressure where the mean free path of the gas in the chamber during deposition is comparable or larger than the source-substrate distance.

The substrate 14 and/or 34 can be mounted or otherwise attached to an arm or other component in communication with the motors that move the substrate. In one embodiment, to deposit nanostructures (e.g., nanorods) onto a non-planar substrate 14, the substrate 14 is slightly rotated polarly in order to make an angle θ less than about 15° (e.g., θ less than about 12°, θ less than about 10°, θ less than about 8°, and θ less than about 5°; and where θ is from about 0, about 0 to 12°, about 0 to 10°, about 0 to 8°, and about 0 to 5°), with respect to the incoming vapor direction. Then, the source material is evaporated at a constant rate (e.g., the rate is about 0.1 nm/sec to 0.3 nm/sec, about 0.1 nm/sec to 0.6 nm/sec, about 0.1 nm/sec to 1 nm/sec, about 0.1 nm/sec to 1.5 nm/sec, and about 0.1 nm/sec to 2 nm/sec), or a substantially constant rate, in the evaporation source 12, while the substrate 14 is rotated with a constant speed azimuthally (e.g., the speed is about 0.01 rev/sec to 0.05 rev/sec, about 0.01 rev/sec to 0.1 rev/sec, about 0.01 rev/sec to 0.2 rev/sec, and about 0.01 rev/sec to 0.4 rev/sec). The nanostructures of the evaporated material are thereby deposited (e.g., uniformly deposited) onto the sidewall (e.g., the inner and/or outer sidewall or selected portions thereof) of the substrate.

Such non-planar substrates are symmetrical about one center axis of rotation. The non-planar surface can be an inside surface and/or an outside surface of the substrate. The non-planar surface can include, but is not limited to, a cylindrical surface, a tapered surface, a conical surface, a tapered cylindrical surface, a cylindrical ringed substrate, and the like. The length of the substrate can be from about 1 mm to about 75 mm. The diameter of the substrate can be about 1 mm to about 75 mm. Exemplary substrates include, but are not limited to, optical fibers, waveguides, glass tubes, capillary tubes, metallic rods/tubes, and the like. Methods of forming nanostrucutre arrays on non-planar surfaces is described in greater detail in U.S. patent application Ser. No. 11/256,395, which is incorporated by reference herein.

In another embodiment, to deposit nanostructures (e.g., nanorods) onto a planar substrate 34 (e.g., a glass microscope slide), the substrate is mounted to the OAD device 30, as shown in FIG. 1B. Depending on the size of the OAD system, the size of the substrate may vary from about 1×1 mm² to about 30×30 cm². In some embodiments, it is preferable to deposit one or more thin film base layers of material (such as the materials described above for forming the nanostructures) on the substrate. This can be accomplished by first positioning the substrate at a normal incidence (e.g., φ=0°) to the evaporation source (e.g., where the substrate is face down to the evaporation source). A thin film base layer, or multilayer thin film base layer, may also be deposited on non-planar substrates by first positioning the substrate with the central axis of rotation perpendicular to the vapor line of arrival 22 from the evaporation source 12 (e.g., θ=90°), while continually rotating the substrate azimuthally at a constant rate of rotation. Additional details of the thin film are described below. In some embodiments the thickness of the film is from about 10 nm to about 1000 nm; in a particular embodiment it is between about 50 nm and about 500 nm. To deposit the nanorods on the planar substrate 34, the substrate is then rotated polarly in order to make an incident angle φ less than about 89° (e.g., where φ is from about 75° to 89°, about 80° to 86°, and about 86°), of the surface normal of the substrate with respect to the incoming vapor direction.

The nanorods are then deposited on the planar substrate by oblique angle vapor deposition. The source material is evaporated at a constant rate (e.g., the rate is about 0.1 nm/sec to 0.3 nm/sec, about 0.1 nm/sec to 0.6 nm/sec, about 0.1 nm/sec to 1 nm/sec, about 0.1 nm/sec to 1.5 nm/sec, and about 0.1 nm/sec to 2 nm/sec), or substantially constant rate, in the evaporation source 12, while the substrate 34 is optionally rotated azimuthally. The speed can be constant, or can vary, depending on the shape of the nanostructures desired (e.g., the speed is about 0.01 rev/sec to 0.05 rev/sec, about 0.01 rev/sec to 0.1 rev/sec, about 0.01 rev/sec to 0.2 rev/sec, and about 0.01 rev/sec to 0.4 rev/sec). The nanostructures of the evaporated material are thereby deposited (e.g., uniformly deposited) onto the surface of the substrate.

The temperature, the pressure, the deposition rate, the angle of vapor incidence, the evaporating material, and the speed and direction of the azimuthal rotation can be adjusted to control the properties of the nanostructures (e.g., the length, diameter, density, composition, and the like). Additional details regarding the process are described in the following Examples.

In some embodiments of methods of making the SERS substrates of the present disclosure, the nanorods are deposited in steps including exposing a first portion of a substrate to a metal vapor (e.g., via chemical metal vaporization) by opening a shutter 42 to a first setting. The first setting exposes a predetermined portion of the substrate. A first nanorod at a first position on the substrate is formed. The first nanorod grows to a first height (e.g., about 200 nanometers). Subsequently, the shutter is opened to a second setting, thereby exposing the first portion and a second portion to the metal vapor. A second nanorod is formed at a second position on the substrate. The second nanorod grows to the first height (e.g., about 200 nanometers). In this step the first nanorod grows to a second height (e.g., 400 nanometers), where the second height is about twice as high as the first height. This process can be repeated to expose a plurality of portions on the substrate to create a plurality of nanorods of various lengths on the substrate. For example, nanorods of the following lengths can be prepared: about 200 nanometers, about 400 nanometers, about 600 nanometers, about 800 nanometers, and about 1000 nanometers.

The length is the largest dimension of the nanostructure and is the dimension extending from the substrate (FIGS. 2A-E). The length/height of the nanorod can be from a few hundred nanometers or less to over a few thousand nanometers. In embodiments, the nanostructure can have a length of about 10 nm to 10,000 nm, about 10 nm to 5,000 nm, about 10 nm to 4,000 nm, about 10 nm to 3,000 nm, about 10 nm to 2,000 nm, about 10 nm to 1,000 nm, about 10 nm to 500 nm, about 10 nm to 250 nm, about 10 nm to 100 nm, and about 10 nm to 50 nm. In particular, the nanostructures can have a length of about 100 nm to about 1,500 nm. The length depends, at least in part, upon the deposition time, deposition rate, and the total amount of evaporating materials. The substrate can have nanorods of the same height or of varying heights on one or more portions of the substrate.

The diameter is the dimension perpendicular to the length. The diameter of the nanostructure is about 10 to 30 nm, about 10 to 60 nm, about 10 to 100 nm, about 10 to 150 nm. In particular, the nanorods can have a diameter of about 50 to 120 nm. One or more of the dimensions of the nanostructure could be controlled by the deposition conditions and the materials.

The substrate can have from tens to tens of thousands or more nanorods formed on the substrate. The array of nanostructures can be defined as having a distance of about 10 to 30 nm, about 10 to 60 nm, about 10 to 100 nm, about 10 to 150 nm, and about 10 to 200 nm, between each of the nanostructures. Alternatively, the array of nanostructures can be defined as having an average density of about 11 to 2500/$\mu m^2$. The number of nanorods, height and diameter of the nanorods, and the material that the nanorods are fabricated of will depend upon the specific application of the SERS system.

In embodiments of the SERS substrates of the present disclosure, as illustrated in FIG. 2A, the nanorods also have a tilt angle, β, formed between the nanostructure 102 and the substrate 106. The angle β, is less than 90°, particularly from about 0° to about 50°, and in preferred embodiments can be from about 5° to about 20°, from about 15° to about 30°, and from about 25° to about 40°. The conditions and the materials used to prepare the nanostructure 102 can be used to determine/select the tilt angle. The tilt angle is important in creating SERS enhancement factors with sufficient sensitivity to detect binding of an analyte of interest to the SERS sensors of the present disclosure.

It should also be noted that the nanostructure could have multiple layers of different materials or alternating materials. FIGS. 2A and 2B illustrate nanostructures (e.g., nanorods) fabricated from two and three materials, respectively. In particular, FIG. 2A illustrates a nanostructure 102 disposed on a substrate 100 having a surface 106. The nanostructure 102 includes two layers of different materials 104a and 104b. The materials can be any combination of the materials described herein. The dimensions of the nanostructure 102 can include those described herein. In another embodiment, additional layers of materials can be formed on the nanostructure 102, as shown in FIG. 2B. For example, a repeating pattern of layers 104a and 104b can be created, or three layers 114a, 114b, and 114c of a nanostructure 112 can be created (FIG. 2B).

FIG. 2C illustrates a nanostructure 122 disposed on a substrate 120 having a surface 126. The nanostructure 122 includes three layers of one or more materials 124a, 124b, and 124c, in a zigzag pattern. The dimensions of the nanostructure 122 can include those described herein. The zigzag nanostructure can be created by changing the angle periodically from $\phi_1$ to $\phi_2$ (or from $\theta_1$ to $\theta_2$, in the case of non-planar substrates) during vapor deposition to change the tilt angle β of the nanostructure being formed. The material for layers 124a, 124b, and 124c can be the same material, or can be two or more different materials.

Figure 2D:
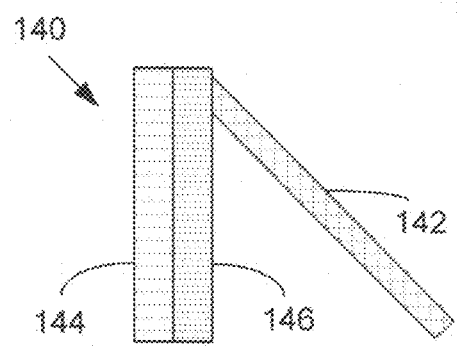

FIG. 2D illustrates a nanostructure 142 disposed on a layer 146 disposed on a substrate 140 having a surface 144. The layer 146 can be made of a materials such as those described herein for forming the nanostructures, such as, but not limited to, a metal, a metal oxide, a metal nitride, a metal oxynitride, a doped material, a polymer, a multicomponent compound, and combinations thereof. The layer 146 can have a thickness of about 10 to 50 nm, about 10 to 100 nm, about 10 to 200 nm, about 10 to 500 nm, about 10 to 800 nm, about 10 to 1000 nm, and about 10 to 2000 nm. The dimensions of the nanostructure 142 can include those described herein. The layer 146 can be made by changing the incident angle $\phi$ first to 0° (in the case of non-planar substrates, θ to 90°), depositing a uniform first layer 146 by continuous azimuthal rotation. Then, angle $\phi$ is changed to a larger angle (or angle θ is changed to a smaller angle) to deposit nanostructure 142 on top of the film 146.

Figure 2E:
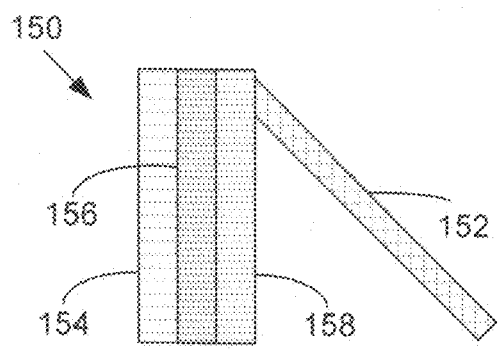

FIG. 2E illustrates a nanostructure 152 disposed on a second layer 158 disposed on a first layer 156 that is disposed on a substrate 150 having a cylindrical surface 154. The first and second layers 156 and 158 can each be made of a material, such as, but not limited to, a metal, a metal oxide, a metal nitride, a metal oxynitride, a doped material, a polymer, a multicomponent compound, and combinations thereof. The first and second layers 156 and 158 can each have a thickness of about 10 to 50 nm, about 10 to 100 nm, about 10 to 200 nm, about 10 to 500 nm, about 10 to 800 nm, about 10 to 1,000 nm, and about 10 to 2,000 nm. The dimensions of the nanostructure 152 can include those described herein. The first and second layers 156 and 158 can be made by changing the incident angle $\phi$ first to 0° (in the case of non-planar substrates, θ to 90°), depositing a uniform first layer 156 by continuous azimuthal rotation, and subsequently depositing a uniform second layer 158 by continuous azimuthal rotation. Then, angle $\phi$ is changed to a larger angle (or angle θ is changed to a smaller angle) to deposit nanostructure 152 on top of the second layer 158.

Additional combinations of uniform layer(s), nanorods with layers of multiple materials, and shaped nanorods are described in U.S. patent application Ser. No. 11/256,395, which is incorporated by reference herein. The nanostructures can also be formed in various shapes by varying the incident angle $\phi$ or θ and/or varying the speed, direction, and/or pattern of azimuthal rotation as described in Y. P. Zhao, D. X. Ye, Pei I. Wang, G. C. Wang, and T. M. Lu, "*Fabrication Si nano-columns and square springs on self-assembly colloid substrates*," International Journal of Nanoscience 1, 87 (2002); and Y.-P. Zhao, D.-X. Ye, G.-C. Wang, and T.-M. Lu, "*Designing nanostructures by glancing angle deposition*,"

SPIE Proceedings Vol. 5219, 59 (2003), which are hereby incorporated by reference herein in their entirety.

Figure 3A:
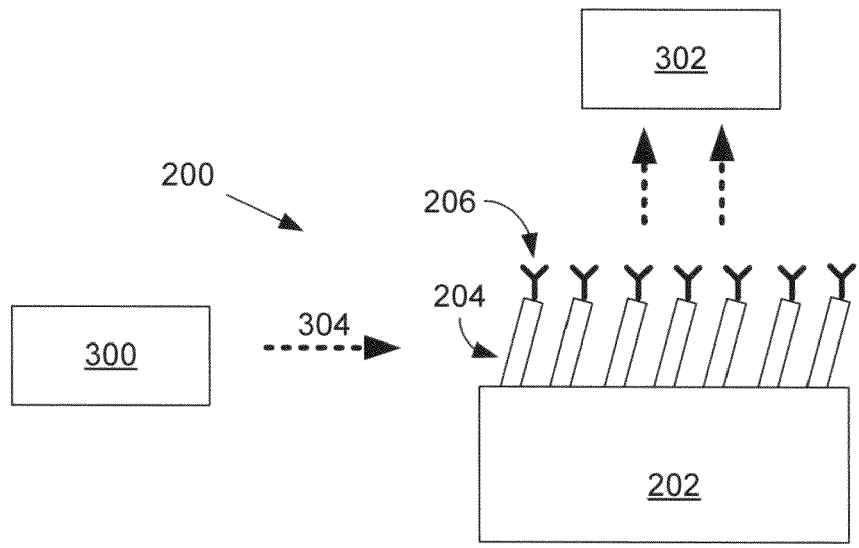
FIGS. 3A through 3B illustrate exemplary schematics of a SERS system according to the present disclosure having nanostructures deposited on the surface or portions of the surface of a substrate and a binding agent attached to the surface of the nanostructures (FIG. 3A), which is capable of binding a target analyte (FIG. 3B).

As illustrated in the SERS system 200 of FIG. 3A, once the nanorods 204 are formed on the substrate 202, a binding agent 206, such as a biomolecule, is disposed on one or more of the nanorods 204. The binding agent 206 is generally a biomolecule (as defined above), such as, a polynucleotide, polypeptide, carbohydrate, lipid, or the like. Exemplary polypeptide binding agents include, but are not limited to, antibodies or fragments thereof. The binding agent 206 can be attached/coupled to a surface of the nanostructure 204 using conventional linking chemistry (e.g., biologically (e.g., hybridization) and/or chemically (e.g., ionically or covalently)). For instance, the nanorods 204 can be functionalized by immobilizing the binding agent 206 (e.g., an antibody) on the nanorod surface by annealing to the metal (e.g., Ag or Au) surface of the nanorod via a linking agent (e.g., DSP (dithiobis(succinimidyl propionate)) or SAM (self-assembly monolayer)). Additional details regarding the disposition of the binding agent on the nanostructures are provided in the examples below.

A single type (e.g., the same polymer sequence) of binding agent 206 can be disposed or otherwise attached to the nanorods 204 on the substrate 202 (e.g., on the nanorods) or a plurality of types (e.g., two or more different polymer sequences) of binding agent can be disposed on the one or positions of the substrate.

Figure 3B:
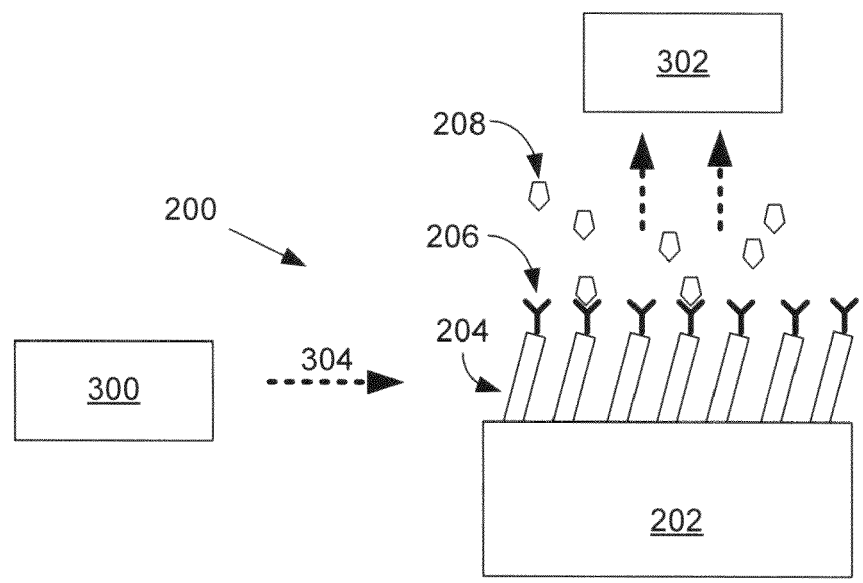

Typically, the binding agent 206, or first biomolecule, is disposed in an area of the substrate 202 having a plurality of nanorods 204. The array of nanorods 204 in combination with the first biomolecule 206 has a first measurable surface-enhanced Raman spectroscopic signature. Then, as illustrated in FIG. 3B, when an analyte of interest 208, such as a biomolecule (e.g., a second biomolecule), is introduced to the SERS system 200, the biomolecule 208 binds or otherwise interacts with the binding agent 206 bound to the nanostructure 204. Generally, the biomolecule 208 can be present or believed to be present in a sample, such as a gaseous, tissue or fluid sample. Exemplary samples include buccal cells, buffered solutions, saliva, sweat, tears, phlegm, urine, blood, plasma, cerebrospinal fluid, or combinations thereof.

The binding agent/first biomolecule 206 has an affinity for a second biomolecule 208. If the second biomolecule 208 bonds or otherwise attaches to the first biomolecule 206, the array of nanorods 204 in combination with the first biomolecule 206 and the second biomolecule 208 has a second measurable surface-enhanced Raman spectroscopic signature that is different (e.g., a statistically significant difference is enough of a difference to distinguish among the spectra, such as about 0.1%, 1%, 3%, 5%, 10%, 15%, 20%, 25%, 30%, or 40% or more difference between the spectrum of the first biomolecule and the spectrum of the second biomolecule) than the first measurable surface-enhanced Raman spectroscopic signature. Therefore, the interaction of the first biomolecule 206 and the second biomolecule 208 can be measured using the SERS system 200. Additional details regarding the detection of a second biomolecule binding event by measuring the surface-enhanced Raman spectroscopic signatures are provided in the Examples below.

Figure 3C:
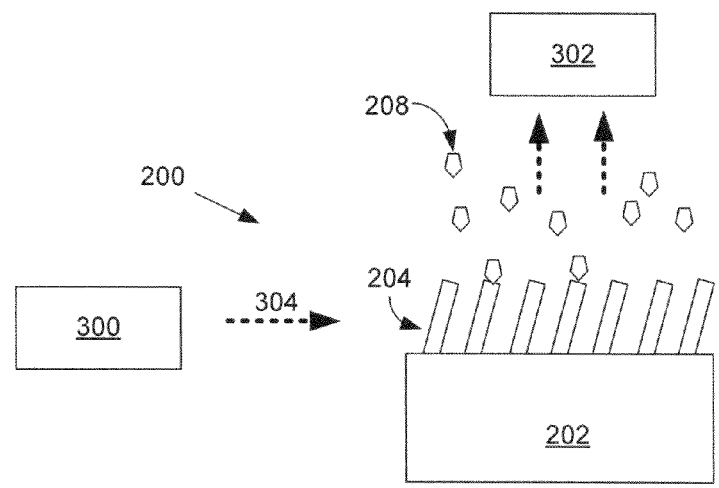
FIG. 3C is an exemplary schematic illustration of an embodiment of a SERS system according to the present disclosure having nanostructures deposited on the surface or portions of the surface of a substrate, which are capable of binding and detecting a target analyte directly, without a binding agent.

In other embodiments of the SERS system 200, as illustrated in FIG. 3C, the analyte of interest 208 (e.g., a biomolecule including, but not limited to, a virus, bacterium, or other pathogen or fragment thereof) can be disposed directly on the nanorods 204. A particular biomolecule of interest can be detected because individual biomolecules of interest have a unique SERS spectra that is detectably different, and thus distinguishable, from the SERS spectra of other biomolecules, as demonstrated in Example 4, below. For example, the SERS spectra of adenovirus is distinguishable from that of rhinovirus and HIV. Individual strains of virus can even be distinguished in this way, as demonstrated with three strains of influenza in Example 5, below. Furthermore, individual strains of *Mycoplasma pneumoniae* can also be distinguished in this manner as depicted in Example 8, FIG. 9. Thus, individual biomolecules, such as bacteria, have a unique SERS "fingerprint" that allow a particular biomolecule of interest to be distinguished from other biomolecules or background media.

Embodiments of the SERS system 200, also include an excitation source 300. The excitation source includes, but is not limited to, illumination sources such as a diode laser and an optical fiber laser, dye laser, solid state laser. In some embodiments, the excitation source 300 provides a stream of incident light 304 directed to the SERS substrate 202 to provide excitation for generating the Raman signal. In preferred embodiments the incident light 304 is perpendicular to the nanorods 204, as illustrated in FIG. 3B. The SERS system 200, also may include a data collection and analysis system, such as an optical data collection port 302 for collecting the Raman signal produced by the excitation of the SERS substrate and a system for producing the SERS spectra. Additional details regarding the excitation source and SERS data collection and analysis systems are provided in the examples below.

As mentioned above, embodiments of the present disclosure provide SERS systems and methods for determining the presence, qualitatively and/or quantitatively, and distinguishing between different types of viruses and virus strains. In general, the SERS systems and methods of use thereof can measure SERS spectra of different viruses (i.e., RNA or DNA viruses). The SERS system can measure detectably different (e.g., a difference in the SERS spectra can be ascertained using methods such as, but not limited to, cluster analysis) features between the viruses. In particular, each virus can have a measurable surface-enhanced Raman spectroscopic signature, where the signatures of each virus are distinguishable and include detectably different features.

As mentioned above, embodiments of the present disclosure provide SERS systems and methods for determining the presence, qualitatively and/or quantitatively, and for distinguishing between different nucleotide patterns and surface proteins between viruses and in virus strains. The SERS system can measure detectably different features between the different viruses based on a measurable surface-enhanced Raman spectroscopic signature, where the signature of each virus is distinguishable and includes detectably different features.

As mentioned above, embodiments of the present disclosure provide SERS systems and methods for determining the presence, qualitatively and/or quantitatively, and distinguishing between the same strands of the same virus, where one or both strands include a mutation. In general, the SERS system and methods of use thereof can measure SERS spectra of two or more nucleic acid strands of the same virus, where one or both strands include a mutation. The SERS system can measure detectably different features between the different strands of the same virus. In particular, each strand of the virus can have a measurable surface-enhanced Raman spectroscopic signature, where the signature of each strand of the virus are distinguishable and include detectably different features.

As mentioned above, the methods of the present disclosure provide for determining the presence, qualitatively and/or quantitatively, and distinguishing between different portions of the same strands of the same virus (e.g., differences in a conserved gene region). In general, the SERS system and methods of use thereof can measure SERS spectra of two or more of the same nucleic acid strands of the same virus. The SERS system can measure detectably different features between the different strands of the same virus. In particular, each strand of the virus can have a measurable surface-enhanced Raman spectroscopic signature, where the signature of each strand of the virus are distinguishable and include detectably different features.

It should be emphasized that the above-described embodiments of the present disclosure, particularly, any "preferred" embodiments, are merely possible examples of implementations, and are merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

EXAMPLES

Example 1

Sample Preparation

All of the samples were prepared using an electron beam/sputtering evaporation system (E-beam) that was custom built by Torr International. A schematic of the set-up is shown in FIG. 1A. A glass microscope slide with size 1×3" and 1 mm thick (Gold Seal®) was used as a substrate 34. A custom shutter 42 was built that could be controlled externally by a feed through, and the shutter was used to selectively reveal increasing portions of the substrate 34 during the deposition process. This method can produce one single sample with 6 different active areas. As an example, one particular sample had a 50 nm thin film deposited at normal incidence and then it was rotated to an incident angle 4 of 86°. Then nanorods were deposited in steps of 200 nm; i.e., the shutter 42 was opened partially and 200 nm was deposited, then the shutter was opened slightly more exposing more of the substrate and another 200 nm was deposited while keeping the previously exposed area still open making two sections, one with 200 nm rods and one with 400 nm. This was repeated until a total of 1000 nm was reached for the first open area. The purpose of this particular setup is to achieve an environment in which all experimental conditions are the same for each different rod length. In a conventional setup (one rod length per sample, per run), the time needed to complete the experiments would be 5 days opposed to 1 day.

The background pressure was $4.5 \times 10^{-6}$ Torr for, and the base temperature was 48.5° C. The source to substrate distance was approximately 12". The deposition was divided into two sections: the first was depositing the 50 nm thin film at a rate of 0.4 Å/s, and the second was depositing the rods at a rate of 2.0 Å/s. The schematic of the resulting film and nanorod is shown in FIG. 2D.

Figure 4:
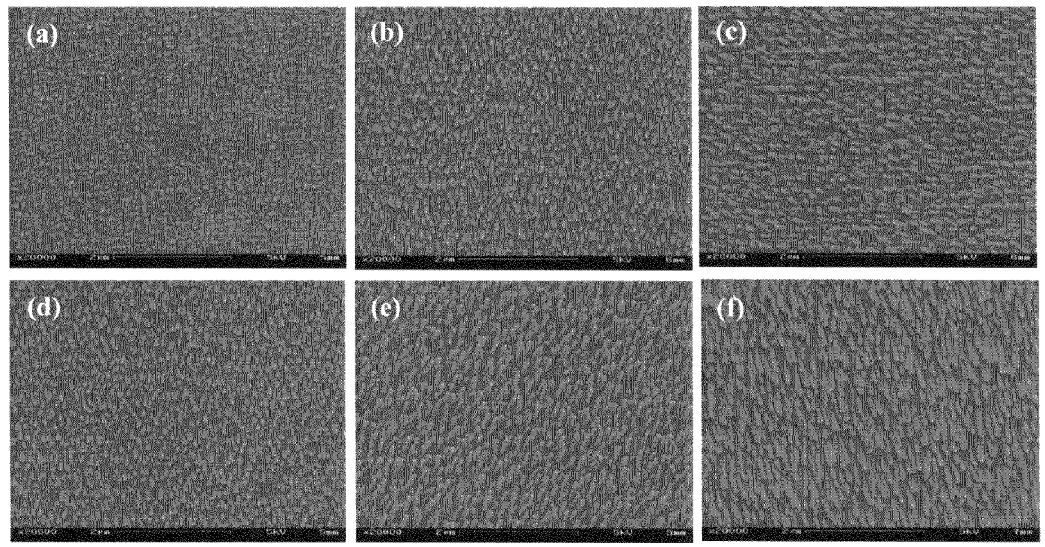
FIG. 4 illustrates SEM images of various length nanorods on a planar substrate.
Figure 5:
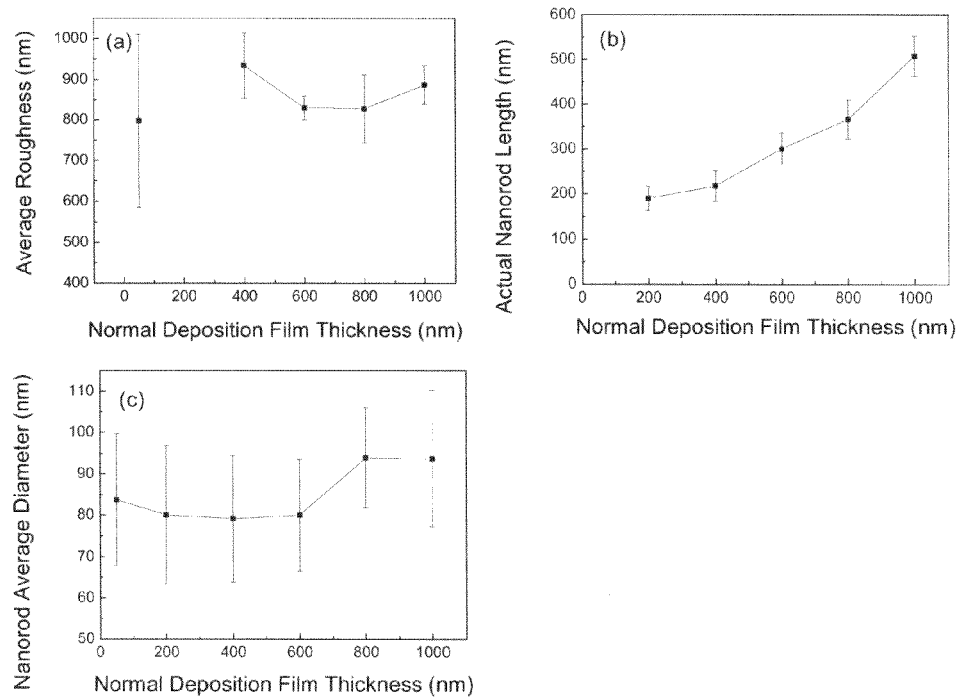
FIG. 5A illustrates a graph of RMS roughness.
FIG. 5B illustrates a graph of nanorod length.
FIG. 5C illustrates a graph of nanorod diameter as functions of normal deposition thickness.
Figure 6A:
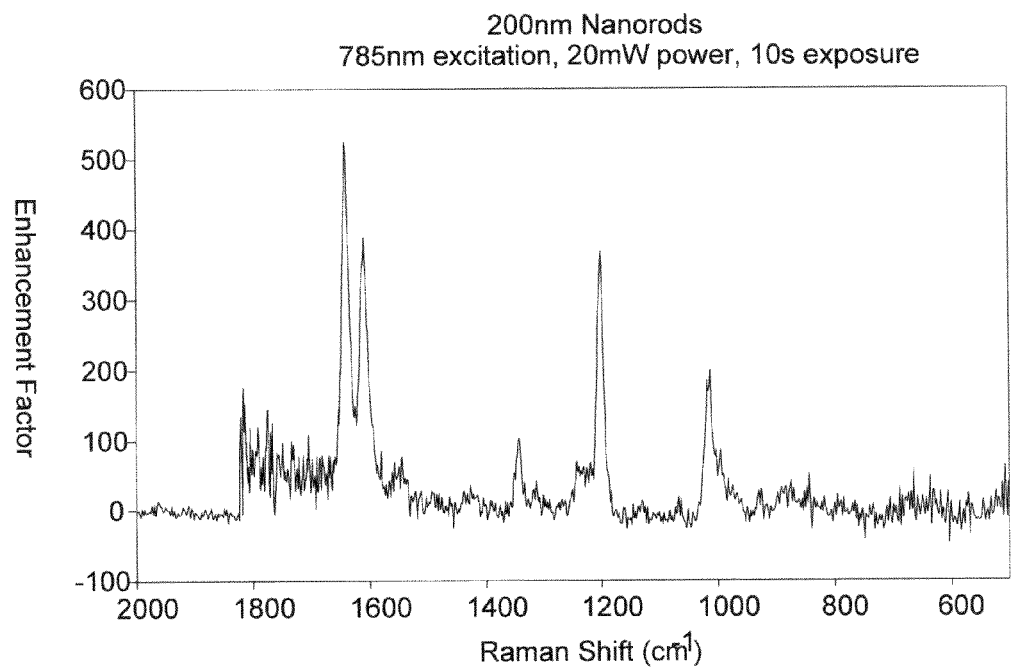
FIGS. 6A through 6E illustrate SERS spectra for samples having various length nanorods.
Figure 6B:
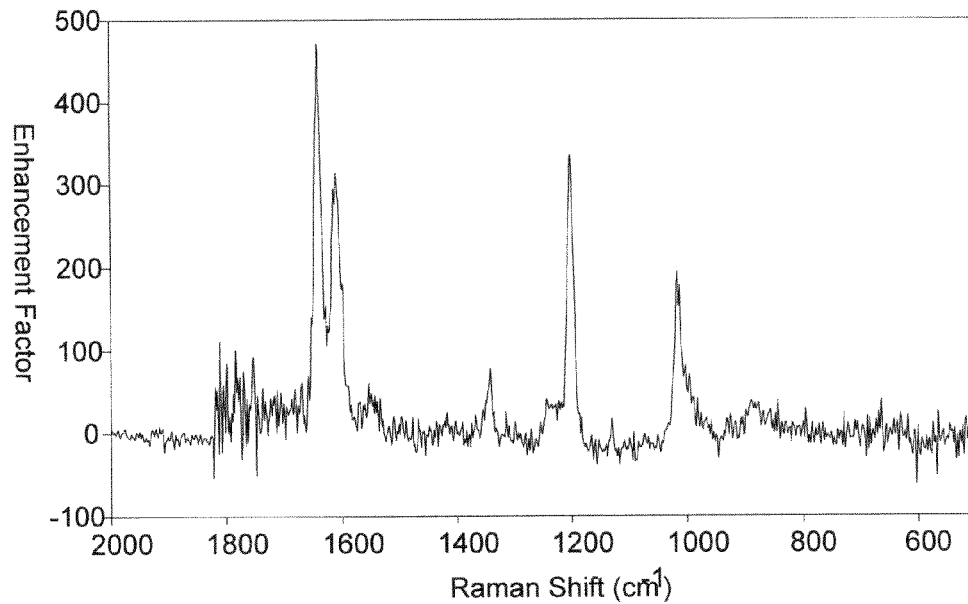
Figure 6C:
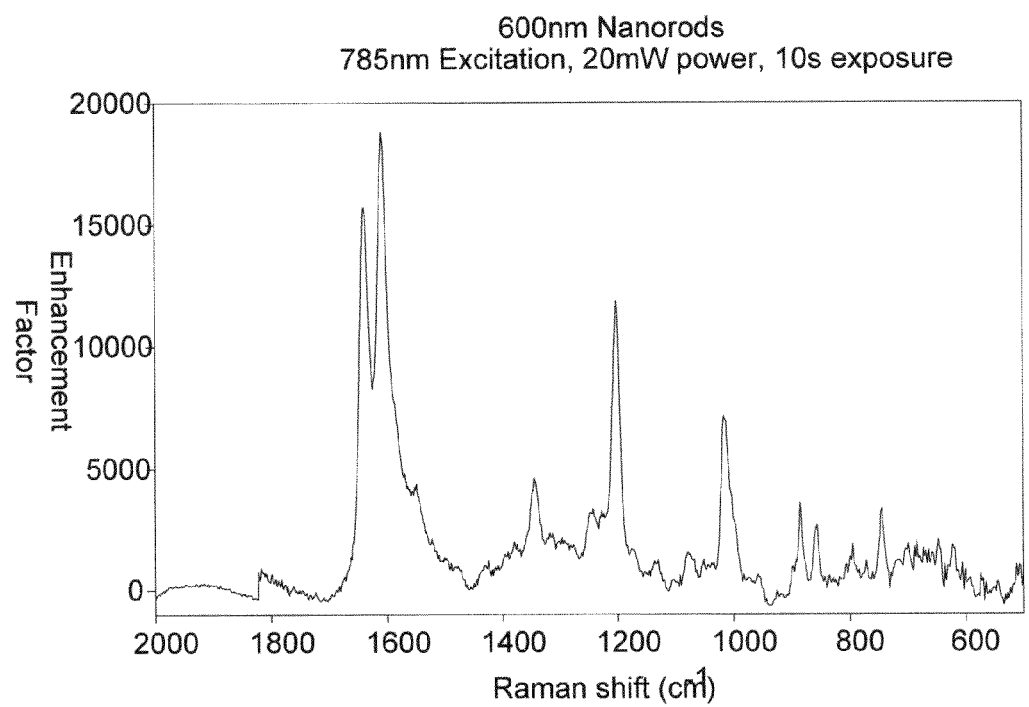
Figure 6D:
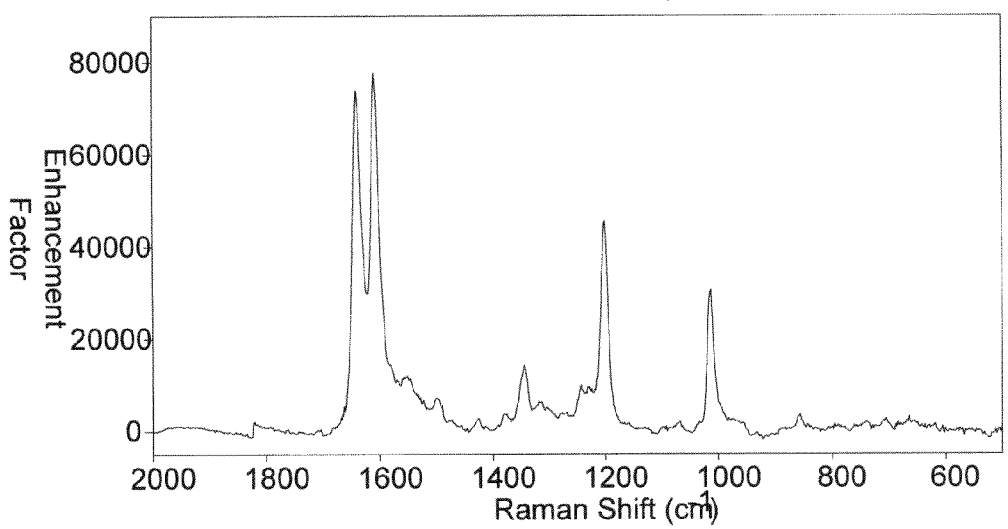
Figure 6E:
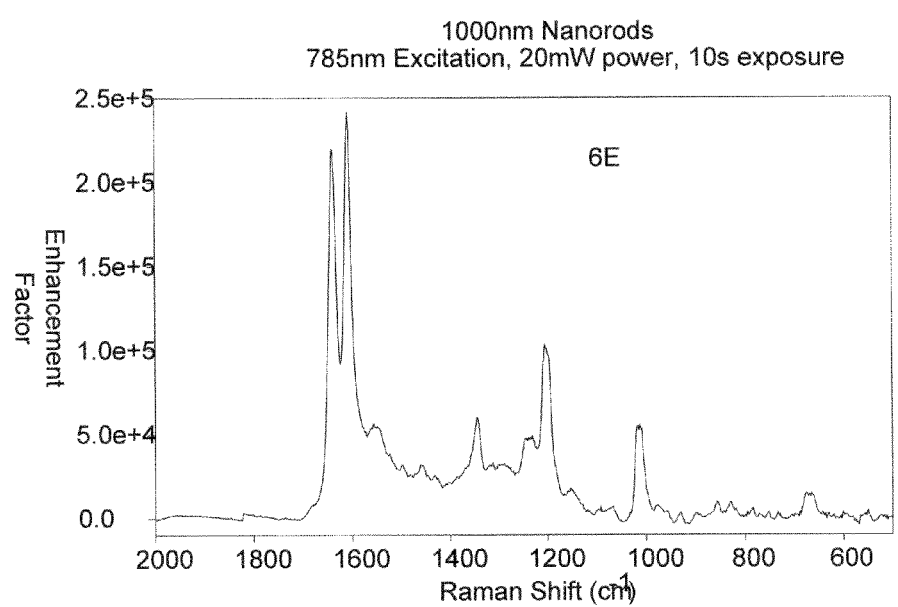

The actual length and density of the rods were measured using Scanning Electron Microscopy (SEM), and the roughness of the surfaces was measured using Atomic Force Microscopy (AFM). FIG. 4 shows the SEM images of the nanorods at different sections on the substrate. The average roughness, diameters, and actual lengths of each section of nanorods are displayed in the graphs illustrated in FIG. 5.

The actual rod length denotes the fact that when depositing at an angle of about 86°, the deposition rate displayed by the thickness monitor is not the same as the amount of material actually deposited onto the substrate due to a reduced flux. The diameter is representative of the average width of the tips of several hundreds of rods at a given length.

SERS Measurements:

Surface Enhanced Raman spectra were acquired using a Kaiser Optical Systems confocal Raman microscope (Kaiser Optical Systems Incorporated, Ann Arbor, Mich.) equipped with a liquid nitrogen cooled Charge Coupled Device (CCD) camera (Princeton, Instruments, Trenton, N.J.). The spectrograph used was a Holospec f/1.8-NIR spectrometer equipped with a HoloPlex grating that simultaneously measures the range of 100 to 3450 $cm^{-1}$ at an excitation wavelength of 785 nm illumination supplied by a Coherent Radiation 899 Ti:Sapphire Ring Laser (Coherent, Santa Clara, Calif.) pumped by a Coherent Radiation Innova 300 Series $Ar^+$ laser (Coherent, Santa Clara, Calif.). SERS spectra were collected with ~20 mW laser power at the sample under the microscope objective.

All spectra were collected using the Holograms 4.0 software supplied by the manufacturer. Post processing of the collected spectra was performed using GRAMS32/AI spectral software package (Galactic Industries, Nashua, N.H.). Center of Gravity calculations were made using a GRAMS32 based program written in our laboratory (R. A. Dluhy, unpublished). All spectra were baseline corrected for clarity.

The molecular probe used in this study was trans-1,2-bis (4-pyridyl)ethene (BPE, Aldrich, 99.9+%). BPE solutions were prepared by sequential dilution of HPLC grade methanol (Aldrich). BPE solution was applied to each of the SERS substrates and allowed to dry before the acquisition of spectra. The concentration of the BPE and the volume applied were calculated so as to produce a surface coverage of about 0.21 monolayers (assuming $7 \times 10^{14}$ BPE molecules per $cm^2$ in a monolayer). It has been observed that at greater monolayer coverage the SERS intensity drops off significantly. This drop-off has been attributed to inter-adsorbate interactions and coverage-dependent dielectric interactions. Spectra were acquired for about 10's and obtained for multiple spots on each substrate. BPE was chosen as the probe to calculate enhancement factors because of its high Raman scattering cross-section and its ability to adsorb strongly and irreversibly to the Ag substrate. The 1200 $cm^-$ peak of BPE was chosen for the quantification because of its relative insensitivity to molecular orientation on a Ag surface. FIGS. 6A through 6E show the SERS spectroscopy of different samples with different nanorod lengths.

Calculation of Surface Enhancement Factor

The Surface Enhancement Factor (SEF) is defined as the ratio of the integrated intensities contributed by the molecules on the surface and in the solution, respectively. where $I_{surf}$ and $I_{bulk}$ denote the integrated intensities for the 1200 $cm^{-1}$ band of the BPE adsorbed on the Ag surface and BPE in solution respectively, whereas $N_{surf}$ and $N_{bulk}$ represent the corresponding number of BPE molecules excited by the laser beam. Thus from the surface Raman signal detected, the solution spectrum, and the solution concentration, the Surface Enhancement Factor was calculated for the different SERS substrates.

$N_{surf}$ was calculated using the following approximation:

$$N_{surf} = A_{substrate} \times 0.21 \times 7 \times 10^{14} \times \pi a^2$$

where $A_{substrate}$ is the geometric area of the SERS substrate (in $cm^2$); and a is the radius of the laser focal spot.

$N_{bulk}$ was calculated using the following approximation:

$$N_{bulk} = \pi a^2 hcN_A$$

where c is the concentration of the BPE solution in the cuvette; h (in μm) is the confocal depth; and $N_A$ is the Avogadro number.

$I_{surf}$ and $I_{bulk}$ were calculated from the integrated area under the 1200 cm$^{-1}$ band in the BPE spectrum using a Center of Gravity algorithm written by the present investigators in the GRAMS32 environment.

Figure 7:
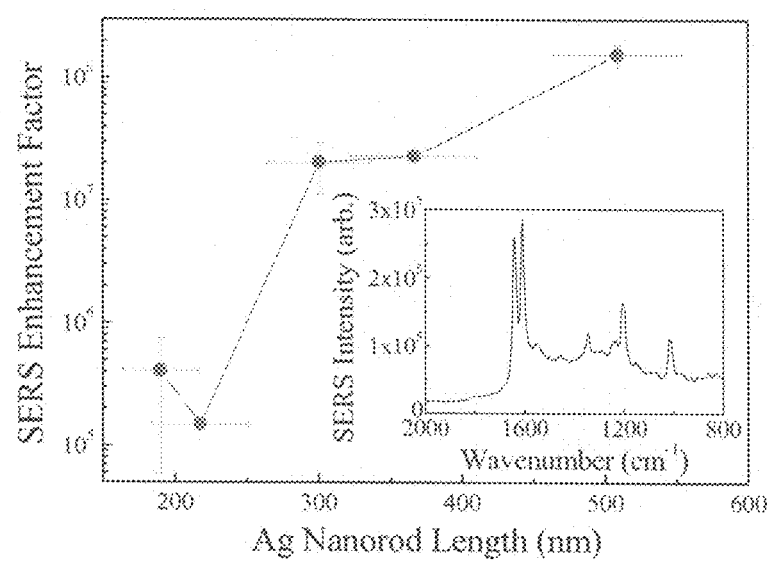
FIG. 7 illustrates a graph of the SERS enhancement factor relative to the length of the nanorods.

Surface Enhancement Factors (EF) were calculated for each of the spectra collected on all the SERS substrates and were plotted with error bars against the nanorod length. FIG. 7 shows the actual EF versus nanorod length.

Example 2

Using Aq Nanorod-Based SERS to Detect Different Strains of *Mycopasma pneumoniae*

The present example presents experiments demonstrating the use of embodiments of the SERS system of the present disclosure (Ag nanorod substrates) as a rapid, sensitive and discriminatory method for detection and differentiation of *Mycoplasma pnuemoniae* (*M. pneumoniae*) strains.

Mycoplasma Preparation Methods

Cell Preparation

*M. pneumoniae* strains were stored at −80° C. and cultured in 25 ml SP4 medium in tissue culture flasks at 37° C. for 4 days, when the pH indicator became orange, and lawn-like growth was observed by microscopic examination. Cultures were scraped from the surface of the flasks for the M129 and FH strains and transferred to an Oakridge tube; for the non-adherent strain II-3 the bacterial culture was poured directly into an Oakridge tube without scraping. Samples were centrifuged in an Eppendorf 5810 table top refrigerated centrifuge at 6° C. for 30 minutes at 11,500 rpm. The supernatant was discarded and the pellet was suspended in 1 ml SP4 medium, vortexed, syringe-passaged 10× with 25 gauge needle to disaggregate cells, transferred to a 5-ml Oakridge tube (rinsing the original tube with 1 ml SP4), syringe-passaged 10× with 25 gauge needle, and stored in a −80° C. freezer.

Cell Quantitation

900 μl SP4 was added to labeled tubes (−1 to −11). The *Mycoplasma* suspensions were syringe-passaged 10× with 25 gauge needle, and 100 μl from each was transferred to the first tube and subsequently serially diluted 10-fold in the remaining tubes. Each was syringe-passaged before transferring 100 μl to PPLO agar plates for spread-plating. These were incubated at 37° C. until colony growth was visible by phase contrast microscopy (typically 7 days). In order to visualize *Mycoplasma* colonies, each plate was overlaid with 0.8 ml blood agar 20% sheep blood in 1% Noble agar in saline).

Cell Preservation

Centrifuged sample 14000 rpm at 6° C. for 15 min, then discarded supernatant and suspended pellet in 1 ml d H$_2$O. Repeated 3×, then suspended in 50 μl d H$_2$O, Syringe-passaged 10×, then added 0.4 μl formalin to 10 μl culture, vortexed, and refrigerated.

SERS Measurements

SERS spectra were acquired using a near-IR confocal Raman microscope system (Hololab Series 5000, Kaiser Optical Systems, Inc., Ann Arbor, Mich.). A fiber-optic interfaced 785 nm near-IR diode laser (Invictus, Kaiser Optical) was used as the laser source and the spectrograph was a Kaiser Optical Holospec f/1.8-NIR equipped with a LN2-cooled CCD camera (1024EHRB, Princeton Instruments, Trenton, N.J.). The laser power at the sample varied between 10-15 mW and spectral collection times were set at 30 s. A 2.0-μL aliquot of *Mycoplasma* suspension was applied to the array Ag nanorod substrate and allowed to evaporate at room temperature prior to spectrum acquisition. Each *Mycoplasma* strain was applied to 3 different substrates to establish substrate-to-substrate reproducibility. Within substrate reproducibility was determined by collecting 5 spectra from different locations within the same sample area for each sample. This produced a total of 15 spectra for each *Mycoplasma* strain. Water was applied to the substrates as a control following the same procedure as the *Mycoplasma* samples.

Results

SERS Spectra

The major challenge associated with SERS is the production of reproducible substrates, resulting in reproducible spectra. Establishment of reproducibility is instrumental in the development of a SERS-based biosensing and classification methodology. FIG. 8 showcases the reproducibility of the normalized SERS spectra obtained with our OAD-fabricated SERS substrates. The spot-to-spot spectral variation within a single substrate was assessed by comparing five spectra for the M129 strain that were collected from different locations within the same sample well. FIG. 8A clearly demonstrates the high spectral reproducibility for spectra collected on the same substrate. Furthermore, it is necessary to confirm the reproducibility of substrate fabrication. The spectral reproducibility between substrates was assessed by plotting the average spectra (n=5-7) from three different substrates. The substrate-to-substrate reproducibility is illustrated in FIG. 8B. These data in FIG. 8 confirm that the OAD substrates can be used to evaluate *Mycoplasma* and argue that spectral differences can be attributed to differences in the structure and composition of analyte and not to differences in the substrate.

The main bands in the SERS spectra of the *Mycoplasma* samples are due to cell surface proteins and nucleic acid. The *Mycoplasma* samples were suspended in water which should not yield a background SERS signal; however, adsorption of contaminates from the atmosphere generated background SERS peaks. Thus, careful analysis of substrate background was necessary as a control. Embodiments of the present disclosure are able to distinguish among the following *M. pneumoniae* strains: M 129, FH and II-3. This is illustrated by the spectra in FIG. 9, which displays the averages of 15-20 spectra collected from three substrates for each of the *Mycoplasma* strains tested.

Figure 9:
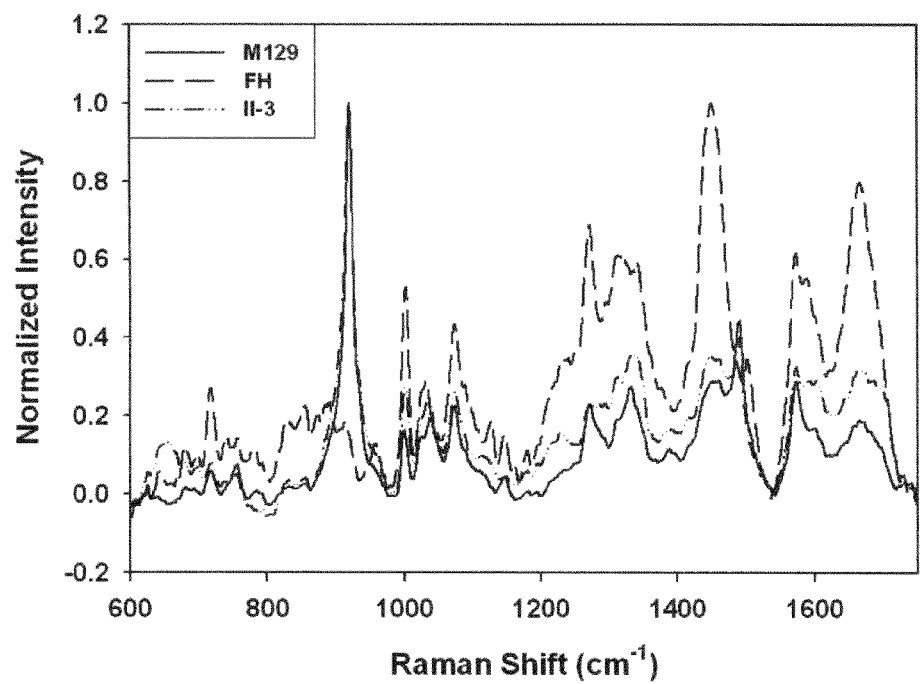
FIG. 9 illustrates the average SERS response for three *M. pneumoniae* strains—M129, FH and II-3.

Visual inspection of the spectra reveals that the most noticeable difference is the absence of the sharp band at 920 cm$^{-1}$ for the FH strain. Additionally, all three of the *Mycoplasma* strains have similar bands; however, the relative intensities for the FH strain differ significantly. This is most obvious for the band at 1450 cm$^{-1}$. While this band is only moderate in relative intensity for the M129 and II-3 strains, it is the most intense band for the FH strain. These spectral differences lead to straightforward differentiation of the FH strain from both the M129 and II-3 strains via simple spectral analysis, although, more automated or objective methods of discrimination are desirable. Visual inspection to discriminate between M129 and II-3 according to spectral differences, however, would be very tedious. That is not to say that slight differences between M129 and II-3 can not be observed. FIG. 9 reveals a band at 652 cm$^{-1}$ for II-3 while it is absent from the M129 spectrum, in addition to slight differences in the relative intensities for a few other bands.

SERS Spectra Outliers Analyzed

The raw SERS spectra were analyzed to determine why some spectra failed to fall within the correct cluster in the scores plots. The spectra for each of the outliers circled in FIG. 10 was identified and plotted to determine if its spectrum was truly non-representative of the strain. Based on FIG. 10, one spectrum for FH is determined to be abnormal, and it was collected from substrate 1. FIG. 11 plots all five spectra collected for the FH sample on substrate 1. The spectrum responsible for the outlying FH data point in the scores plot is significantly different than all other spectra for FH, confirming that it is truly atypical. Similar comparative analysis of the scores plot and raw spectra can be done to identify all non-representative spectra. It is likely that these anomalous spectra result from collecting data near the sample edge where bacteria surface concentrations are lower and no bacteria are located within the irradiated sample area, or in locations where the nanorods are no longer intact and the SERS enhancement is compromised.

Figure 12A:
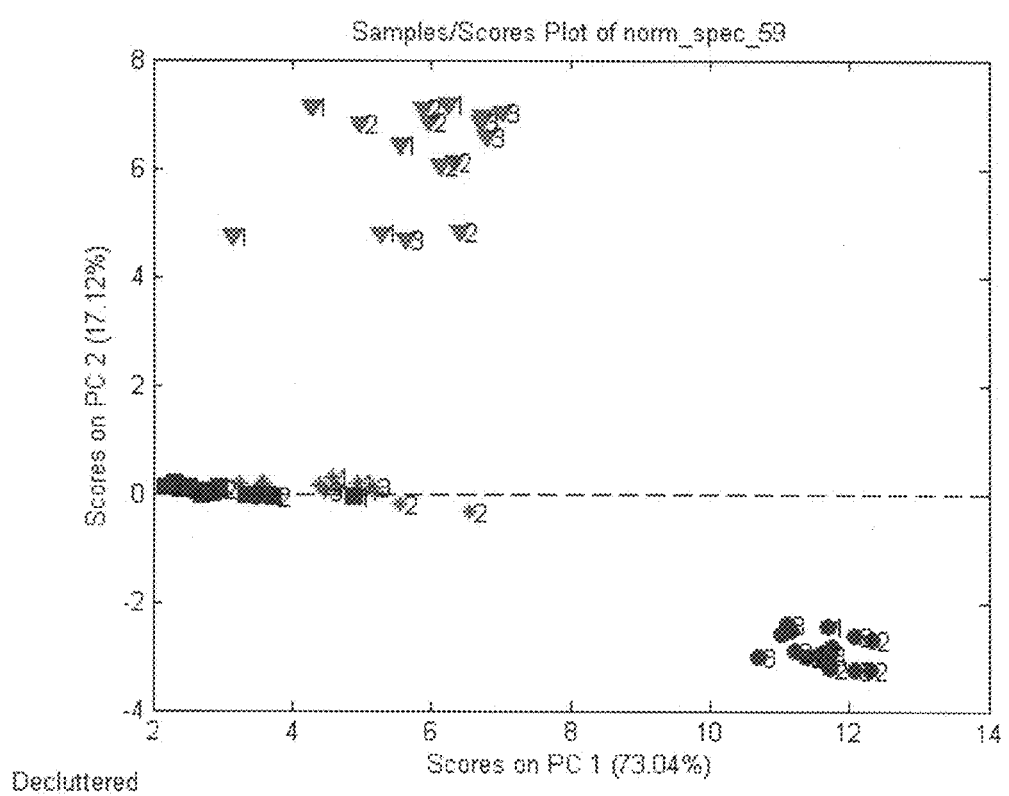
FIGS. 12A through 12B illustrate PCA scores plots for the *M. pneumoniae* and water samples after removal of the outlying spectra.
Figure 12B:
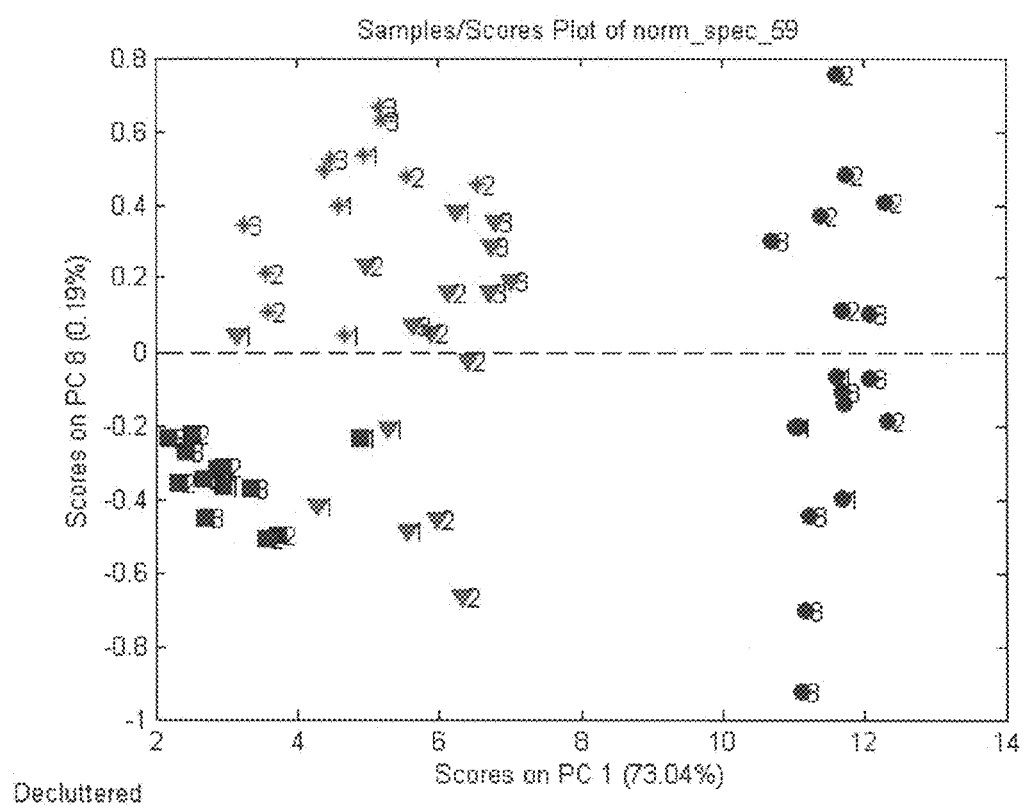

FIG. 12 displays the PCA scores plot for a model built with the remaining 59 spectra after removal of the 7 uncharacteristic spectra. Similar to FIG. 10, the plot of PC 2 versus PC 1 reveals three clusters of data, which groups the M129 and II-3 strains together. Additionally, M129 can be differentiated from II-3 using the scores for PC 8. Unlike FIG. 10, however, the clusters in FIG. 12 are well-defined without any outlying data points.

Principal Component Analysis (PCA) to Identify Individual *Mycoplasma pneumoniae* Strains PCA is a method of recasting the high dimensional data onto a new set of axes or orthogonal basis vectors that are typically called principal components (PC) (See Esbensen, K. H. *Multivariate Data Analysis—in practice,* 5 ed.; CAMO Process: Oslo, 2004, which is incorporated by reference for the corresponding discussion).

Figure 10A:
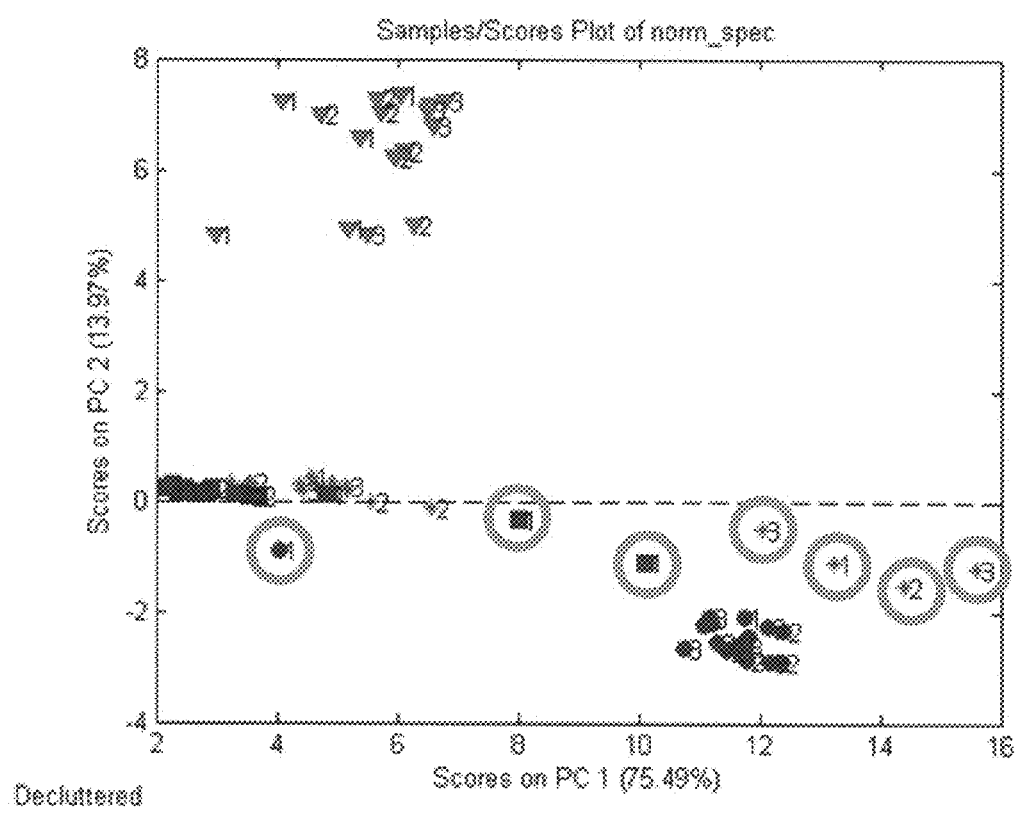
FIGS. 10A through 10B illustrate PCA (Principal Component Analysis) scores plots for the *M. pneumoniae* and water samples.
Figure 10B:
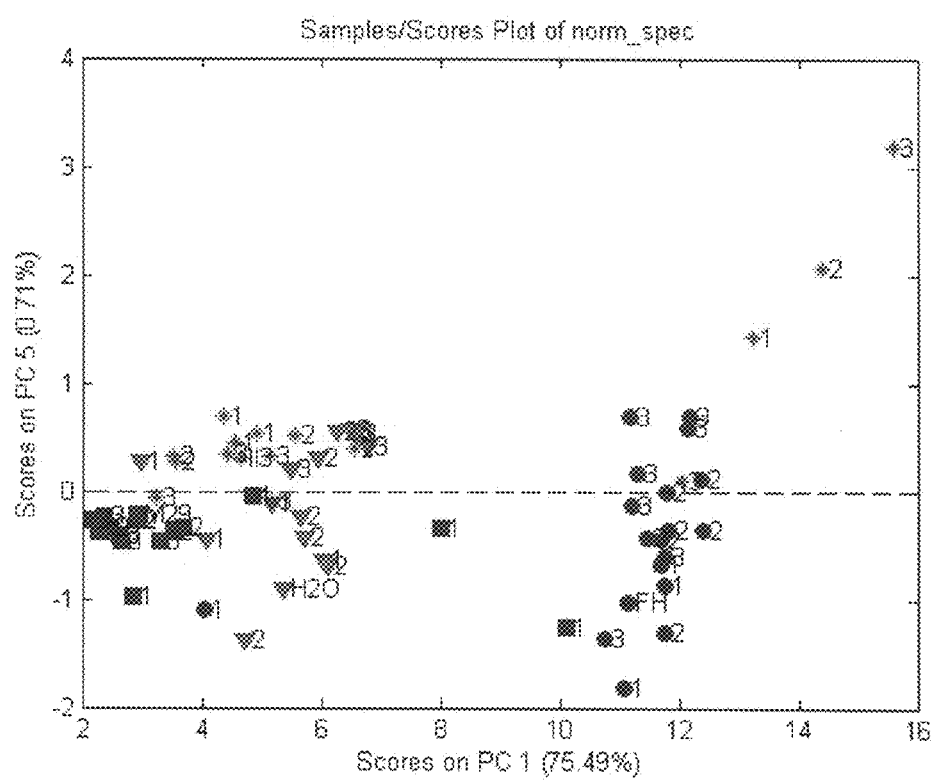

A PCA model of the data was generated for the 66 spectra using the spectral range of 600-1750 $cm^{-1}$. FIG. 10 shows the 2-dimensional scores plot for two sets of principle components (PCs). The scores plots demonstrate the clustering of similar data. For example, a plot of PC 2 versus PC 1 reveals three well-separated classes of samples. One cluster includes the background spectra, a second contains the spectral data for the FH strain, and a third cluster contains spectral data for both the M129 and II-3 strains. The low order PCs contain most of the spectral variance, thus it is reasonable to suspect that it is only possible to discriminate similar spectra with little variance, such as M129 and II-3, using the higher order PCs. Shown in FIG. 10, a plot of PC 5 vs PC 1 can be used to differentiate M129 and II-3. A positive value for PC 5 indicates that the sample is II-3 strain while a negative value for PC 5 indicates that the sample is M129.

K-Means Clustering Algorithm Analysis

Figure 13:
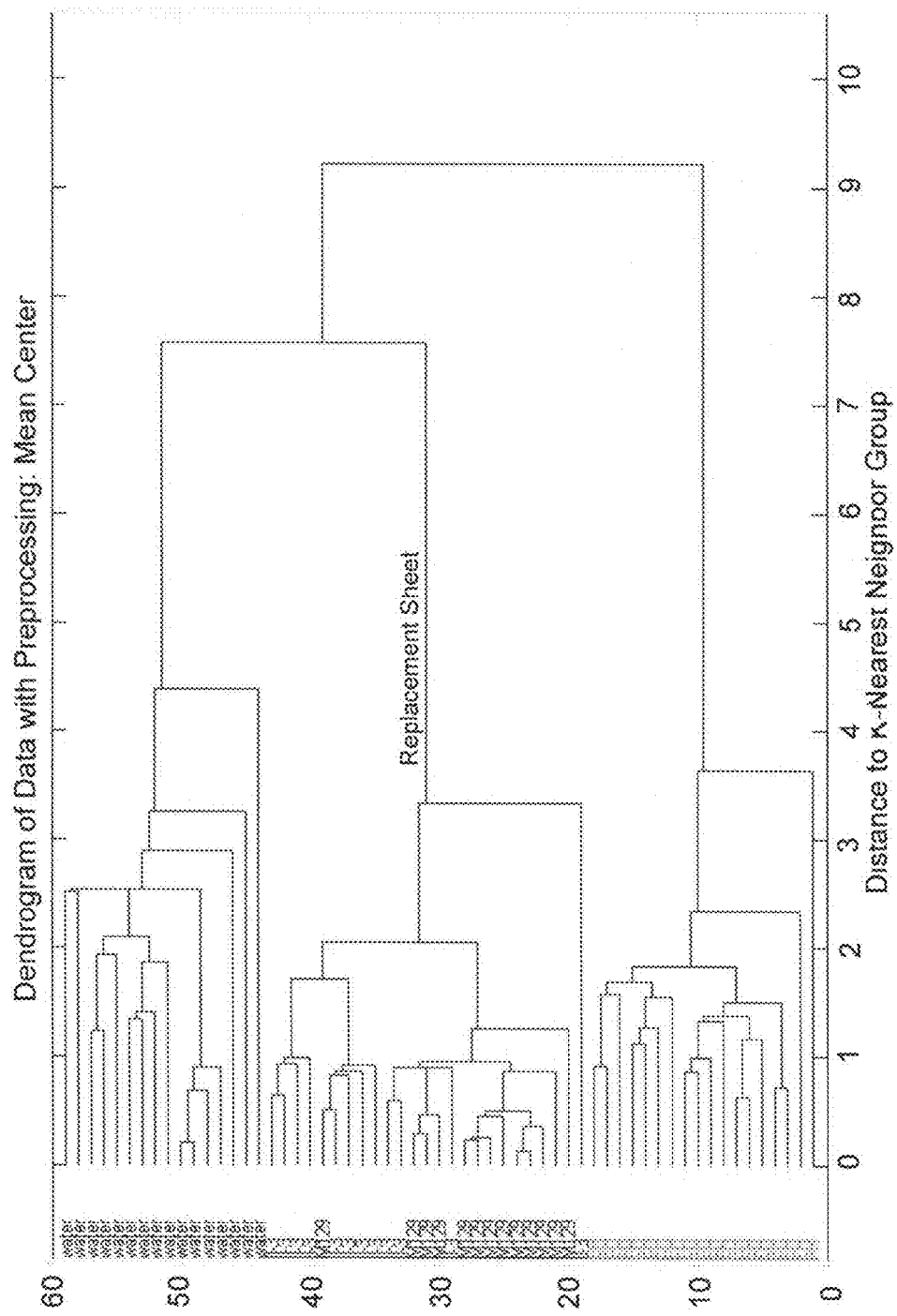
FIG. 13 illustrates a dendogram of spectral relatedness based on K means hierarchical clustering using 8 PCs.

The samples were classified according to a K-Means Hierarchical Clustering Algorithm, using the 59 representative spectra. The sample similarities are measured using the first 8 PCs to reduce dimensionality and eliminate noise. Initially, each data point is assumed to be a single cluster. The software runs the clustering algorithm to combine the two closest clusters into a new single cluster. The algorithm is repeated several times until each cluster is linked to another and the degree of similarity between each data point is presented as a dendogram. The K-means hierarchical clustering results are given in FIG. 13. Both the FH strain and background samples correctly cluster in the dendogram. Only one of the M129 samples was incorrectly clustered with the II-3 strains and two of the II-3 strains were incorrectly clustered with the M129 strains. Of the 59 *Mycoplasma* samples 56 were correctly classified according to the specific bacterial strain using hierarchical cluster analysis.

Conclusions

There is a crucial need for the development of a rapid sensitive test for the detection of *Mycoplasma* infections and the classification of *Mycoplasma* strains for epidemiological purposes. In the present embodiment, a SERS-based biosensor has been developed and applied to the rapid detection and differentiation of individual *Mycoplasma* strains. Furthermore, the OAD fabrication method has been shown to be capable of economically producing robust, reproducible biosensing SERS substrates which provide extremely high enhancement factors. In the present example, 95% of the bacterial samples were correctly classified. This example demonstrates the power of SERS to differentiate closely related strains of *Mycoplasma* (i.e., one base pair shift) in less than one minute when coupled to chemometric methods for data analysis.

Example 3

Using Ag Nanorod-Based SERS to Detect Different Strains of Rotavirus

The present example presents experiments demonstrating the use of embodiments of the SERS system of the present disclosure (Ag nanorod substrates) as a rapid, sensitive and discriminatory method for detection and differentiation of Rotavirus.

Virus Preparation Methods

Eight human rotavirus strains representing G type 1, 2, 3, 4 and 9 were all propagated in MA104 cells in the presence of trypsin (Table 1). Briefly, viruses were prepared in MA104 cells grown in DMEM supplemented with 10% fetal bovine serum. Virus stocks were activated with 10 ug/ml of porcine trypsin for 30 min at 37 C, then propagated in mA104 cells in the presence of 1 ug/ml of trypsin. Cells were incubated at 37° C. until a cytopathic effect was evident, then lysates were frozen and thawed twice. The viral tires of all virus stocks were determined by fluorescent focus neutralization assays.

TABLE 1

Genotype classification of Rotavirus strains.

| Strain | VP7 genotype (G type) | VP4 genotype (P type) | VP6 subgroup |
|---|---|---|---|
| RV4 | 1 | 8 | II |
| Wa | 1 | 8 | II |
| RV5 | 2 | 4 | I |
| S2 | 2 | 4 | I |
| RV3 | 3 | 6 | II |
| Yo | 3 | 8 | II |
| ST3 | 4 | 6 | II |
| F45 | 9 | 8 | II |

SERS Measurements

SERS spectra were acquired using a near-IR confocal Raman microscope system (Hololab Series 5000, Kaiser Optical Systems, Inc., Ann Arbor, Mich.). A fiber-optic interfaced 785 nm near-IR diode laser (Invictus, Kaiser Optical) was used as the laser source and the spectrograph was a Kaiser Optical Holospec f/1.8-NIR equipped with a $LN_2$-cooled CCD camera (1024EHRB, Princeton Instruments, Trenton, N.J.). The laser power at the sample was ~12 mW and spectral collection times were set at 30 s. A 2.0-μL aliquot of intact virus was applied to the Ag nanorod array substrate and allowed to evaporate at room temperature prior to spectrum acquisition. SERS spectra were collected from 10 spots across the substrate.

Results

SERS Spectra

Figure 14:
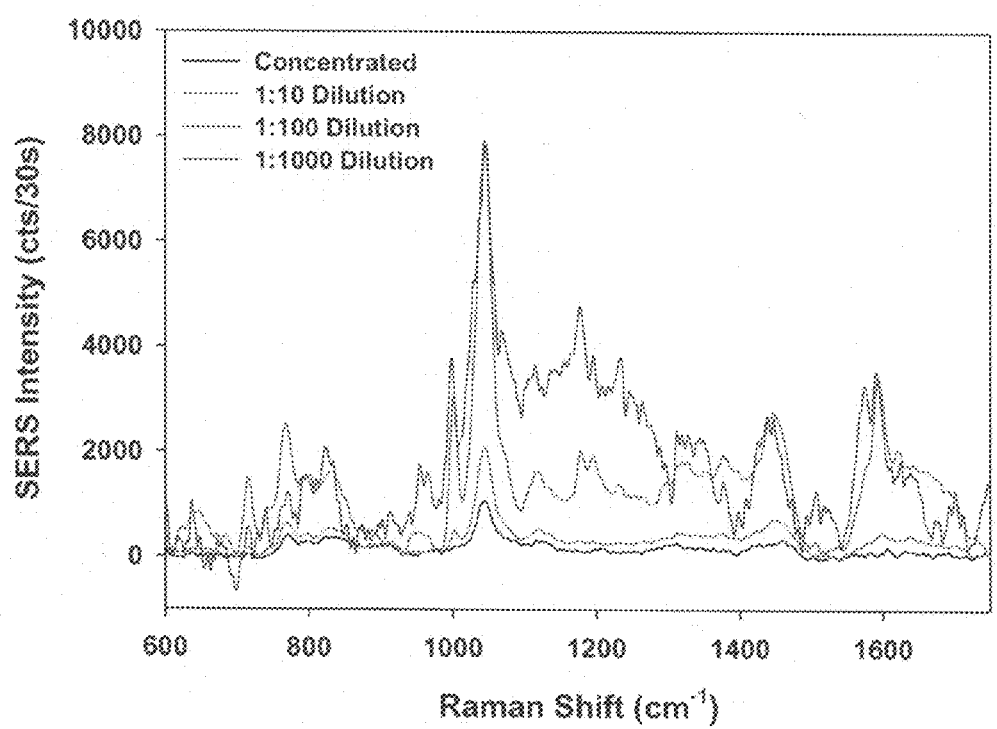
FIG. 14 illustrates the average SERS response for serial dilutions of Rotavirus RV4.

A single strain of rotavirus, RV4, suspended in cell culture media was applied to the OAD-fabricated SERS substrate to assess the SERS signal. While scattered bands were detected (FIG. 14), a thick sample film was observed on the biosensing substrate. SERS is a surface sensitive technique in which only the signal for the viruses in close proximity to the nanorod substrate is enhanced. It was likely that the laser could not penetrate the biofilm to excite the closely adsorbed virus, and the signal was derived from viruses a great distance from the surface where signal enhancement is limited. Thus, larger signals could be obtained by diluting the rotavirus samples with water, eliminating the thick sample film, and exciting the virus adsorbed directly on the substrate.

Virus Sample Dilution Yields Greatest Signal-to Noise Spectrum

SERS Spectra

The RV4 rotavirus strain was serially diluted with water, applied to the substrate, and analyzed with SERS. Eight spectra were collected and averaged for each dilution and the resulting spectra are presented in FIG. 14. As the sample was diluted from 100% to 1% the intensity of the SERS signal increased; presumably due to the reduction of the thickness of the sample film. At a lower concentration of 0.1% the SERS signal is comparable to the 1% sample; however, the S/N is much worse due to an increased level of spectral noise. Based on these results, it was concluded that SERS analysis of 1:100 dilutions of the Rotavirus samples provide the greatest structural information and this concentration was used in all subsequent experiments for strain classification.

Figure 15:
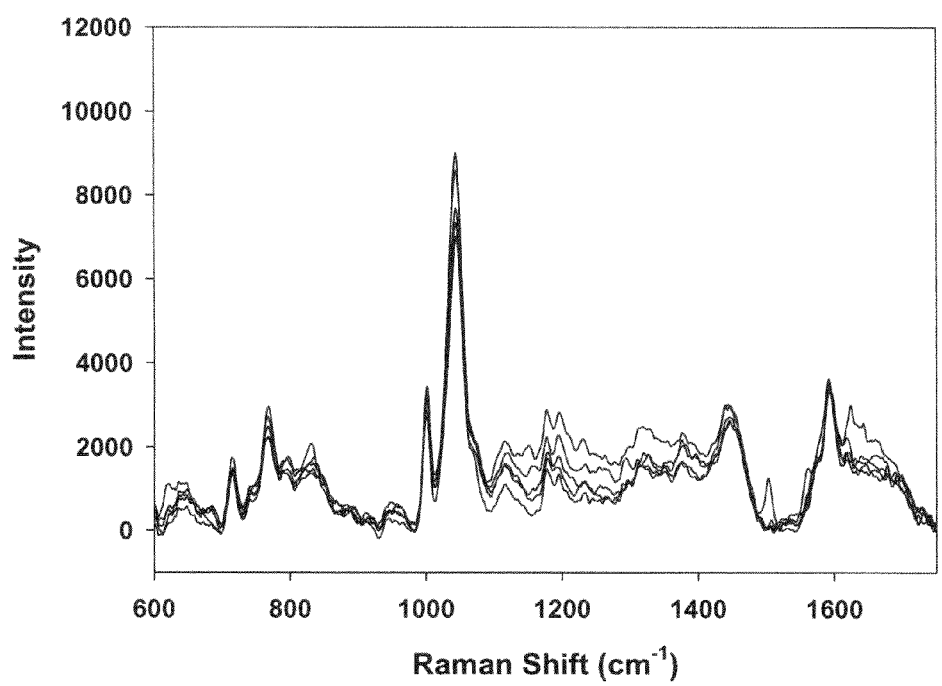
FIG. 15 illustrates SERS spectra for RV4 Rotavirus collected from several locations on the same substrate.

FIG. 15 showcases the reproducibility of the SERS spectra obtained with our OAD-fabricated SERS substrates. The spot-to-spot spectral variation within a single substrate was assessed by comparing five spectra for the RV4 strain that were collected from random locations on a substrate. FIG. 15 clearly demonstrates the high spectral reproducibility for spectra collected on the same substrate.

The raw SERS spectra for each sample differ in the number of scattered bands, band locations, and the magnitude of the bands. Variations in band frequencies reflect compositional and structural differences in the virus strains while differences in peak intensities are a result of slight differences in the morphology of the SERS substrates. To remove spectral disparities caused by the substrates, each SERS spectrum was normalized with respect to its most intense peak. This preprocessing step allows direct comparison of peak intensities between spectra obtained from different locations on a substrate or from different substrates.

Figure 16:
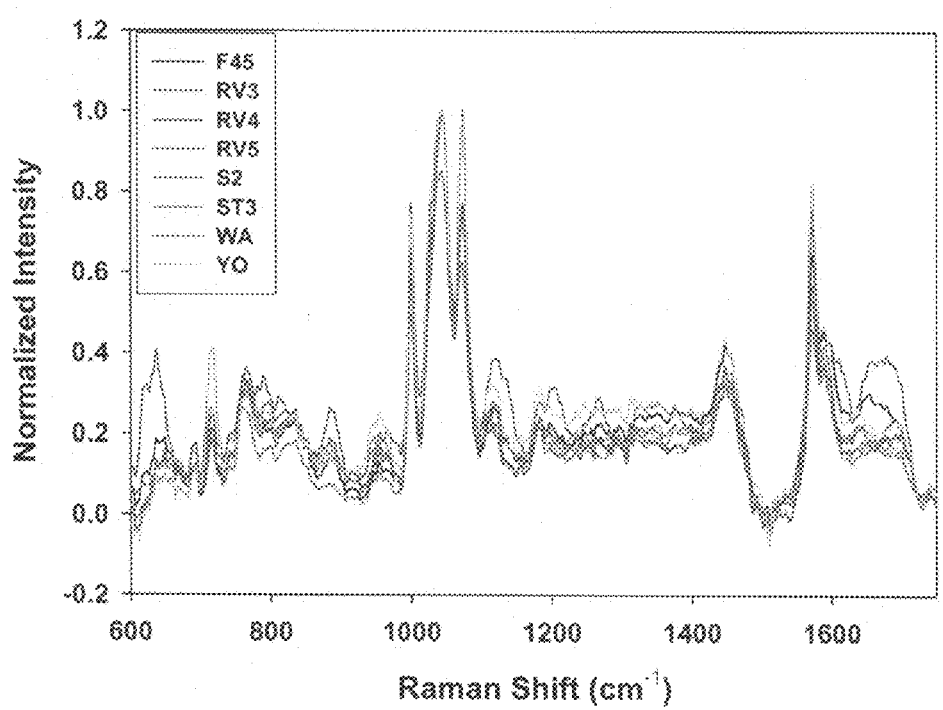
FIG. 16 illustrates the average SERS spectra for each of the following Rotavirus strains: RV4, WA, RV5, S2, RV3, YO, F45, and ST-3.

The multiple bands in the SERS spectra of the rotavirus samples may be due to the two outer capsid proteins (VP7 and VP4) and 1 inner capsid (VP6) protein and nucleic acid of the virus, as well as components of the background cell culture media. The same suspending media was used for each rotavirus strain so any SERS bands due to components of the media were constant; thus, all spectral differences were attributed to differences in the rotavirus strains. The closely related chemical composition and structure of the rotavirus strains give rise to similar SERS spectra. This is illustrated by the spectra in FIG. 16. Each spectrum displayed in FIG. 16 is an average of 6 spectra. Visual inspection to classify each virus strain according to spectral differences would be very tedious, if not impossible. That is not so say that differences can not be observed. While the number and location of bands is similar for each strain, close inspection of the spectra reveals several apparent differences in relative band intensities. For example, the most obvious case is for the RV5 strain in which the band at 1073 cm$^{-1}$ is more intense than the band at 1044 cm$^{-1}$ while the opposite is true for the other strains.

Principal Component Analysis (PCA) to Identify Individual RV Strains

PCA is a method of recasting the high dimensional data onto a new set of axes or orthogonal basis vectors that are typically called principal components (PC) (See Esbensen, K. H. *Multivariate Data Analysis—in practice*, 5 ed.; CAMO Process: Oslo, 2004, which is hereby incorporated by reference for the corresponding discussion). The PC which contains the greatest variance is labeled PC 1, while the axis containing the second most variance is termed PC 2. Thus, PCs model the most statistically significant variations in the dataset and are primarily used to reduce the dimensionality of the sample matrix prior to the use of clustering methods. PCA was employed for unsupervised EDA to visualize groupings of similar spectra and supervised Cluster Analysis was subsequently applied to definitively group the samples according to their spectral signatures.

Figure 17A:
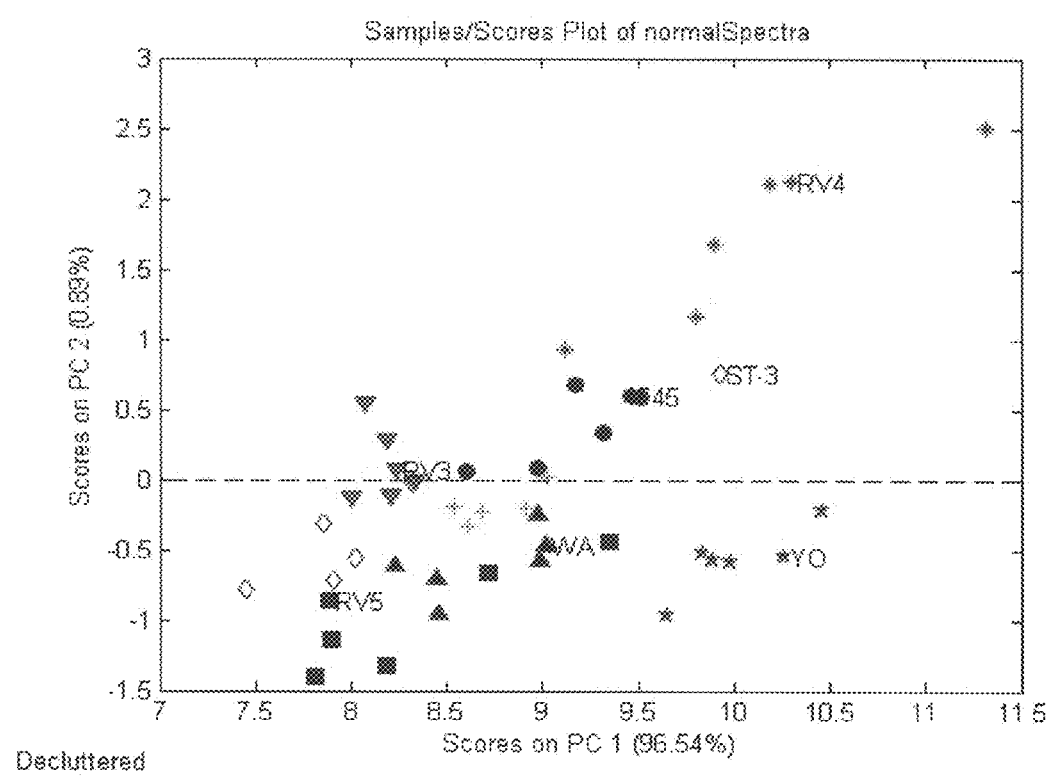
Figure 17B:
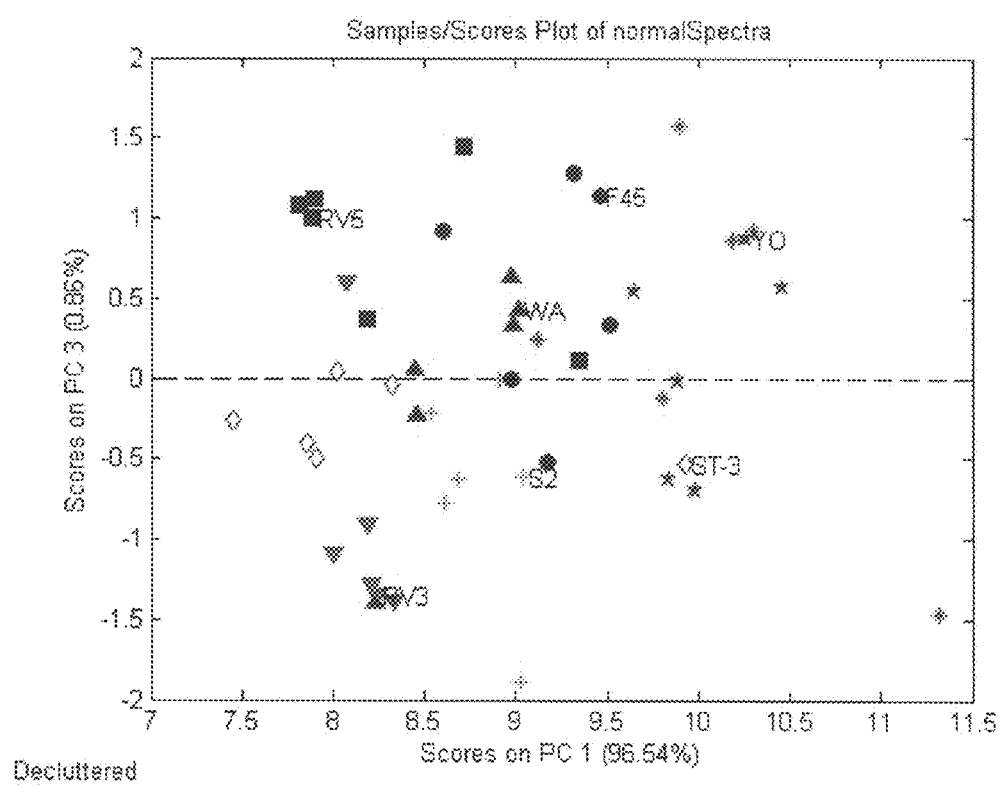
Figure 17C:
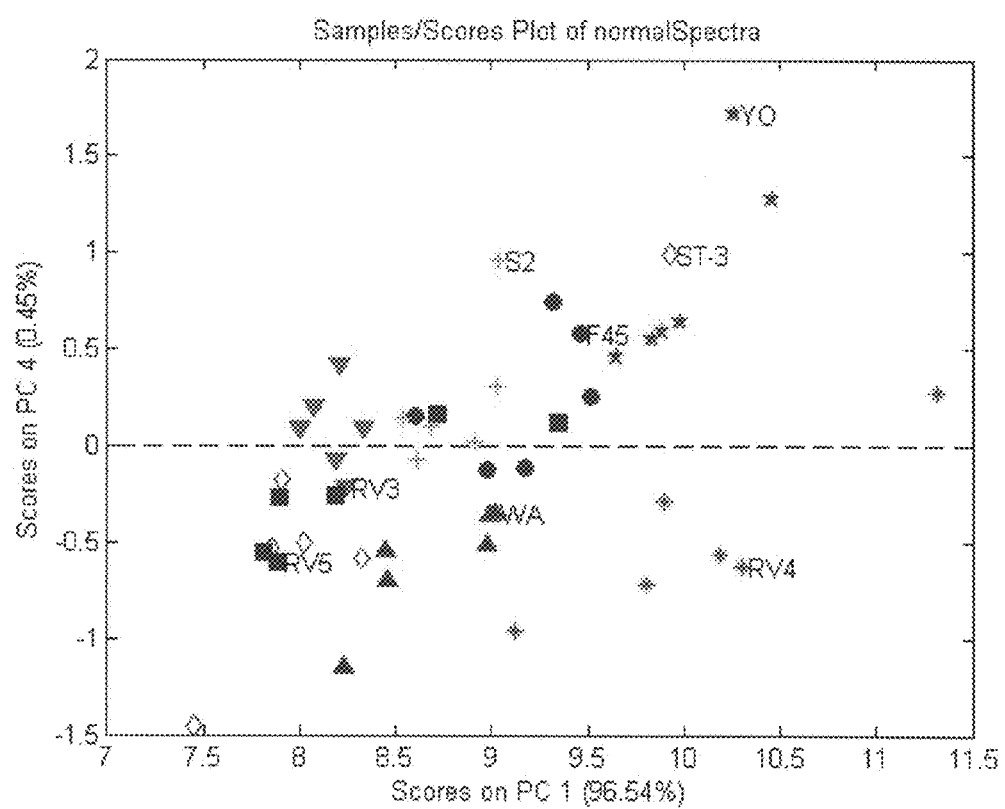
Figure 17D:
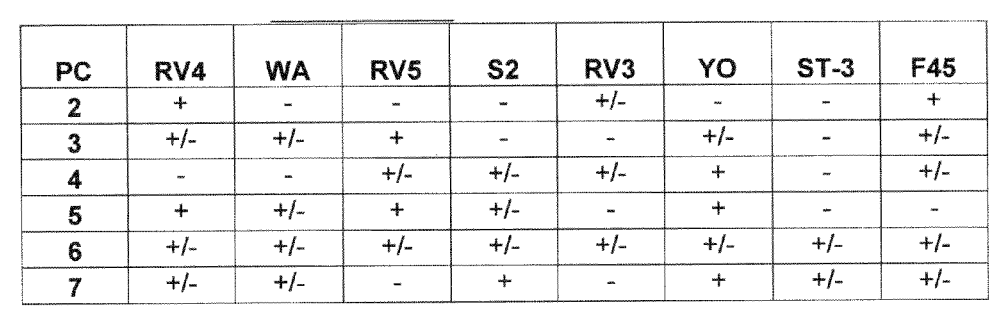

A PCA model of the data was generated for the spectra using the spectral range of 600-1750 cm$^{-1}$ using the first 8 PCs. FIGS. 17A through 17C show the 2-dimensional scores plot for several principle components (PCs). While none of these 2-dimensional plots adequately separates each of the samples into well-isolated clusters, combination of the information contained in all of the PC axes (7 dimensions) reveals the existence of all 8 classes. This is demonstrated in FIG. 17D. For example, negative scores for the first four PCs indicates that the sample must be a ST-3 strain. Moreover, a positive value for PC2 and negative value for PC5 categorizes a sample as rotavirus F45. Thus the analysis reveals that patterns in the PC values are unique for each rotavirus strain.

K-means Clustering Algorithm Analysis

The samples were also classified according to a K-means Clustering Algorithm (The Unscrambler v 9.8), which is less subjective to user interpretation than PCA, but requires knowledge of the exact number of classes in the dataset. The samples are randomly assigned to one of K (user-determined number) clusters. Based on prior knowledge of the samples in this study (and/or analysis of scores plots), K is equal to 8 for this dataset. The software then runs the clustering algorithm to determine the sum of the distance between each data point and the centroid of its assigned cluster. The algorithm is repeated several times to determine optimal clustering defined by the minimum sum of distances between each sample and its cluster centroid. The K-means classification results are given in FIG. 18. This clustering method resulted in correctly classifying all of the F45 and YO strains, while 4-5 out of 6 samples were correctly classified for each of the other strains. It should also be noted that this algorithm placed the RV3 and S2 strains in the same class. Thus, the 8 Rotavirus strains were placed into 7 classes while the 8$^{th}$ class was reserved for 2 outlying spectra.

Conclusions

There is a crucial need for the development of a rapid sensitive test for the identification of viruses and classification of viral strains. In the present embodiment, a SERS-based biosensor has been developed and applied to the rapid detection and differentiation of individual Rotavirus strains. Furthermore, the OAD fabrication method has been shown capable of economically producing robust, reproducible biosensing SERS substrates which provide extremely high enhancement factors. In the present example, 81% of the samples were correctly classified. This example demonstrates the power of SERS to differentiate individual strains of viruses in less than one minute when coupled to chemometric methods for data analysis.

Example 4

Detection of *Mycoplasma pneumoniae* using Nanorod Array Surface-Enhanced Raman Spectroscopy (NA-SERS)

The present example presents experiments demonstrating the use of embodiments of the SERS system of the present disclosure (Ag nanorod substrates) as a rapid, sensitive and discriminatory method for detection and differentiation of *Mycoplasma pneumoniae*.

SUMMARY

An obliquely-angled silver nanorod array was assessed as a biosensing platform for detection and differentiation of *Mycoplasma pneumoniae* (Mpn) using Raman Spectroscopy Stokes vibrational signals in combination with chemometrics and multivariate analysis to create a model for prediction of strains. Three closely related strains of Mpn were able to be detected at the CFU level and were differentiable with over 93%-100% Specificity and 93-100% Sensitivity.

This strategy holds great promise for widened application for other pathogens and for utilization in clinical and industrial settings. This is the first step in building a reference library with pure samples of known concentration, so that clinical samples in more complex backgrounds can next be assessed.

Background

*Mycoplasma pneumoniae*, the primary cause of atypical pneumonia and tracheobrochitis (Hardy, R. D. *Medscape* 2006, which is incorporated by reference for the corresponding discussion), has also been implicated in a wide range of chronic diseases, including asthma. The development of the disease state in humans can be complicated by the bacterium's incompletely understood mechanisms to evade the host immune system. It is known that attachment to the epithelial host cell surface is a requirement for onset of pathogenicity (Razin, S. *Biosci Rep* 1999, 19, 367-372, which is incorporated by reference for the corresponding discussion); several hypotheses have emerged to explain the ability of Mpn to persist as a systemic infection, from intracellularization to antigenic variation (Rocha, E. P.; Blanchard, A. *Nucleic Acids Res* 2002, 30, 2031-2042, which is incorporated by reference for the corresponding discussion). What is apparent is the need to accurately diagnose its presence for effective treatment. It has been demonstrated that asthma patients who are given antibiotics known to be effective against Mpn show improvements in their conditions (Brunetti, L.; Colazzo, D.; Francavilla, R.; Tesse, R.; De Sario, V.; Lore, M.; Armenio, L. *Allergy Asthma Proc* 2007, 28, 190-193, which is incorporated by reference for the corresponding discussion). Also complicating the diagnosis picture is the frequent co-infection rate by a second agent in conjunction with Mpn. Of the 22% of the community-acquired pneumonia (CAP) cases known to involve Mpn, 64% of them have a second bacterial infection present as well (Wendelien Dorigo-Zetsma, J.; Verkooyen, R. P.; van Helden, H. P.; van der Nat, H.; van den Bosch, J. M. *Journal of Clinical Microbiology* 2001, 39, 1184-1186, which is incorporated by reference for the corresponding discussion).

The use of vibrational spectroscopy as a detection method has regained interest with the development of systems that can enhance the scattered Raman Stokes component; IR was initially and extensively used to characterize bacteria with good specificity (Ellis, D. I.; Broadhurst, D.; Kell, D. B.; Rowland, J. J.; Goodacre, R. *Appl Environ Microbiol* 2002, 68, 2822-2828; Goodacre, R.; Shann, B.; Gilbert, R. J.; Timmins, E. M.; McGovern, A. C.; Alsberg, B. K.; Kell, D. B.; Logan, N. A. *Anal Chem* 2000, 72, 119-127, which are incorporated by reference for the corresponding discussion); however it suffered from the requirement of relatively large amounts of sample and interference from the water portion of the samples. Raman spectra are relatively immune to interference from water, and they provide complementary information to the IR data (Hendra, P. J. *Sampling Considerations for Raman Spectroscopy*, John Wiley & Sons, Ltd., 2002, which is incorporated by reference for the corresponding discussion). The inherently weak signal prevented it from being extensively exploited until recently, when enhancement of this portion of the vibrational spectrum through proximity to a metallic surface achieved levels that made it measurable (Vo-Dinh, T.; Houck, K.; Stokes, D. L. *Anal Chem* 1994, 66, 3379-3383, which is incorporated by reference for the corresponding discussion). The inconsistency in the reproducibility of these surfaces also stifled advancement of this application; however, nanorod fabrication procedures have been progressively improving, and this disclosure is based upon one such approach. An obliquely-angled silver nanorod array has been fabricated in a vacuum chamber with an electron beam sputterer with reproducible parameters and enhancement (Zhao, Y. P.; Chaney, S. B.; Shanmukh, S.; Dluhy, R. A. *J Phys Chem B* 2006, 110, 3153-3157, which is incorporated by reference for the corresponding discussion). This platform has previously been evaluated for enhancement of the Raman signal as well as for standardization of protocol and optimization of specifications. It has also been assessed for detection and differentiation of four closely related strains of Respiratory Syncytial Virus (RSV) (Shanmukh, S.; Jones, L.; Driskell, J.; Zhao, Y.; Dluhy, R.; Tripp, R. A. *Nano Lett* 2006, 6, 2630-2636, which is incorporated by reference for the corresponding discussion). In that study, this technology, in conjunction with chemometric analysis, identified the virus with Sensitivity of 60-90% and Specificity of >90%, numbers that warrant closer examination. Thus it seemed reasonable to assess this platform for use in *Mycoplasma pneumoniae* detection.

Methods

*Mycoplasma* Sample Preparation

Strains: M129, 18p, FH, 5p, II3, 3 passage. II-3 is a spontaneous mutant that arose from 16 passages of M129. Culture in 25 ml SP4 medium, 25 µl inoculum in 25 ml. Harvest when pH indicator changed to orange, log growth. M129 and FH, pour off medium, Resuspend in chilled HPLC grade $H_2O$, 25 ml. Scrape and transfer to Oakridge tube.

II-3, directly transfer to Oakridge tube without scraping. Beckman Avanti centrifuge, Program 1: 20000×g, 25 min, 4° C. Pour off supernatant. Resuspend in 10 ml chilled $H_2O$. Wash 3 times. Program 2: 20000×g, 20 min, 4° C. Last time, resuspend in 1 ml $H_2O$ in microcentrifuge tube. Spin in Eppendorf table top centrifuge, 14000 rpm, 15 min, 4° C. Resuspend in 500 µl HPLC grade $H_2O$. Syringe passage 10× with a 25 gauge needle. Transfer 100 µl to previously prepared dilution tubes with 900 µl $H_2O$. Serial dilutions to −10. Transfer 100 µl to PPLO agar plates (in triplicate). After 5 days' growth, blood overlay to visualize colonies.

From original tube, transfer 10 µl (×2) to 90 µl H2O for protein assay, BCA standard protocol. Fixation of samples: add methanol for 1:100 dilution of sample in methanol.

SERS Preparation

Nanorod preparation according to optimized protocol for maximum enhancement of the Raman signal. Briefly, an electron beam sputterer was used with a vacuum chamber for the thin film deposition of three sequential layers, 0.2 kÅ Ti, 5.0 kÅ Ag monolayer, 20.0 kÅ obliquely angled Ag nanorod array; average specs: 868±95 nm length. 90-100 nm diameter, 13 nanorods/µm² density, final angle 70° to normal.

Renishaw Settings:

5× objective. 15 mW power at sample surface, laser spot area=1265 µm². 10 second acquisition. 1492 data points from 400-1800 wave number range were taken. The peak intensities were processed at a CCD detector. The bare nanorods were initially examined for baseline spectral pattern and to determine the level of surface contamination present. 1 µl of sample from each strain was applied to three separate nanorods. Methanol background spectra were collected from ten separate locations on a nanorod.

Chemometric Analysis

Spectral collection with WIRES software. Data transferred into Excel spreadsheet. Creation of a y block in excel. CAMO Unscrambler software for preprocessing: Savitsky Golay, $2^{nd}$ order polynomial first derivative with 9 smoothing points (Savitsky, A.; Golay, M. J. E. *Anal. Chem.* 1964, 36, 1627-1639, which is incorporated by reference for the corresponding discussion). Unit Vector Normalization (Z. B., A. *J Am Soc Mass Spectrom* 2004, 15, 385-387, which is incorporated by reference for the corresponding discussion). PCA analysis (Esbensen, K. H. *Multivariate Data Analysis—in practice*, 5 ed.; CAMO Process: Oslo, 2004, which is incorporated by reference for the corresponding discussion). Exported to Matlab 6.5 with PLS toolbox 4.0, mean centered. HCA cluster analysis. PLS-DA analysis and model construction (Barker, M.; Rayens, W. *J Chemom* 2003, 17, 166-173, which is incorporated by reference for the corresponding discussion).

Results

Figure 19:
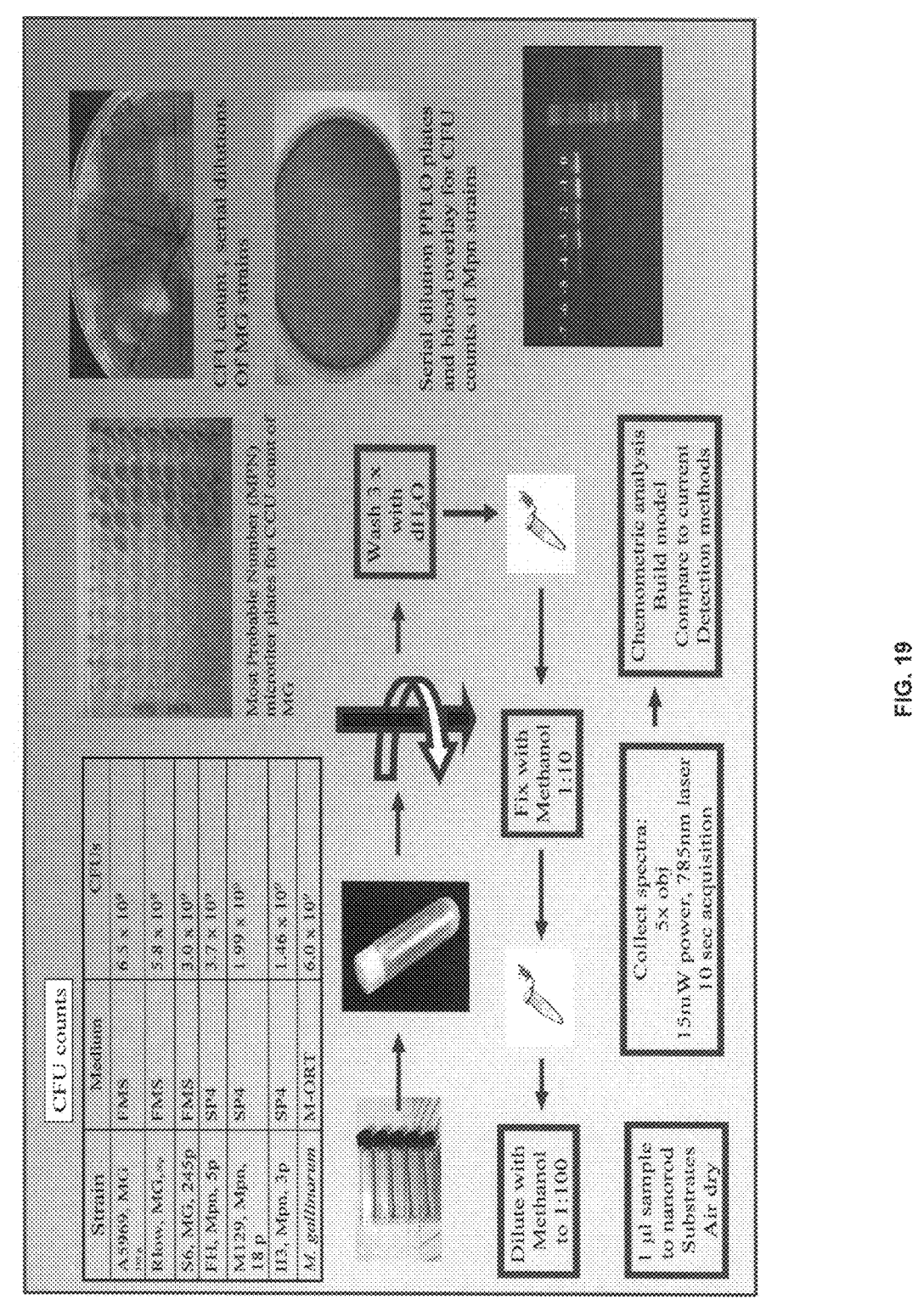

The Renishaw in Via Raman Microscope System was used to collect the spectra. Standardization was determined to be an important step for greater ease in comparing spectra and runs. Toward this end, the following settings were used for all data collection: the 5× objective was used to provide a more homogeneous spectrum through spatial averaging of the analyte. A 785 nm diode laser was used for excitation of the sample, and this choice avoided any interference by fluorescence. The laser power was set at 15 mW at the sample surface; this setting minimized saturation of the signal as well as fluorescence. The signal was acquired in 10 seconds, and multiple spectra were collected for each strain. Furthermore, each strain was sampled on three independent nanorod substrates. Different fixatives were examined to determine whether one technique provided superior preparation for spectral acquisition. See FIG. 19 for a schematic of the experimental design.

Figure 20:
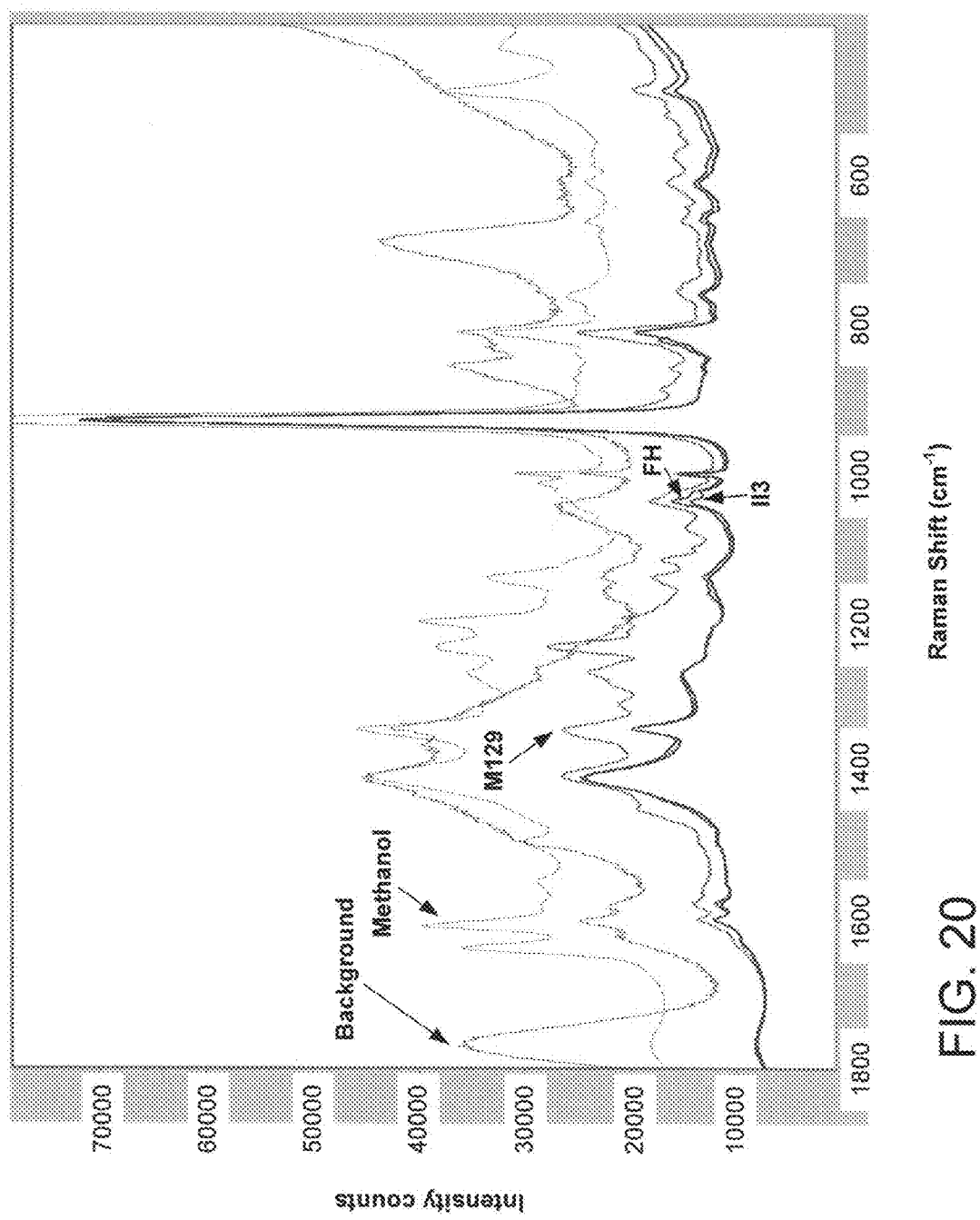
FIG. 20 is a graph that illustrates Average Spectra, 30 raw spectra added together to improve the signal to noise ratio, GRAMS software.

Chemometrics is a crucial analytical tool for a multidimensional spectral data set such as this (Barker, M.; Rayens, W. *J Chemom* 2003, 17, 166-173; Esbensen, K. H. *Multivariate Data Analysis—in practice*, 5 ed.; CAMO Process: Oslo, 2004; Felizardo, P.; Baptista, P.; Menezes, J. C.; Correia, M. *J. Anal Chim Acta* 2007, 595, 107-113, which are incorporated by reference for the corresponding discussion). In the first experiment, there were 90 individual samples (30/strain), each having 1492 data points. This step was standardized as well. First, the spectra from each strain were averaged together to improve the signal to noise (S/N) ratio (see FIG. 20). Next the spectra were preprocessed with the following transformations: the Savitsky-Golay curve fitting $2^{nd}$ order polynomial with the first derivative using a 9 smoothing point sliding window removed instrument noise and provided a baseline correction for more direct spectral comparison (Menezes, J. C.; Correia, M. *J. Anal Chim Acta* 2007, 595, 107-113, which is incorporated by reference for the corresponding discussion). Next, Unit Vector Normalization (UNV) allowed more direct comparison between intensities of peaks within a spectrum and peaks between spectra (Z. B., A. *J Am Soc Mass Spectrom* 2004, 15, 385-387, which is incorporated by reference for the corresponding discussion). Finally, the data were mean-centered so that a statistical software program of Principal Component Analysis (PCA) could simplify the dimensionality of the data set and predict the subsequent ability to build a model of the data for the purpose of classification. The data were analyzed using Hierarchal cluster analysis (HCA), which included more dimensions from PC space to further assess the classification of the data in an unsupervised model. Finally, a supervised training set was created with Partial least squares discriminatory analysis (PLS-DA) to produce a more robust model for differentiation of the strains. The model was tested with the cross-validation Venetian blinds program in Matlab 6.5 software in conjunction with PLS toolbox_4.0 (Incorporated, E. R.; Wise, B. M., Gallagher, N. B., Bro, R., Shaver, J. M., Windig, W., Koch, R. S., Eds.: Wenatchee, WA, 2006, which is incorporated by reference for the corresponding discussion). Thirty spectra for each strain were collected, ten from each of three substrates. Presented in FIG. 20 are the average spectra of the three strains. It is possible to see visible differences in the spectra, but ability to differentiate by eye is not a prerequisite for separation by Chemometrics.

Figure 21:
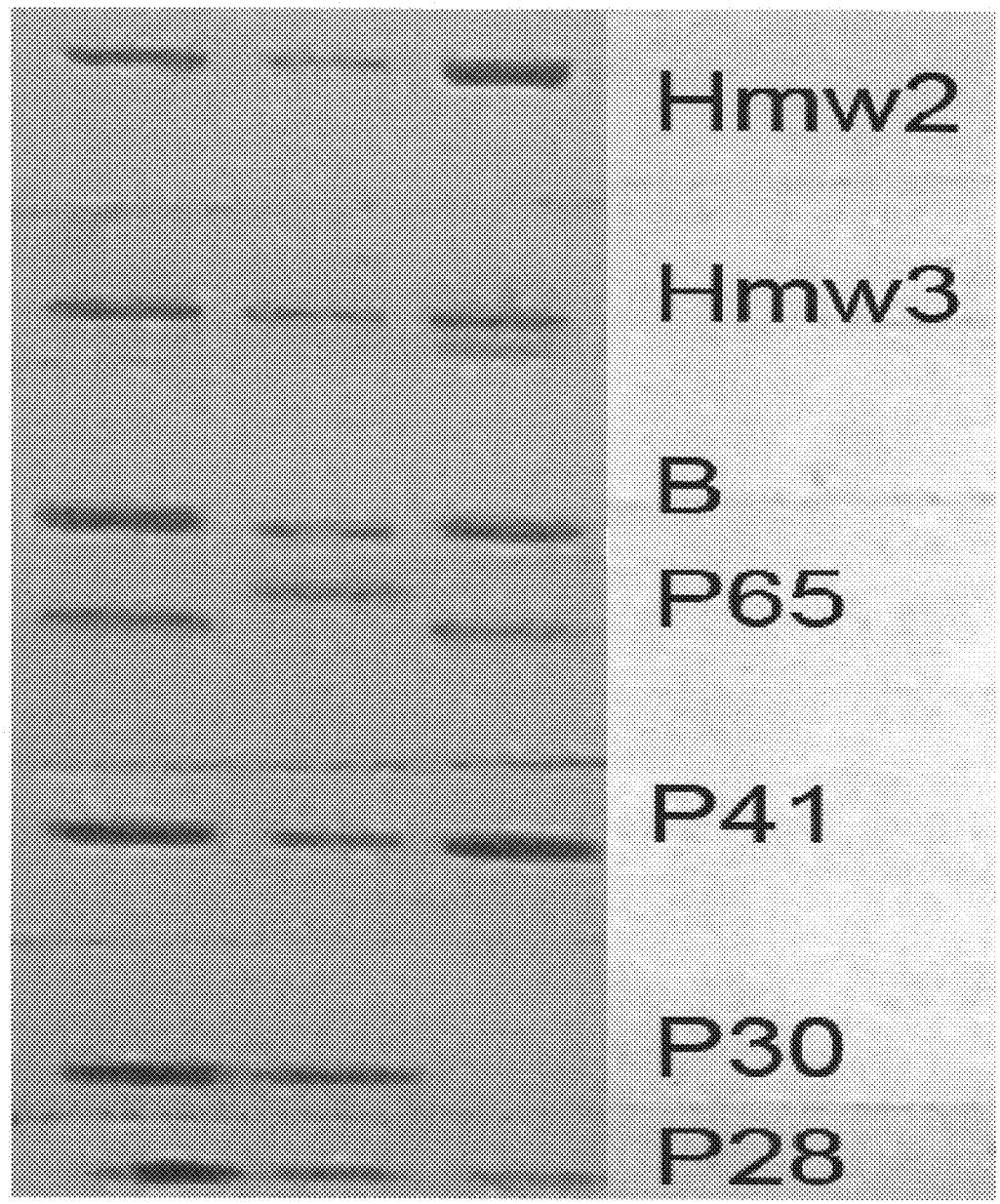
FIG. 21 illustrates SDS-PAGE gel, showing several key surface-exposed protein profiles. FH strain has a 54 bp duplication in P65 protein. II3 is a spontaneous mutant of M129 which has a point deletion, resulting in a frame shift and loss of the P30 protein. Gel prepared by Ed Sheppard.

Three strains of Mpn were selected for this study: M129, FH and II3. M129 and FH are the two prevalent wild types that fluctuate in nature with a periodicity of 4-8 years. Only M129 has been sequenced to date; however, other molecular strategies have revealed some differences between M129 and FH. For this study, one structural difference in the P65 surface-exposed protein is known which could contribute to the variation in spectral patterns (Dumke, R.; Sadowski, C.; Pahlitzsch, S.; Jacobs, E. *International Journal of Medical Microbiology* 2004, 294, 152-153; Jordan, J. L.; Berry, K. M.; Balish, M. F.; Krause, D. C. *J Bacteriol* 2001, 183, 7387-7391, which are incorporated by reference for the corresponding discussion). FH is known to have a 54 base duplication in P65, making it run slower than M129's P65 protein on an SDS-PAGE gel, see FIG. 21. II-3 is a spontaneous mutant of M129, a non-cytadherent apathogenic strain which has a one-base deletion (#483 Adenine) in the P30 gene which results in a frame shift and a non-functional P30 surface-exposed protein (Baseman, J. B.; Cole, R. M.; Krause, D. C.; Leith, D. K. *J Bacteriol* 1982, 151, 1514-1522, which is incorporated by reference for the corresponding discussion). The P65 protein is produced in reduced amounts in II-3, possibly due to P30's contribution to its localization. 1492 individual data points were collected for each spectrum, between the wave numbers 400-1800, the location of the biological fingerprint. The raw spectral data were first transferred into an Excel spreadsheet and then imported into CAMO Unscrambler for initial statistical pre-processing and analysis, followed by exploratory data analysis with PCA.

Figure 22:
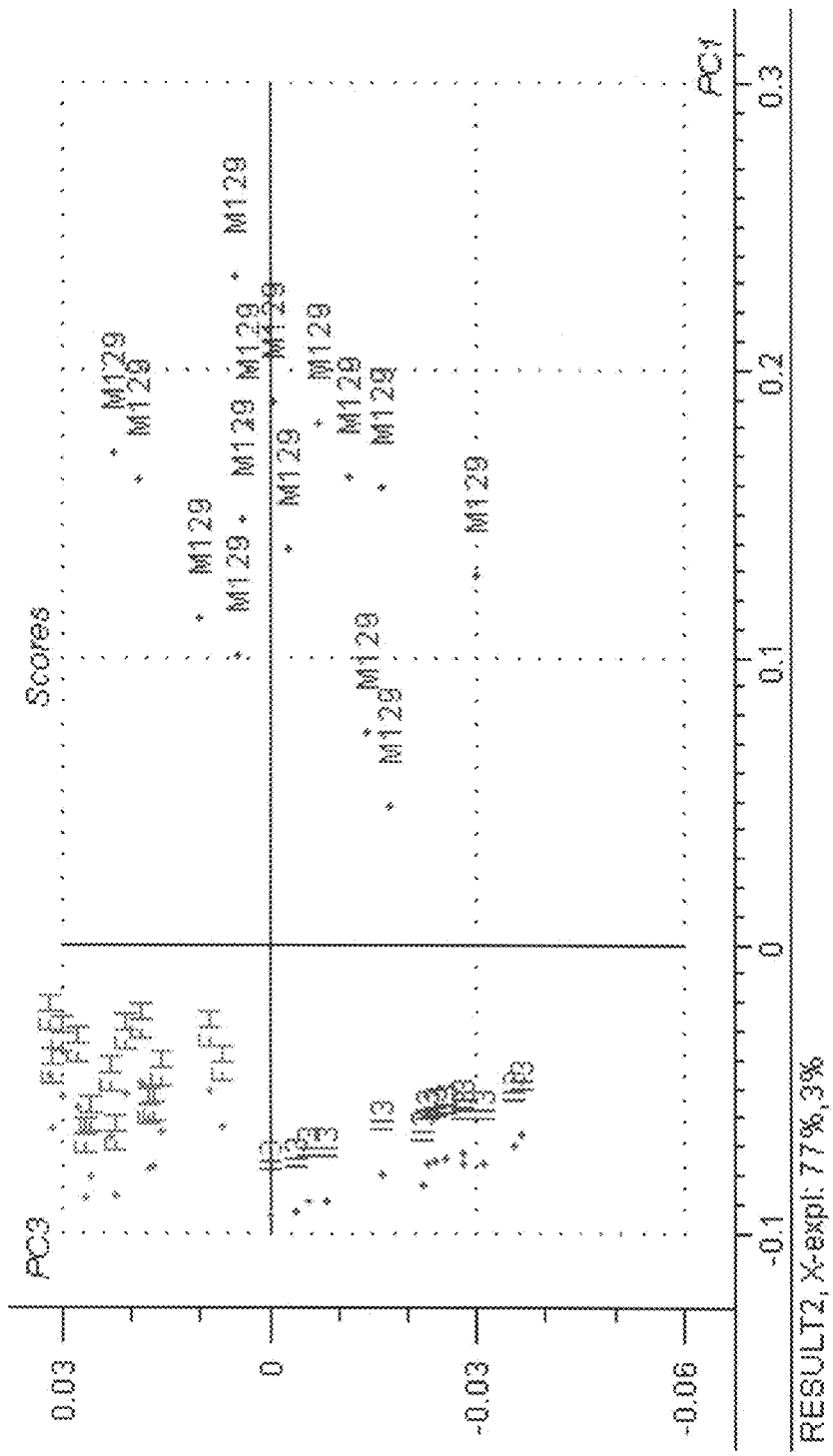
FIG. 22 illustrates Principal Component Analysis (PCA) of *Mycoplasma pneumoniae* strains fixed in methanol (Strains: M129, FH and II3).

FIG. 22 is the PCA output of this data. It is possible to use only the x axis, representing 77% of the total variance in the dataset, Scores plot 1, to separate M129 from the other two strains. With the Scores plot 3, representing 3% of the total variance on the y axis, it is possible to separate FH from II3.

Figure 23:
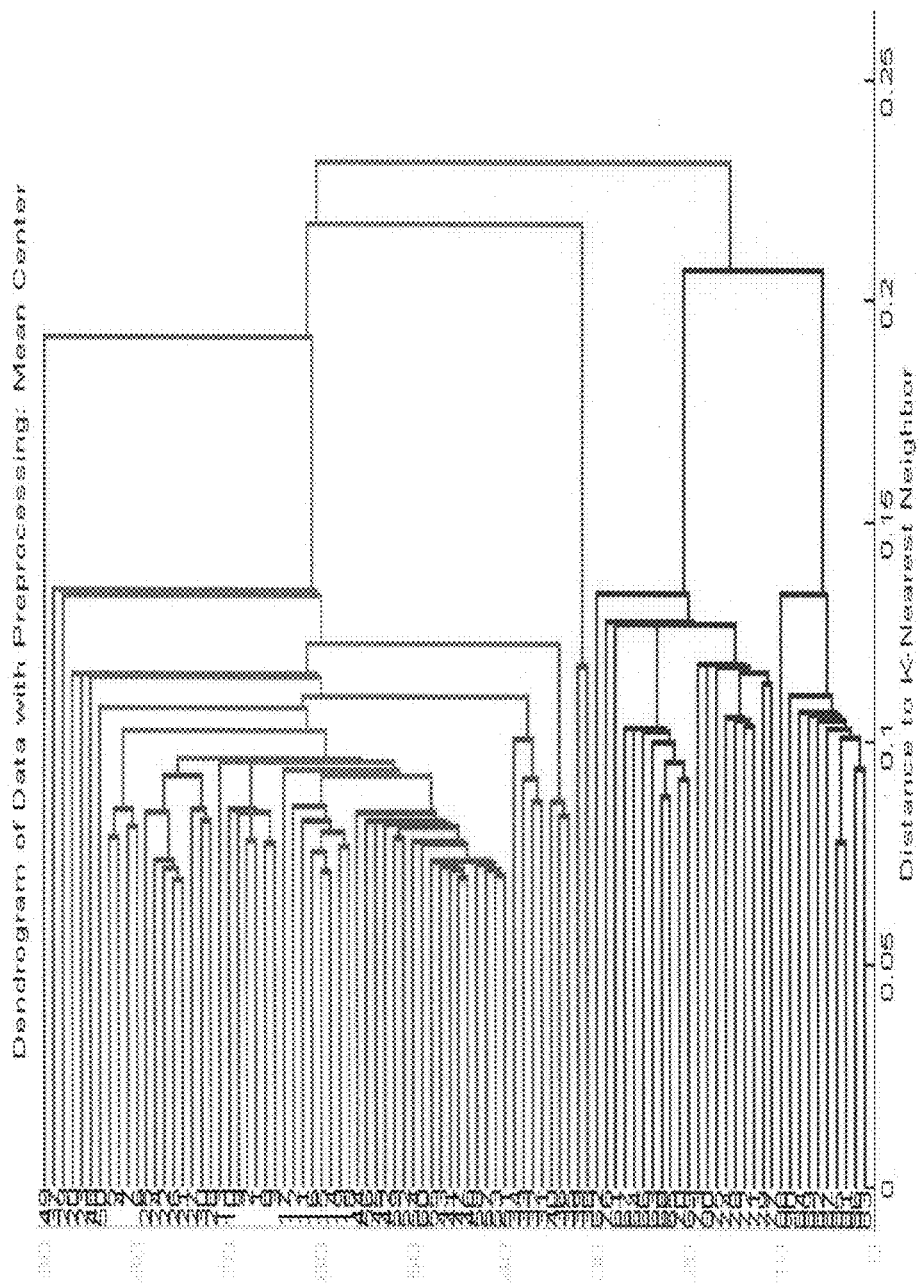
FIG. 23 illustrates Hierarchal Cluster Analysis (HCA) of *Mycoplasma pneumoniae* strains.

Next HCA classified the spectra into a dendogram, using more than two dimensions, making it a more robust method to classify the data than PCA. With 6PCs and using Mahalanobis distance, the dendogram properly classified 86/90 (95.55%) samples, only misclassifying four II3 samples, giving a 4.45% error rate (4/90). See FIG. 23. Finally, by using PLS-DA, a supervised training set with cross validation analysis, a model for classification of the three strains was generated. FIG. 25 is a typical output from this statistical analysis. Highlighted are the cross validation numbers, which assess the model's ability to predict classes. This platform was able to separate M129 from FH and II3 with 100% Specificity and 93-100% Sensitivity.

Next, the sensitivity of this technique was assessed through serial dilutions of the three strains. FH colony forming units were quantified through serial dilution plates and blood overlays done in triplicate and had an initial count of $11.53 \times 10^8$ CFUs. This sample was serially diluted with HPLC grade water to 1:1000000 ($10^{-6}$). PLS-DA was able to detect and differentiate the dilutions of FH with statistical significance, indicated by the CV error rate of 0.02; II3 was differentiated with 0.0329% cross validated error, which is also statistically significant; finally M129 had an error rate of 0.058%, which approaches the statistical rejection level, shown in FIG. 26. Models were constructed from these samples using dilutions and strain classes, and both were able to differentiate the spectra. Thus, this technology appears to have the sensitivity and the specificity that will be necessary for use in clinical settings.

Finally, spectra from different fixative preparations were compared. Surprisingly, the obviously different spectra, (not shown) were still able to be classified correctly with 92.7-97.4% Sensitivity and 95.1-97.5% Specificity with statistical significance. See FIG. 27.

Conclusions

Figure 24:
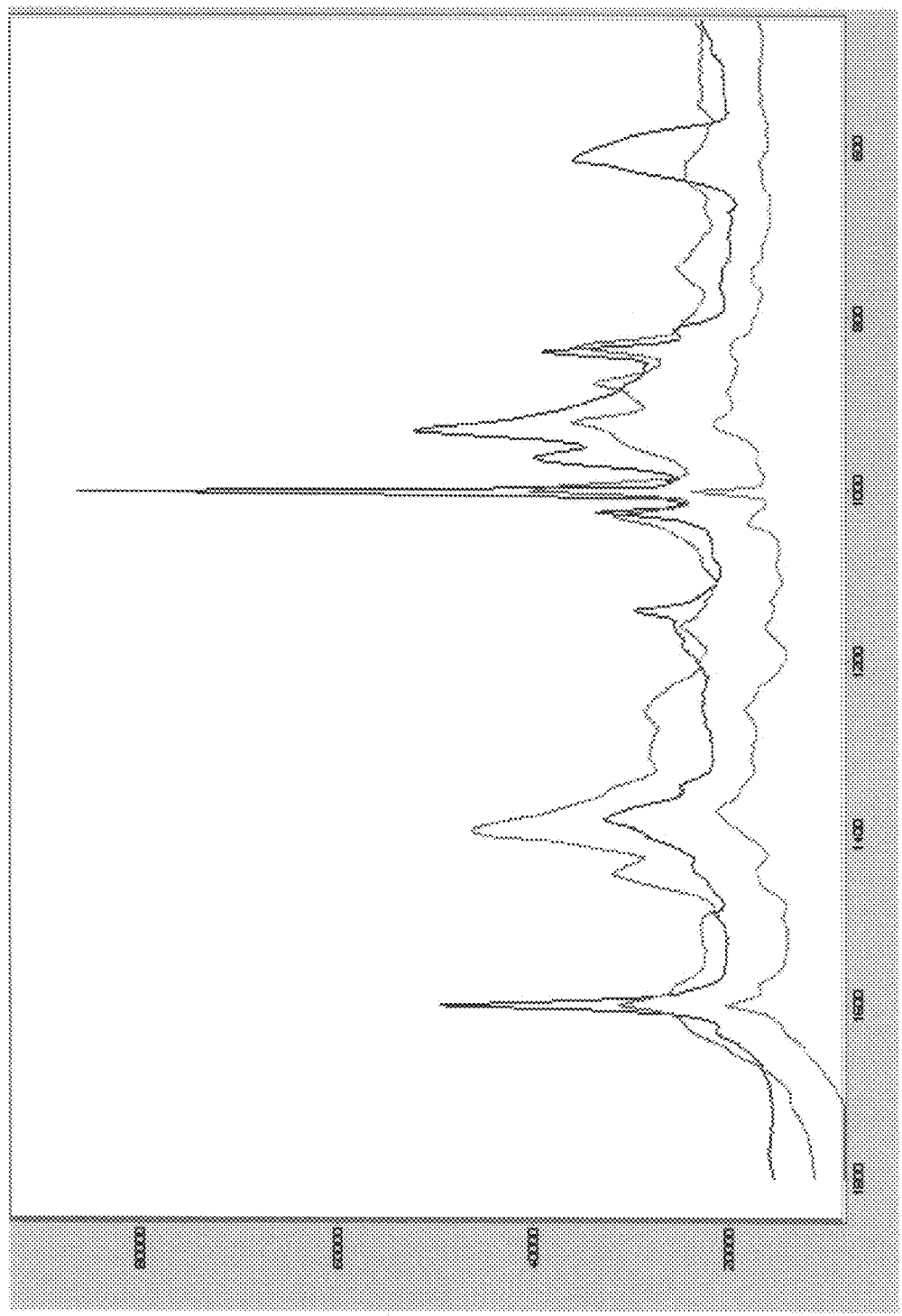
FIG. 24 is a graph that illustrates M129 average spectra in different fixatives.

It is known that *Mycoplasma* surface exposed proteins P30 and P65 contain regions of APR sequences (Alanine, Proline and Arginine). This structural information may contribute to the spectral signals which may be useful for analysis of the strain differences. To this end, the average spectra for each strain were compared with spectral subtraction to determine whether the differences in strains can be related to this known structural information. Previous spectral analysis of amino acids revealed some peak information which can be applied toward the whole organism samples. It should be noted that harvest in water causes a significant number of cells to lyse. This was confirmed through parallel processing of cultures in water and PBS, followed by quantification procedures. In this manner, it was determined that CFU counts lost one log, from $10^8$ in water compared to $10^9$ in PBS. It seems reasonable to expect that cell components remain in the tube after the final re-suspension step before fixation with methanol. Thus, spectra probably include a composite of structural and chemical information from intact cells as well as from the lysed contents of ruptured cells. Since peak assignments were made using simpler molecules, it is not surprising that complex conglomerations of molecules in biological samples and in different backgrounds cause peaks to shift position. For example, the same three strains were fixed using 1% glutaraldehyde and 4% formalin for comparison with methanol. In FIG. 24, the average spectrum for FH in each fixative is presented.

Example 5

Detection of Strains of *Mycoplasma* Bacteria with Silver Nanorod Array SERS

Rationale

Members of the Order Mycoplasmatales contribute to a variety of health, economic and research issues. Specifically, *Mycoplasma pneumoniae* (Mpn) is a human pathogen that is known to cause atypical pneumonia and tracheobronchitis (Hardy, R. D. *Medscape* 2006, which is incorporated by reference for the corresponding discussion) and has been implicated in a variety of chronic conditions ranging from asthma and arthritis to activation of AIDS infections (Xiao-xing, Y.; Yan-hau, Z.; Yi-mou, W. *J Zhejiang Univ SCIENCE B* 2006, 7, 342-350, which is incorporated by reference for the corresponding discussion) and transformation of cells to a cancerous state (Cimolai, N. *Can J Microbiol* 2001, 47, 691-697, which is incorporated by reference for the corresponding discussion). Alternatively, *Mycoplasma gallisepticum*(MG) causes severe chronic respiratory disease in chickens and turkeys resulting in $572 million dollars in annual losses to the poultry industry in the US alone (Service, U. A. R., Ed., 2005; Vol. National programs: animal health, which is incorporated by reference for the corresponding discussion). Therefore, efforts to detect the organisms have progressed from culture methods, to biochemical tests to molecular approaches such as PCR and ELISA. Each approach is limited by either a lack of sensitivity, labor or time intensive preparations, or a confounding level of false positives that stimulate the search for improved detection approaches. The use of Raman Spectroscopy is attractive as a detection method due to the promise of high sensitivity and minimal sample preparation as well as whole organism fingerprinting. It had not been exploited due to inherently weak signal (Jarvis, R. M.; Brooker, A.; Goodacre, R. *Anal Chem* 2004, 76, 5198-5202, which is incorporated by reference for the corresponding discussion). However, the fabrication of nanorod array substrates allows enhancement of the signal to measureable levels with reproducibility that now makes this viable as a biosensing platform (Zhao, Y. P.; Chaney, S. B.; Shanmukh, S.; Dluhy, R. A. *J Phys Chem B* 2006, 110, 3153-3157, which is incorporated by reference for the corresponding discussion).

Work with detecting *Mycoplasma* strains by NA-SERS has progressed in a promising direction. First, efforts to optimize the protocol for use of this platform involved sample preparation changes, such as harvesting in water instead of in PBS due to the destructive nature of Cl ions on the nanorods. Fixation of the samples was examined with 4% formalin, 1% glutaraldehyde and methanol; presentation of the sample on the substrate favored use of methanol to improve homogeneous distribution onto the nanorods. Additionally, instrument settings had to be determined for optimal enhancement. It was determined that the 5× objective allowed more reproducible spectra, presumably due to spatial averaging of a larger area of the sample. The 785 nm laser was set at 5% for maximum power at the surface of 15 mW. Finally, spectra were acquired in 10 seconds; all of these factors contributed to reproducibility of spectra and to elimination of fluorescence or signal saturation issues.

Three strains of *Mycoplasma pneumoniae* were examined by SERS for ability to detect and to differentiate them from one another and from background. M129 and FH are the two dominant serotypes of Mpn seen in clinical settings which have a 4-8 year periodicity. II3 is a spontaneous mutant of M129p25c, non-cytadherent, non-motile filtered clone. Different cultures were grown and prepared for analysis, and multiple spectra were collected on each substrate from samples loaded on different substrates to ensure reproducibility. *Mycoplasma pneumoniae*, the primary cause of atypical pneumonia and tracheobrochitis, has also been implicated in a wide range of chronic diseases, including asthma. The development of the disease state in humans can be complicated by the bacterium's incompletely understood mechanisms to evade the host immune system. It is known that attachment to the epithelial host cell surface is a requirement for onset of pathogenicity (Razin, S. *Biosci Rep* 1999, 19, 367-372, which is incorporated by reference for the corresponding discussion); several hypotheses have emerged to explain the ability of Mpn to persist as a systemic infection, from intracellularization to antigenic variation (Rocha, E. P.; Blanchard, A. *Nucleic Acids Res* 2002, 30, 2031-2042; Yavlovich, A. *FEMS Microbiol Lett* 2004, 233, 241-246, which are incorporated by reference for the corresponding discussion). What is apparent is the need to accurately diagnose its presence for effective treatment. It has been demonstrated that asthma patients who are given antibiotics known to be effective against Mpn show improvements in their conditions (Brunetti, L.; Colazzo, D.; Francavilla, R.; Tesse, R.; De Sario, V.; Lore, M.; Armenio, L. *Allergy Asthma Proc* 2007, 28, 190-193, which is incorporated by reference for the corresponding discussion). Also complicating the diagnosis picture is the frequent co-infection rate by a second agent in conjunction with Mpn. Of the 22% of the community-acquired pneumonia (CAP) cases known to involve Mpn, 64% of them have a second bacterial infection present as well (Wendelien Dorigo-Zetsma, J.; Verkooyen, R. P.; van Helden, H. P.; van der Nat, H.; van den Bosch, J. M. *Journal of Clinical Microbiology* 2001, 39, 1184-1186, which is incorporated by reference for the corresponding discussion).

Three strains of *Mycoplasma gallisepticum* were also compared with this system. A5969, Rlow and S6 were the strains used. Rlow is a low passage pathogenic strain. S6 is a high passage pathogenic strain. A5969 is a high passage apathogenic strain. One strain of *Mycoplasma gallinarum*, a non-pathogenic commensal, was also examined. Research has shown that MG utilizes antigenic variation to evade the host response, and it dedicates 10% of its genome to multiple repeats toward this end (Rocha, E. P.; Blanchard, A. *Nucleic Acids Res* 2002, 30, 2031-2042; Levisohn, S.; Rosengarten, R.; Yogev, D. *Vet Microbiol* 1995, 45, 219-231, which are incorporated by reference for the corresponding discussion). Additionally, MG has been shown to be able to intracellularize to evade the host immune response.

Chemometrics analysis was applied to spectral data. Standardization of the statistical processing of these samples also contributed to the reproducibility of the data. Savitsky-Golay $1^{st}$ derivative with 9 smoothing points is a second order polynomial which produces a baseline correction and improved signal to noise (Savitsky, A.; Golay, M. J. E. *Anal. Chem.* 1964, 36, 1627-1639, which is incorporated by reference for the corresponding discussion). Unit vector normalization allows comparison of peak intensity (Z. B., A. *J Am Soc Mass Spectrom* 2004, 15, 385-387, which is incorporated by reference for the corresponding discussion). Finally, the data were mean centered in order to apply Principal Component Analysis (PCA) (Esbensen, K. H. *Multivariate Data Analysis—in practice*, 5 ed.; CAMO Process: Oslo, 2004, which is incorporated by reference for the corresponding discussion). This is an unsupervised training set that classifies samples using total variance. Hierarchal cluster analysis (HCA) was applied to this data to further classify it. However, the most robust method of classification is with the use of Partial Least Squares Discriminatory Analysis (PLS-DA) (Barker, M.; Rayens, W. *J Chemom* 2003, 17, 166-173, which is incorporated by reference for the corresponding discussion). This is a supervised training set which utilizes variance between strains while preserving variance within strains.

Methods

*Mycoplasma* Sample Preparation

Strains: M129, 18p, FH, 5p, II3, 3 passage. II-3 is a spontaneous mutant that arose from 16 passages of M129. Culture in 25 ml SP4 medium, 25 µl inoculum in 25 ml. Harvest when pH indicator changed to orange, log growth. M129 and FH, pour off medium, Resuspend in chilled HPLC grade H2O, 25 ml. Scrape and transfer to Oakridge tube.

II-3, directly transfer to Oakridge tube without scraping. Beckman Avanti centrifuge, Program 1: 20000×g, 25 min, 4° C. Pour off supernatant. Resuspend in 10 ml chilled H20. Wash 3 times. Program 2: 20000×g, 20 min, 4° C. Last time, resuspend in 1 ml H20 in microcentrifuge tube. Spin in Eppendorf table top centrifuge, 14000 rpm, 15 min, 4° C. Resuspend in 500 µl HPLC grade $H_2O$. Syringe passage 10× with a 25 gauge needle. Transfer 100 µl to previously prepared dilution tubes with 900 µl H2O. Serial dilutions to –10. Transfer 100 µl to PPLO agar plates (in triplicate). After 5 days' growth, blood overlay to visualize colonies.

From original tube, transfer 10 µl (×2) to 90 µl H2O for protein assay, BCA standard protocol. Fixation of samples: add methanol for 1:100 dilution of sample in methanol.

SERS Preparation

Nanorod preparation according to optimized protocol for maximum enhancement of the Raman signal. Briefly, an electron beam sputterer was used with a vacuum chamber for the thin film deposition of three sequential layers, 0.2 kÅ Ti, 5.0 kÅ Ag monolayer, 20.0 kÅ obliquely angled Ag nanorod array; average specs: 868±95 nm length. 90-100 nm diameter, 13 nanorods/µm² density, final angle 70° to normal.

Renishaw Settings:

5× objective. 15 mW power at sample surface, laser spot area=1265 µm². 10 second acquisition. 1492 data points from 400-1800 wave number range were taken. The peak intensities were processed at a CCD detector. The bare nanorods were initially examined for baseline spectral pattern and to determine the level of surface contamination present. 1 µl of sample from each strain was applied to three separate nanorods. Methanol background spectra were collected from ten separate locations on a nanorod.

Chemometric Analysis

Spectral collection with WIRES software. Data transferred into Excel spreadsheet. Creation of a y block in excel. CAMO Unscrambler software for preprocessing: Savitsky Golay, $2^{nd}$ order polynomial first derivative with 9 smoothing points (Savitsky, A.; Golay, M. J. E. *Anal. Chem.* 1964, 36, 1627-1639, which is incorporated by reference for the corresponding discussion). Unit Vector Normalization (Z. B., A. *J Am Soc Mass Spectrom* 2004, 15, 385-387, which is incorporated by reference for the corresponding discussion). PCA analysis (Esbensen, K. H. *Multivariate Data Analysis—in practice*, 5 ed.; CAMO Process: Oslo, 2004, which is incorporated by reference for the corresponding discussion). Exported to Matlab 6.5 with PLS toolbox 4.0, mean centered. HCA cluster analysis. PLS-DA analysis and model construction (Barker, M.; Rayens, W. *J Chemom* 2003, 17, 166-173, which is incorporated by reference for the corresponding discussion).

Results

The Mpn strains were placed into a separate model, and the three strains were differentiable with 93-100% Sensitivity and 93-100% Specificity. The three strains of MG were placed into a separate model and were differentiable with 93.5-100% Sensitivity and 91.8-98.4% Specificity. When models were constructed to examine three different *Mycoplasma* species, the model was able to distinguish and differentiate species with 100% Sensitivity and 100% Specificity. Next, seven strains of *Mycoplasma* from the three different species were placed in a model to differentiate by strain with 96.7-100% Sensitivity and 95.2-100% Specificity. Additionally, dilution studies thus far conducted suggest that the platform will have the necessary sensitivity to detect low levels of pathogens to the single organism level (Grow, A. E.; Wood, L. L.; Claycomb, J. L.; Thompson, P. A. *J Microbiol Methods* 2003, 53, 221-233, which is incorporated by reference for the corresponding discussion). Samples of starting CFUs ranging from $5.8 \times 10^8$ to $6 \times 10^9$ were diluted down to 1 in 1,000,000. Based upon the distribution of the concentration of the sample on the substrate and the area of the sample excited by the laser, subcellular levels of detection are possible. The minimum detection level has not been achieved for *Mycoplasma* samples on this platform to date. A PLS-DA model was constructed both by strain and by dilution, and both were able to segregate classes with statistical significance.

We claim:

1. A method of detecting at least one bacterium in a sample, comprising:

exposing a substrate having an array of nanorods on the substrate to the sample, wherein a tilt angle ($\beta$) between an individual nanorod and the substrate surface is about 0° to about 90°, and wherein the sample includes at least one of a first bacterium and a second bacterium; and measuring a surface enhanced Raman spectroscopy (SERS) spectrum, wherein a SERS spectrum of the array of nanorods and the first bacterium is detectably different than a SERS spectrum of the array of nanorods and the second bacterium.

2. The method of claim 1, wherein the first bacterium and the second bacterium are the same type of bacteria but comprise of different strains, wherein the first bacterial strain has a first measurable surface-enhanced Raman spectroscopic signature, wherein the second bacterial strain has a second measurable surface-enhanced Raman spectroscopic signature and wherein the first measurable surface-enhanced spectroscopic signature and the second measurable surface-enhanced Raman spectroscopic signature are distinguishable.

3. The method of claim 2, wherein each of the first bacterium and the second bacterium are selected from *Mycoplasma*, *Ureaplasma*, *Spriroplasma* and *Phytoplasma*, or other members of the taxonomic class Mollicutes.

4. The method of claim 2, wherein each of the first and the second bacteria is selected from *Mycoplasma mycoides*, *Mycoplasma pulmonis*, *Mycoplasma hominis*, *Mycoplasma muris*, *Mycoplasma fastidiosum*, *Mycoplasma pneumoniae*, *Mycoplasma alvi*, *Mycoplasma amphoriforme*, *Mycoplasma gallisepticum*, *Mycoplasma genitalium*, *Mycoplasma imitans*, *Mycoplasma pirum*, *and Mycoplasma iowae*, *Mycoplasma hemofelis*, *Ca. Mycoplasma turicensis*, *Ca. Mycoplasma hemominitum*, *Mycoplasma mobile*, *Mycoplasma alligatoris*, *Mycoplasma crocodyli*, *Mycoplasma bovis*, *Mycoplasma putrefaciens*, *Mycoplasma cottewii*, *Mycoplasma yeatsii*, *Mycoplasma agalactiae*, *Mycoplasma suis*, *Mycoplasma arthritidis*, *Mycoplasma fermentans*, *Mycoplasma penetrans*, *Mycoplasma hyopneumoniae*, *Mycoplasma capricolum*, *Mycoplasma falconis*, *Mycoplasma bovigenitalium*, *Mycoplasma ovipneumoniae*, *Mycoplasma hyorhinis*, or *Mycoplasma testudines*.

5. The method of claim 2, wherein the first bacterium and the second bacterium comprise different strains of *Mycoplasma pneumoniae*.

6. The method of claim 5, wherein the strains of *Mycoplasma pneumoniae* are selected from M129, FH, and II-3.

7. The method of claim 2, further comprising analyzing the measurable surface-enhanced Raman spectroscopic spectrum for each bacterium by the use of an analysis method selected from at least one of Principal component analysis (PCA) or K-means Clustering Algorithm analysis.

8. A method of detecting at least one virus in a sample, comprising:

exposing a substrate having an array of nanorods on the substrate to the sample, wherein a tilt angle ($\beta$) between an individual nanorod and the substrate surface is about 0° to about 90°, and wherein the sample includes at least one of a first Rotavirus and a second Rotavirus; and measuring a surface enhanced Raman spectroscopy (SERS) spectrum, wherein a SERS spectrum of the array of nanorods and the first Rotavirus is detectably different than a SERS spectrum of the array of nanorods and the second Rotavirus.

9. The method of claim 8, wherein the first Rotavirus and the second Rotavirus are each a different strain of Rotavirus (RV).

10. The method of claim 9, wherein the first Rotavirus and the second Rotavirus are the same type of Rotavirus but comprise of different strains, wherein the first viral strain has a first measurable surface-enhanced Raman spectroscopic signature, wherein the second viral strain has a second measurable surface-enhanced Raman spectroscopic signature and wherein the first measurable surface-enhanced spectroscopic signature and the second measurable surface-enhanced Raman spectroscopic signature are distinguishable.

11. The method of claim 9, wherein the strains of rotavirus (RV) are selected from RV4, WA, RV5, S2, RV3, YO, F45, or ST-3.

12. The method of claim 8, further comprising analyzing the measurable surface-enhanced Raman spectroscopic spectrum for each Rotavirus by the use of an analysis method selected from at least one of Principal component analysis (PCA) or K-means Clustering Algorithm analysis.

13. A method of detecting at least one biomolecule in a sample, comprising:

attaching at least one first biomolecule to an array of nanorods on a substrate, wherein a tilt angle ($\beta$) between an individual nanorod and the substrate surface is about 0° to about 90°;

exposing the substrate including the first biomolecule to the sample containing at least one of a second biomolecule and a third biomolecule, wherein the second biomolecule is a first strain of Rotavirus (RV) and the third biomolecule is a second strain of Rotavirus (RV); and measuring a surface enhanced Raman spectroscopy (SERS) spectrum, wherein a SERS spectrum of the array of nanorods and the first biomolecule is detectably different than a SERS spectrum of the array of nanorods, the first biomolecule, and the second biomolecule and a SERS spectrum of the array of nanorods, the first biomolecule, and the third biomolecule, and wherein the SERS spectrum of the array of nanorods, the first biomolecule, and the second biomolecule is detectably different than the SERS spectrum of the array of nanorods, the first biomolecule, and the third biomolecule.

14. The method of claim 13, wherein the first biomolecule is selected from: a polynucleotide, a protein, a polypeptide, a glycoprotein, a lipid, a carbohydrate, a fatty acid, a fatty ester, a macromolecular polypeptide complex, or combinations thereof.

15. The method of claim 13, where in each of the second biomolecule and the third biomolecule are a bacterium selected from *Mycoplasma, Ureaplasma, Spiroplasma, Phytoplasma*, or other members of the taxonomic class Mollicutes.

16. The method of claim 1, wherein the tilt angle ($\beta$) between an individual nanorod and the substrate surface is about 0° to about 50°.

17. The method of claim 1, wherein the tilt angle ($\beta$) between an individual nanorod and the substrate surface is about 5° to about 20°.

18. The method of claim 1, wherein the tilt angle ($\beta$) between an individual nanorod and the substrate surface is about 15° to about 30°.

19. The method of claim 1, wherein the tilt angle ($\beta$) between an individual nanorod and the substrate surface is about 25° to about 40°.

20. The method of claim 8, wherein the tilt angle ($\beta$) between an individual nanorod and the substrate surface is about 0° to about 50°.

21. The method of claim 8, wherein the tilt angle ($\beta$) between an individual nanorod and the substrate surface is about 5° to about 20°.

22. The method of claim 8, wherein the tilt angle ($\beta$) between an individual nanorod and the substrate surface is about 15° to about 30°.

23. The method of claim 8, wherein the tilt angle ($\beta$) between an individual nanorod and the substrate surface is about 25° to about 40°.

* * * * *